US008880576B2

(12) United States Patent
Ochs et al.

(10) Patent No.: US 8,880,576 B2
(45) Date of Patent: Nov. 4, 2014

(54) SYSTEMS AND METHODS FOR DETERMINING RESPIRATION INFORMATION FROM A PHOTOPLETHYSMOGRAPH

(75) Inventors: James Ochs, Seattle, WA (US); Paul S. Addison, Edinburgh Midlothian (GB); James Watson, Fife (GB)

(73) Assignee: Nellcor Puritan Bennett Ireland, Galway (IE)

( * ) Notice: Subject to any disclaimer, the term of this patent is extended or adjusted under 35 U.S.C. 154(b) by 551 days.

(21) Appl. No.: 13/243,951

(22) Filed: Sep. 23, 2011

(65) Prior Publication Data

US 2013/0080489 A1    Mar. 28, 2013

(51) Int. Cl.
| | | |
|---|---|---|
| *G06F 17/15* | (2006.01) | |
| *A61B 5/024* | (2006.01) | |
| *A61B 5/0205* | (2006.01) | |
| *A61B 5/08* | (2006.01) | |
| *A61B 5/00* | (2006.01) | |

(52) U.S. Cl.
CPC .............. *A61B 5/08* (2013.01); *A61B 5/02416* (2013.01); *A61B 5/0205* (2013.01); *A61B 5/0816* (2013.01); *A61B 5/7203* (2013.01)
USPC ....................................................... 708/426

(58) Field of Classification Search
CPC ....... G06F 17/15; G06F 7/1935; C08G 69/44; G01B 7/34; G01B 1/00
USPC ....................................................... 708/426
See application file for complete search history.

(56) References Cited

U.S. PATENT DOCUMENTS

| 5,188,108 A | 2/1993 | Secker |
| 5,285,783 A | 2/1994 | Secker |
| 5,285,784 A | 2/1994 | Secker |
| 5,368,026 A | 11/1994 | Swedlow et al. |
| 5,398,682 A | 3/1995 | Lynn |
| 5,558,096 A | 9/1996 | Palatnik |
| 5,584,295 A | 12/1996 | Muller et al. |
| 5,588,425 A | 12/1996 | Sackner et al. |

(Continued)

FOREIGN PATENT DOCUMENTS

| EP | 0072601 A1 | 2/1983 |
| EP | 1344488 A2 | 9/2004 |

(Continued)

OTHER PUBLICATIONS

Stagg and Gennser, "Electronic analysis of foetal breathing movements: A practical application of phase-locked-loop principles," Journal of Med. Eng. and Tech., Sep. 1978, vol. 2, No. 5, pp. 246-249.

(Continued)

*Primary Examiner* — Tan V. Mai
(74) *Attorney, Agent, or Firm* — Shvarts & Leiz LLP.

(57) ABSTRACT

A patient monitoring system may receive a photoplethysmograph (PPG) signal including samples of a pulse waveform. A plurality of morphology metric signals may be generated from the PPG signal. The system may generate an autocorrelation sequence for each of the morphology metric signals. An autocorrelation metric may be generated from each of the autocorrelation sequences and may represent the regularity or periodicity of the morphology metric signal. The autocorrelation sequences may be combined to generate a combined autocorrelation sequence, with the weighting of the autocorrelation sequences based on the autocorrelation metric. The combined autocorrelation sequence may be used to determine physiological information.

20 Claims, 26 Drawing Sheets

(56) References Cited

U.S. PATENT DOCUMENTS

| | | |
|---|---|---|
| 5,605,151 A | 2/1997 | Lynn |
| 5,862,805 A | 1/1999 | Nitzan |
| 5,865,736 A | 2/1999 | Baker et al. |
| 5,891,023 A | 4/1999 | Lynn |
| 6,002,952 A | 12/1999 | Diab et al. |
| 6,035,223 A | 3/2000 | Baker |
| 6,081,742 A | 6/2000 | Amano et al. |
| 6,095,984 A | 8/2000 | Amano et al. |
| 6,129,675 A | 10/2000 | Jay |
| 6,135,966 A | 10/2000 | Ko |
| 6,178,261 B1 | 1/2001 | Williams et al. |
| 6,223,064 B1 | 4/2001 | Lynn |
| 6,229,856 B1 | 5/2001 | Diab et al. |
| 6,238,351 B1 | 5/2001 | Orr et al. |
| 6,325,761 B1 | 12/2001 | Jay |
| 6,334,065 B1 | 12/2001 | Al-Ali et al. |
| 6,342,039 B1 | 1/2002 | Lynn et al. |
| 6,350,242 B1 | 2/2002 | Doten et al. |
| 6,405,076 B1 | 6/2002 | Taylor et al. |
| 6,463,311 B1 | 10/2002 | Diab |
| 6,506,153 B1 | 1/2003 | Littek et al. |
| 6,561,986 B2 | 5/2003 | Baura et al. |
| 6,564,077 B2 | 5/2003 | Mortara |
| 6,606,511 B1 | 8/2003 | Al-Ali et al. |
| 6,609,016 B1 | 8/2003 | Lynn |
| 6,684,090 B2 | 1/2004 | Al-Ali et al. |
| 6,694,178 B1 | 2/2004 | Soula et al. |
| 6,702,752 B2 | 3/2004 | Dekker |
| 6,709,402 B2 | 3/2004 | Dekker |
| 6,748,252 B2 | 6/2004 | Lynn et al. |
| 6,754,516 B2 | 6/2004 | Mannheimer |
| 6,760,608 B2 | 7/2004 | Lynn |
| 6,783,498 B2 | 8/2004 | Sackner et al. |
| 6,816,741 B2 | 11/2004 | Diab |
| 6,839,581 B1 | 1/2005 | El Solh et al. |
| 6,896,661 B2 | 5/2005 | Dekker |
| 6,905,470 B2 | 6/2005 | Lee et al. |
| 6,925,324 B2 | 8/2005 | Shusterman |
| 6,931,269 B2 | 8/2005 | Terry |
| 6,966,878 B2 | 11/2005 | Schoisswohl et al. |
| 6,970,792 B1 | 11/2005 | Diab |
| 6,980,679 B2 | 12/2005 | Jeung et al. |
| 7,020,507 B2 | 3/2006 | Scharf et al. |
| 7,035,679 B2 | 4/2006 | Addison et al. |
| 7,043,293 B1 | 5/2006 | Baura |
| 7,044,918 B2 | 5/2006 | Diab |
| 7,070,566 B2 | 7/2006 | Medero et al. |
| 7,079,888 B2 | 7/2006 | Oung et al. |
| 7,147,601 B2 | 12/2006 | Marks et al. |
| 7,177,682 B2 | 2/2007 | Lovett |
| 7,190,261 B2 | 3/2007 | Al-Ali |
| 7,215,986 B2 | 5/2007 | Diab et al. |
| 7,218,966 B2 | 5/2007 | Haefner |
| 7,254,425 B2 | 8/2007 | Lowery et al. |
| 7,283,870 B2 | 10/2007 | Kaiser et al. |
| 7,336,982 B2 | 2/2008 | Yoo |
| 7,355,512 B1 | 4/2008 | Al-Ali |
| 7,367,339 B2 | 5/2008 | Bickle |
| 7,367,949 B2 | 5/2008 | Korhonen et al. |
| 7,398,115 B2 | 7/2008 | Lynn |
| 7,403,806 B2 | 7/2008 | Norris |
| 7,407,486 B2 | 8/2008 | Huiku et al. |
| 7,409,241 B2 * | 8/2008 | Vitali et al. ............. 600/513 |
| 7,415,297 B2 | 8/2008 | Al-Ali et al. |
| 7,438,683 B2 | 10/2008 | Al-Ali et al. |
| 7,440,787 B2 | 10/2008 | Diab |
| 7,470,235 B2 | 12/2008 | Moriya et al. |
| 7,485,095 B2 | 2/2009 | Shusterman |
| 7,496,393 B2 | 2/2009 | Diab et al. |
| 7,499,835 B2 | 3/2009 | Weber et al. |
| 7,523,011 B2 | 4/2009 | Akiyama et al. |
| 7,561,912 B2 | 7/2009 | Schatz et al. |
| 7,610,324 B2 | 10/2009 | Troyansky et al. |
| 7,690,378 B1 | 4/2010 | Turcott |
| 7,801,591 B1 | 9/2010 | Shusterman |
| 7,869,980 B2 | 1/2011 | Casler et al. |
| 7,894,868 B2 | 2/2011 | Al-Ali et al. |
| 7,899,507 B2 | 3/2011 | Al-Ali et al. |
| 7,976,472 B2 | 7/2011 | Kiani |
| 7,988,637 B2 | 8/2011 | Diab |
| 8,019,400 B2 | 9/2011 | Diab et al. |
| 8,046,040 B2 | 10/2011 | Al-Ali et al. |
| 8,130,105 B2 | 3/2012 | Al-Ali et al. |
| 8,203,438 B2 | 6/2012 | Kiani et al. |
| 8,275,553 B2 | 9/2012 | Amundson et al. |
| 8,364,226 B2 | 1/2013 | Diab et al. |
| 2002/0117173 A1 | 8/2002 | Lynn et al. |
| 2003/0036685 A1 | 2/2003 | Goodman |
| 2003/0158466 A1 | 8/2003 | Lynn |
| 2003/0163054 A1 | 8/2003 | Dekker |
| 2004/0015091 A1 | 1/2004 | Greenwald et al. |
| 2005/0004479 A1 | 1/2005 | Townsend et al. |
| 2005/0022606 A1 | 2/2005 | Partin et al. |
| 2005/0027205 A1 | 2/2005 | Tarassenko et al. |
| 2005/0049470 A1 | 3/2005 | Terry |
| 2005/0070774 A1 | 3/2005 | Addison et al. |
| 2005/0222502 A1 | 10/2005 | Cooper |
| 2005/0222503 A1 | 10/2005 | Dunlop et al. |
| 2006/0122476 A1 | 6/2006 | Van Slyke |
| 2006/0192667 A1 | 8/2006 | Al-Ali |
| 2006/0211930 A1 | 9/2006 | Scharf et al. |
| 2006/0217614 A1 | 9/2006 | Takala et al. |
| 2006/0258921 A1 | 11/2006 | Addison et al. |
| 2007/0004977 A1 | 1/2007 | Norris |
| 2007/0010723 A1 | 1/2007 | Uetela et al. |
| 2007/0073120 A1 | 3/2007 | Li et al. |
| 2007/0073124 A1 | 3/2007 | Li et al. |
| 2007/0129636 A1 | 6/2007 | Friedman et al. |
| 2007/0149890 A1 | 6/2007 | Li et al. |
| 2007/0179369 A1 | 8/2007 | Baker |
| 2007/0213619 A1 | 9/2007 | Linder |
| 2007/0213621 A1 | 9/2007 | Reisfeld et al. |
| 2007/0255146 A1 | 11/2007 | Andrews et al. |
| 2007/0293896 A1 | 12/2007 | Haefner |
| 2008/0077022 A1 | 3/2008 | Baker |
| 2008/0167540 A1 | 7/2008 | Korhonen et al. |
| 2008/0200775 A1 | 8/2008 | Lynn |
| 2009/0247837 A1 | 10/2009 | Ochs et al. |
| 2009/0326349 A1 | 12/2009 | McGonigle |
| 2009/0326395 A1 | 12/2009 | Watson |
| 2009/0326831 A1 | 12/2009 | McGonigle et al. |
| 2010/0113904 A1 | 5/2010 | Batchelder et al. |
| 2010/0113908 A1 | 5/2010 | Vargas et al. |
| 2010/0113909 A1 | 5/2010 | Batchelder et al. |
| 2010/0286495 A1 | 11/2010 | McGonigle |
| 2011/0066062 A1 | 3/2011 | Banet et al. |
| 2011/0071406 A1 | 3/2011 | Addison et al. |

FOREIGN PATENT DOCUMENTS

| | | |
|---|---|---|
| EP | 1507474 B1 | 2/2009 |
| WO | WO 00/21438 | 4/2000 |
| WO | WO 03/000125 A1 | 1/2003 |
| WO | WO 03/055395 A1 | 7/2003 |
| WO | WO 03/084396 A1 | 10/2003 |
| WO | WO 2004/075746 A2 | 9/2004 |
| WO | WO 2010/030238 A1 | 3/2010 |

OTHER PUBLICATIONS

Rapaport and Cousin, "New phase-lock tracking instrument for foetal breathing monitoring," Med. & Biol. Eng. & Comp. 1982, vol. 20, pp. 1-6.

Lindberg, L.G., Ughall, H., Oberg, P.A., "Monitoring of respiratory and heart rates using a fibre-optic sensor," Medical & Biological Engineering & Computing, Sep. 1992, pp. 533-537.

* cited by examiner

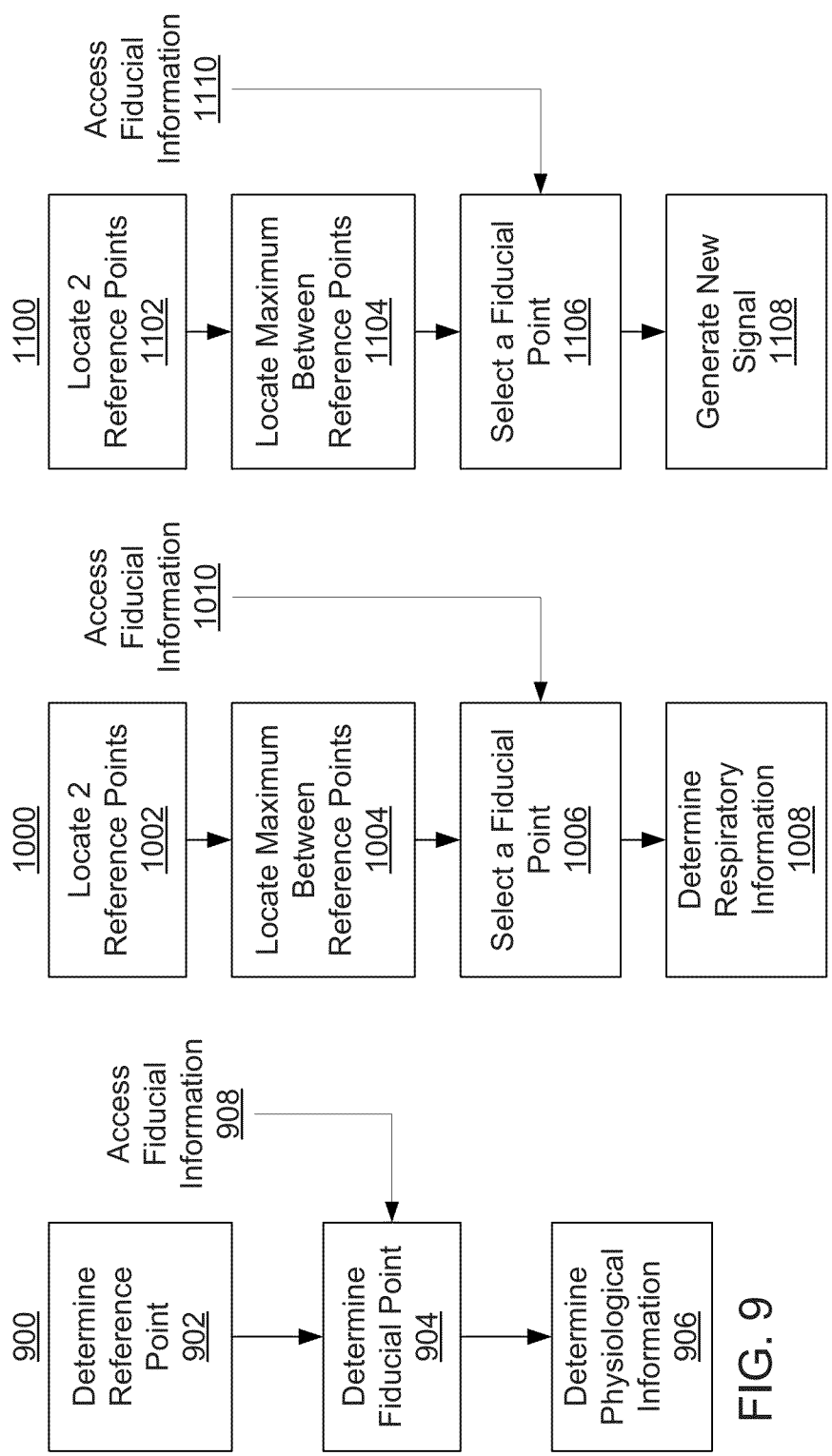

US 8,880,576 B2

SYSTEMS AND METHODS FOR DETERMINING RESPIRATION INFORMATION FROM A PHOTOPLETHYSMOGRAPH

The present disclosure relates to physiological signal processing, and more particularly relates to extracting respiratory information from a photoplethysmograph signal.

SUMMARY

A patient monitoring system may be configured to determine physiological information from a physiological signal using a suitable combination of one or more reference points in the physiological signal and one or more fiducial points in the physiological signal. A reference point may be determined by performing mathematical calculations on the physiological signal to find minima, maxima, zeros or other points of a physiological signal or signal derived thereof (e.g., derivatives, integrals). A fiducial point may be used to calculate physiological information, signal metrics, or other information. The patient monitoring system may determine a reference point on a sampled physiological signal, and then determine a fiducial point on the sampled physiological signal based at least in part on the reference point and based at least in part on a time interval relative to the reference point. For example, the patient monitoring system may select a set of fiducial points located 210 milliseconds from a set of respective local maxima of the first derivative of a photoplethysmograph signal (e.g., maxima of the first derivative of each pulse wave), and determine a respiration rate based on the set of fiducial points. The time difference may be a predetermined value, or may depend on physiological information such as an instantaneous pulse rate. The patient monitoring system may create a fiducial signal based at least in part on determined fiducial points, and may determine physiological information based at least in part on the newly created signal.

In some embodiments, a patient monitoring system may locate two successive reference points corresponding to two successive pulse waves of a sampled photoplethysmograph signal. The patient monitoring system may then locate a maximum value of the first derivative of the sampled signal between the two successive reference points. Using the location of the maximum value as a further reference point, the patient monitoring system may select a fiducial point located a particular time interval (or corresponding number of samples) before or after the maximum value. Based on the fiducial points, the patient monitoring system may determine respiratory information such as, for example, a respiration rate. In some embodiments, the fiducial point may be located a predetermined time interval (or corresponding number of samples) away from the maximum value. In some embodiments, the particular time interval (or corresponding number of samples) is based at least in part on physiological information such as an average heart rate. For example, the particular time interval (or corresponding number of samples) may be 10% of the pulse period of the averaged heart rate (i.e., about 100 milliseconds corresponding to a 60 BPM averaged heart rate).

BRIEF DESCRIPTION OF THE FIGURES

The above and other features of the present disclosure, its nature and various advantages will be more apparent upon consideration of the following detailed description, taken in conjunction with the accompanying drawings in which:

FIG. 9 is flow diagram showing illustrative steps for determining physiological information in accordance with some embodiments of the present disclosure;

FIG. 10 is flow diagram showing illustrative steps for determining respiration information in accordance with some embodiments of the present disclosure;

FIG. 11 is flow diagram showing illustrative steps for generating a fiducial signal from a physiological signal in accordance with some embodiments of the present disclosure;

DETAILED DESCRIPTION OF THE FIGURES

Figure 1:
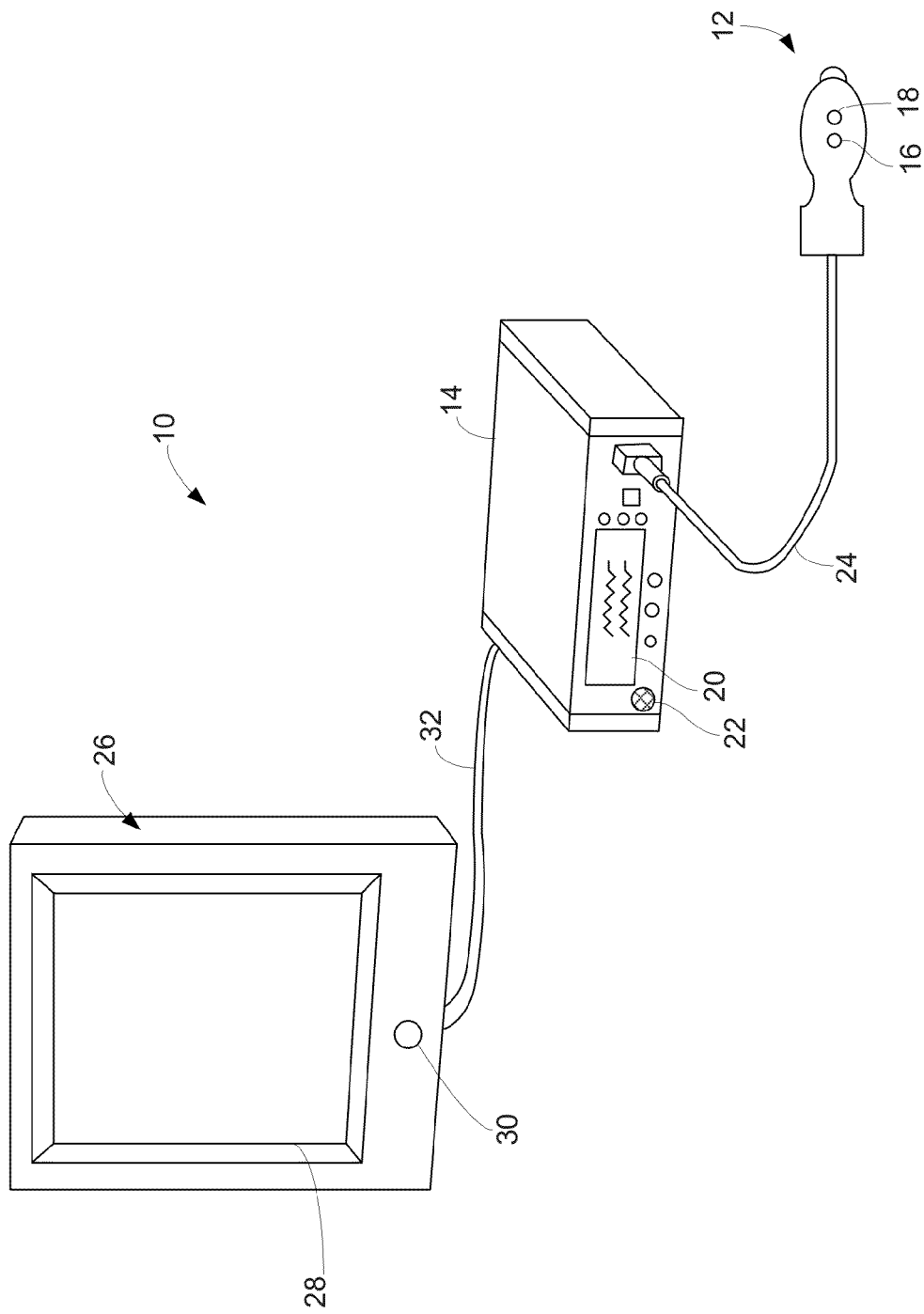
FIG. 1 shows an illustrative patient monitoring system in accordance with some embodiments of the present disclosure.

The present disclosure is directed towards determining respiration information from a physiological signal. A patient monitoring system may receive one or more physiological signals, such as a photoplethysmograph (PPG) signal generated by a pulse oximeter, from a sensor coupled to a patient. The patient monitoring system may condition (e.g., amplify, filter, sample, digitize) physiological signals received from the sensor, perform suitable mathematical calculations on the conditioned signals to locate reference points, and determine one or more fiducial points of the conditioned signal.

Fiducial-defined portions may be determined based on the fiducial points. In some embodiments, suitable mathematical calculations may be performed on the fiducial defined portions of the physiological signal to obtain one or more morphology metrics, such as a down metric, a kurtosis metric, and a delta of second derivative (DSD) metric. An interpolated signal may be generated for each of the morphology metrics to generate a down metric signal, a kurtosis metric signal, and a DSD metric signal.

An autocorrelation may be performed on each morphology metric signal to generate one or more autocorrelation sequences, e.g., to indicate the regularity or periodicity of the morphology metric signals. The autocorrelation sequences may be combined based on the autocorrelation metrics to generate a combined autocorrelation sequence.

The autocorrelation sequence may be used to determine respiration information such as respiration rate. In one exemplary embodiment the respiration information may be determined from the autocorrelation sequence. In another exemplary embodiment a wavelet transform may be utilized to determine the respiration information. The system may perform a convolution of a signal to be analyzed and a mother wavelet, based on scaling parameters such as a scale resolution and number of scales. A scalogram may be generated based on the mother wavelet, and a threshold may be calculated for the scalogram. Scales meeting the threshold may be candidate scales for determining respiration information. The respiration information may be determined from a selected scale of the candidate scales based on the wavelet characteristic frequency corresponding to the selected scale.

An oximeter is a medical device that may determine the oxygen saturation of the blood. One common type of oximeter is a pulse oximeter, which may indirectly measure the oxygen saturation of a patient's blood (as opposed to measuring oxygen saturation directly by analyzing a blood sample taken from the patient). Pulse oximeters may be included in patient monitoring systems that measure and display various blood flow characteristics including, but not limited to, the oxygen saturation of hemoglobin in arterial blood. Such patient monitoring systems may also measure and display additional physiological parameters, such as a patient's pulse rate.

An oximeter may include a light sensor that is placed at a site on a patient, typically a fingertip, toe, forehead or earlobe, or in the case of a neonate, across a foot. The oximeter may use a light source to pass light through blood perfused tissue and photoelectrically sense the absorption of the light in the tissue. In addition, locations that are not typically understood to be optimal for pulse oximetry serve as suitable sensor locations for the monitoring processes described herein, including any location on the body that has a strong pulsatile arterial flow. For example, additional suitable sensor locations include, without limitation, the neck to monitor carotid artery pulsatile flow, the wrist to monitor radial artery pulsatile flow, the inside of a patient's thigh to monitor femoral artery pulsatile flow, the ankle to monitor tibial artery pulsatile flow, and around or in front of the ear. Suitable sensors for these locations may include sensors for sensing absorbed light based on detecting reflected light. In all suitable locations, for example, the oximeter may measure the intensity of light that is received at the light sensor as a function of time. The oximeter may also include sensors at multiple locations. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate any of a number of physiological parameters, including an amount of a blood constituent (e.g., oxyhemoglobin) being measured as well as a pulse rate and when each individual pulse occurs.

In some applications, the light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared (IR) wavelengths may be used because it has been observed that highly oxygenated blood will absorb relatively less Red light and more IR light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based at least in part on Lambert-Beer's law. The following notation will be used herein:

$$I(\lambda,t) = I_O(\lambda) \exp(-(s\beta_O)(\lambda) + (1-s)\beta_r(\lambda))l(t)) \quad (1)$$

where:
$\lambda$=wavelength;
t=time;
I=intensity of light detected;
$I_0$=intensity of light transmitted;
s=oxygen saturation;
$\beta_o/\beta_r$-empirically derived absorption coefficients; and
l(t)=a combination of concentration and path length from emitter to detector as a function of time.

The traditional approach measures light absorption at two wavelengths (e.g., Red and IR), and then calculates saturation by solving for the "ratio of ratios" as follows.

1. The natural logarithm of Eq. 1 is taken ("log" will be used to represent the natural logarithm) for IR and Red to yield $$\log I = \log I_o - (s\beta_o + (1-s)\beta_r)l. \quad (2)$$

2. Eq. 2 is then differentiated with respect to time to yield $$\frac{d\log I}{dt} = -(s\beta_o + (1-s)\beta_r)\frac{dl}{dt}. \quad (3)$$

3. Eq. 3, evaluated at the Red wavelength $\lambda_R$, is divided by Eq. 3 evaluated at the IR wavelength $\lambda_{IR}$ in accordance with $$\frac{d\log I(\lambda_R)/dt}{d\log I(\lambda_{IR})/dt} = \frac{s\beta_o(\lambda_R) + (1-s)\beta_r(\lambda_R)}{s\beta_o(\lambda_{IR}) + (1-s)\beta_r(\lambda_{IR})}. \quad (4)$$

4. Solving for s yields $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_o(\lambda_{IR}) - \beta_r(\lambda_{IR})) - \frac{d\log I(\lambda_R)}{dt}\left(\frac{\beta_o(\lambda_R) - }{\beta_r(\lambda_R)}\right)}. \quad (5)$$

5. Note that, in discrete time, the following approximation can be made:

$$\frac{d\log I(\lambda, t)}{dt} \simeq \log I(\lambda, t_2) - \log I(\lambda, t_1). \quad (6)$$

6. Rewriting Eq. 6 by observing that log A−log B=log(A/B) yields $$\frac{d\log I(\lambda, t)}{dt} \simeq \log\left(\frac{I(t_2, \lambda)}{I(t_1, \lambda)}\right). \quad (7)$$

7. Thus, Eq. 4 can be expressed as $$\frac{\frac{d\log I(\lambda_R)}{dt}}{\frac{d\log I(\lambda_{IR})}{dt}} \simeq \frac{\log\left(\frac{I(t_1, \lambda_R)}{I(t_2, \lambda_R)}\right)}{\log\left(\frac{I(t_1, \lambda_{IR})}{I(t_2, \lambda_{IR})}\right)} = R, \quad (8)$$

where R represents the "ratio of ratios."

8. Solving Eq. 4 for s using the relationship of Eq. 5 yields $$s = \frac{\beta_r(\lambda_R) - R\beta_r(\lambda_{IR})}{R(\beta_o(\lambda_{IR}) - \beta_r(\lambda_{IR})) - \beta_o(\lambda_R) + \beta_r(\lambda_R)}. \quad (9)$$

9. From Eq. 8, R can be calculated using two points (e.g., PPG maximum and minimum), or a family of points. One method applies a family of points to a modified version of Eq. 8. Using the relationship $$\frac{d\log I}{dt} = \frac{dI/dt}{I}, \quad (10)$$

Eq. 8 becomes $$\frac{\frac{d\log I(\lambda_R)}{dt}}{\frac{d\log I(\lambda_{IR})}{dt}} \simeq \frac{\frac{I(t_2, \lambda_R) - I(t_1, \lambda_R)}{I(t_1, \lambda_R)}}{\frac{I(t_2, \lambda_{IR}) - I(t_1, \lambda_{IR})}{I(t_1, \lambda_{IR})}} = \frac{[I(t_2, \lambda_R) - I(t_1, \lambda_R)]I(t_1, \lambda_{IR})}{[I(t_2, \lambda_{IR}) - I(t_1, \lambda_{IR})]I(t_1, \lambda_R)} = R, \quad (11)$$

which defines a cluster of points whose slope of y versus x will give R when $$x = [I(t_2, \lambda_{IR}) - I(t_1, \lambda_{IR})]I(t_1, \lambda_R), \quad (12)$$

and $$y = [I(t_2, \lambda_R) - I(t_1, \lambda_R)]I(t_1, \lambda_{IR}). \quad (13)$$

Once R is determined or estimated, for example, using the techniques described above, the blood oxygen saturation can be determined or estimated using any suitable technique for relating a blood oxygen saturation value to R. For example, blood oxygen saturation can be determined from empirical data that may be indexed by values of R, and/or it may be determined from curve fitting and/or other interpolative techniques.

FIG. 1 is a perspective view of an embodiment of a patient monitoring system 10. System 10 may include sensor unit 12 and monitor 14. In some embodiments, sensor unit 12 may be part of an oximeter. Sensor unit 12 may include an emitter 16 for emitting light at one or more wavelengths into a patient's tissue. A detector 18 may also be provided in sensor unit 12 for detecting the light originally from emitter 16 that emanates from the patient's tissue after passing through the tissue. Any suitable physical configuration of emitter 16 and detector 18 may be used. In an embodiment, sensor unit 12 may include multiple emitters and/or detectors, which may be spaced apart. System 10 may also include one or more additional sensor units (not shown) that may take the form of any of the embodiments described herein with reference to sensor unit 12. An additional sensor unit may be the same type of sensor unit as sensor unit 12, or a different sensor unit type than sensor unit 12. Multiple sensor units may be capable of being positioned at two different locations on a subject's body; for example, a first sensor unit may be positioned on a patient's forehead, while a second sensor unit may be positioned at a patient's fingertip.

Sensor units may each detect any signal that carries information about a patient's physiological state, such as an electrocardiograph signal, arterial line measurements, or the pulsatile force exerted on the walls of an artery using, for example, oscillometric methods with a piezoelectric transducer. According to another embodiment, system 10 may include two or more sensors forming a sensor array in lieu of either or both of the sensor units. Each of the sensors of a sensor array may be a complementary metal oxide semiconductor (CMOS) sensor. Alternatively, each sensor of an array may be charged coupled device (CCD) sensor. In some embodiments, a sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier. It will be understood that any type of sensor, including any type of physiological sensor, may be used in one or more sensor units in accordance with the systems and techniques disclosed herein. It is understood that any number of sensors measuring any number of physiological signals may be used to determine physiological information in accordance with the techniques described herein.

In some embodiments, emitter 16 and detector 18 may be on opposite sides of a digit such as a finger or toe, in which case the light that is emanating from the tissue has passed completely through the digit. In some embodiments, emitter 16 and detector 18 may be arranged so that light from emitter 16 penetrates the tissue and is reflected by the tissue into detector 18, such as in a sensor designed to obtain pulse oximetry data from a patient's forehead.

In some embodiments, sensor unit 12 may be connected to and draw its power from monitor 14 as shown. In another embodiment, the sensor may be wirelessly connected to monitor 14 and include its own battery or similar power supply (not shown). Monitor 14 may be configured to calculate physiological parameters (e.g., pulse rate, blood oxygen saturation, and respiration information) based at least in part on data relating to light emission and detection received from one or more sensor units such as sensor unit 12 and an additional sensor (not shown). In some embodiments, the calculations may be performed on the sensor units or an intermediate device and the result of the calculations may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range. In some embodiments, the system 10 includes a stand-alone monitor in communication with the monitor 14 via a cable or a wireless network link.

In some embodiments, sensor unit 12 may be communicatively coupled to monitor 14 via a cable 24. In some embodiments, a wireless transmission device (not shown) or the like may be used instead of or in addition to cable 24. Monitor 14 may include a sensor interface configured to receive physiological signals from sensor unit 12, provide signals and power to sensor unit 12, or otherwise communicate with sensor unit 12. The sensor interface may include any suitable hardware, software, or both, which may be allow communication between monitor 14 and sensor unit 12.

Patient monitoring system 10 may also include display monitor 26. Monitor 14 may be in communication with display monitor 26. Display monitor 26 may be any electronic device that is capable of communicating with monitor 14 and calculating and/or displaying physiological parameters, e.g., a general purpose computer, tablet computer, smart phone, or an application-specific device. Display monitor 26 may include a display 28 and user interface 30. Display 28 may include touch screen functionality to allow a user to interface with display monitor 26 by touching display 28 and utilizing motions. User interface 30 may be any interface that allows a user to interact with display monitor 26, e.g., a keyboard, one or more buttons, a camera, or a touchpad.

Monitor 14 and display monitor 26 may communicate utilizing any suitable transmission medium, including wireless (e.g., WiFi, Bluetooth, etc.), wired (e.g., USB, Ethernet, etc.), or application-specific connections. In an exemplary embodiment, monitor 14 and display monitor 26 may be connected via cable 32. Monitor 14 and display monitor 26 may communicate utilizing standard or proprietary communications protocols, such as the Standard Host Interface Protocol (SHIP) developed by the assignee. In addition, monitor 14, display monitor 26, or both may be coupled to a network to enable the sharing of information with servers or other workstations (not shown). Monitor 14, display monitor 26, or both may be powered by a battery (not shown) or by a conventional power source such as a wall outlet.

Monitor 14 may transmit calculated physiological parameters (e.g., pulse rate, blood oxygen saturation, and respiration information) to display monitor 26. In some embodiments, monitor 14 may transmit a PPG signal, data representing a PPG signal, or both to display monitor 26, such that some or all calculated physiological parameters (e.g., pulse rate, blood oxygen saturation, and respiration information) may be calculated at display monitor 26. In an exemplary embodiment, monitor 14 may calculate pulse rate and blood oxygen saturation, while display monitor 26 may calculate respiration information such as a respiration rate.

Figure 2:
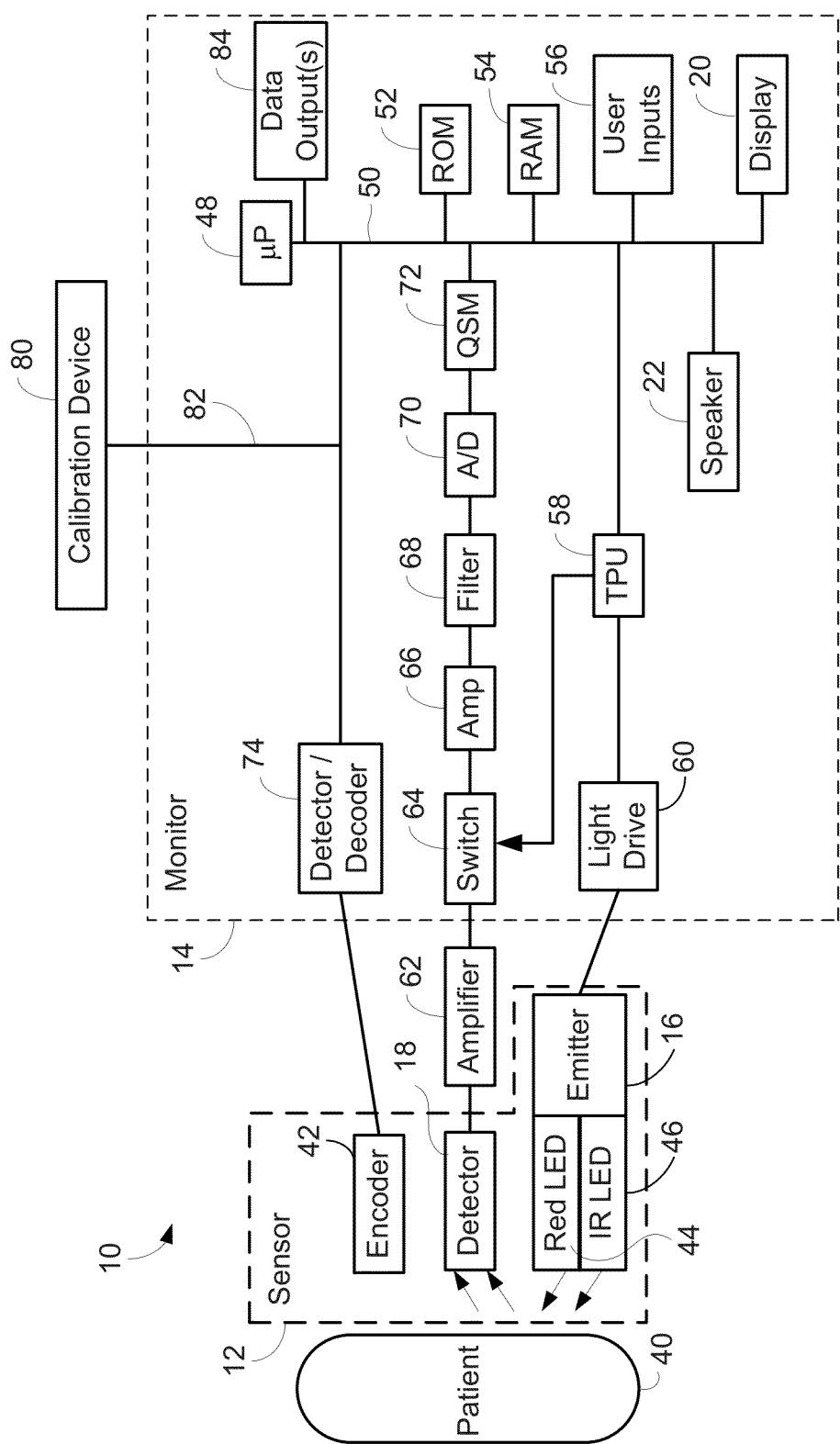
FIG. 2 is a block diagram of the illustrative patient monitoring system of FIG. 1 coupled to a patient in accordance with some embodiments of the present disclosure.

FIG. 2 is a block diagram of a patient monitoring system, such as patient monitoring system 10 of FIG. 1, which may be coupled to a patient 40 in accordance with an embodiment. Certain illustrative components of sensor unit 12 and monitor 14 are illustrated in FIG. 2.

Sensor unit 12 may include emitter 16, detector 18, and encoder 42. In the embodiment shown, emitter 16 may be configured to emit at least two wavelengths of light (e.g., Red and IR) into a patient's tissue 40. Hence, emitter 16 may include a Red light emitting light source such as Red light emitting diode (LED) 44 and an IR light emitting light source such as IR LED 46 for emitting light into the patient's tissue 40 at the wavelengths used to calculate the patient's physiological parameters. In some embodiments, the Red wavelength may be between about 600 nm and about 700 nm, and the IR wavelength may be between about 800 nm and about 1000 nm. In embodiments where a sensor array is used in place of a single sensor, each sensor may be configured to emit a single wavelength. For example, a first sensor may emit only a Red light while a second sensor may emit only an IR light. In a further example, the wavelengths of light used may be selected based on the specific location of the sensor.

It will be understood that, as used herein, the term "light" may refer to energy produced by radiation sources and may include one or more of radio, microwave, millimeter wave, infrared, visible, ultraviolet, gamma ray or X-ray electromagnetic radiation. As used herein, light may also include electromagnetic radiation having any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In some embodiments, detector 18 may be configured to detect the intensity of light at the Red and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the Red and IR wavelengths in the patient's tissue 40.

In some embodiments, encoder 42 may contain information about sensor unit 12, such as what type of sensor it is (e.g., whether the sensor is intended for placement on a forehead or digit) and the wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information about a patient's characteristics may allow monitor 14 to determine, for example, patient-specific threshold ranges in which the patient's physiological parameter measurements should fall and to enable or disable additional physiological parameter algorithms. This information may also be used to select and provide coefficients for equations from which measurements may be determined based at least in part on the signal or signals received at sensor unit 12. For example, some pulse oximetry sensors rely on equations to relate an area under a portion of a PPG signal corresponding to a physiological pulse to determine blood pressure. These equations may contain coefficients that depend upon a patient's physiological characteristics as stored in encoder 42. Encoder 42 may, for instance, be a coded resistor that stores values corresponding to the type of sensor unit 12 or the type of each sensor in the sensor array, the wavelengths of light emitted by emitter 16 on each sensor of the sensor array, and/or the patient's characteristics. In some embodiments, encoder 42 may include a memory on which one or more of the following information may be stored for communication to monitor 14: the type of the sensor unit 12; the wavelengths of light emitted by emitter 16; the particular wavelength each sensor in the sensor array is monitoring; a signal threshold for each sensor in the sensor array; any other suitable information; or any combination thereof.

In some embodiments, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, data output 84, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium that can be used to store the desired information and that can be accessed by components of the system.

In the embodiment shown, a time processing unit (TPU) 58 may provide timing control signals to light drive circuitry 60, which may control when emitter 16 is illuminated and multiplexed timing for Red LED 44 and IR LED 46. TPU 58 may also control the gating-in of signals from detector 18 through amplifier 62 and switching circuit 64. These signals are sampled at the proper time, depending upon which light source is illuminated. The received signal from detector 18 may be passed through amplifier 66, low pass filter 68, and analog-to-digital converter 70. The digital data may then be stored in a queued serial module (QSM) 72 (or buffer) for later downloading to RAM 54 as QSM 72 is filled. In some embodiments, there may be multiple separate parallel paths having components equivalent to amplifier 66, filter 68, and/or A/D converter 70 for multiple light wavelengths or spectra received. Any suitable combination of components (e.g., microprocessor 48, RAM 54, analog to digital converter 70, any other suitable component shown or not shown in FIG. 2) coupled by bus 50 or otherwise coupled (e.g., via an external bus), may be referred to as "processing equipment."

In some embodiments, microprocessor 48 may determine the patient's physiological parameters, such as $SpO_2$, pulse rate, and/or respiration information, using various algorithms and/or look-up tables based on the value of the received signals and/or data corresponding to the light received by detector 18. Signals corresponding to information about patient 40, and particularly about the intensity of light emanating from a patient's tissue over time, may be transmitted from encoder 42 to decoder 74. These signals may include, for example, encoded information relating to patient characteristics. Decoder 74 may translate these signals to enable the microprocessor to determine the thresholds based at least in part on algorithms or look-up tables stored in ROM 52. In some embodiments, user inputs 56 may be used to enter information, select one or more options, provide a response, input settings, any other suitable inputting function, or any combination thereof. User inputs 56 may be used to enter information about the patient, such as age, weight, height, diagnosis, medications, treatments, and so forth. In some embodiments, display 20 may exhibit a list of values, which may generally apply to the patient, such as, for example, age ranges or medication families, which the user may select using user inputs 56.

Calibration device 80, which may be powered by monitor 14 via a communicative coupling 82, a battery, or by a conventional power source such as a wall outlet, may include any suitable signal calibration device. Calibration device 80 may be communicatively coupled to monitor 14 via communicative coupling 82, and/or may communicate wirelessly (not shown). In some embodiments, calibration device 80 is completely integrated within monitor 14. In some embodiments, calibration device 80 may include a manual input device (not shown) used by an operator to manually input reference signal measurements obtained from some other source (e.g., an external invasive or non-invasive physiological measurement system).

Data output 84 may provide for communications with other devices such as display monitor 26 utilizing any suitable transmission medium, including wireless (e.g., WiFi, Bluetooth, etc.), wired (e.g., USB, Ethernet, etc.), or application-specific connections. Data output 84 may receive messages to be transmitted from microprocessor 48 via bus 50. Exemplary messages to be sent in an embodiment described herein may include PPG signals to be transmitted to display monitor module 26.

The optical signal attenuated by the tissue of patient 40 can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. Also, because blood is a fluid, it responds differently than the surrounding tissue to inertial effects, which may result in momentary changes in volume at the point to which the oximeter probe is attached.

Noise (e.g., from patient movement) can degrade a sensor signal relied upon by a care provider, without the care provider's awareness. This is especially true if the monitoring of the patient is remote, the motion is too small to be observed, or the care provider is watching the instrument or other parts of the patient, and not the sensor site. Processing sensor signals (e.g., PPG signals) may involve operations that reduce the amount of noise present in the signals, control the amount of noise present in the signal, or otherwise identify noise components in order to prevent them from affecting measurements of physiological parameters derived from the sensor signals.

Figure 3:
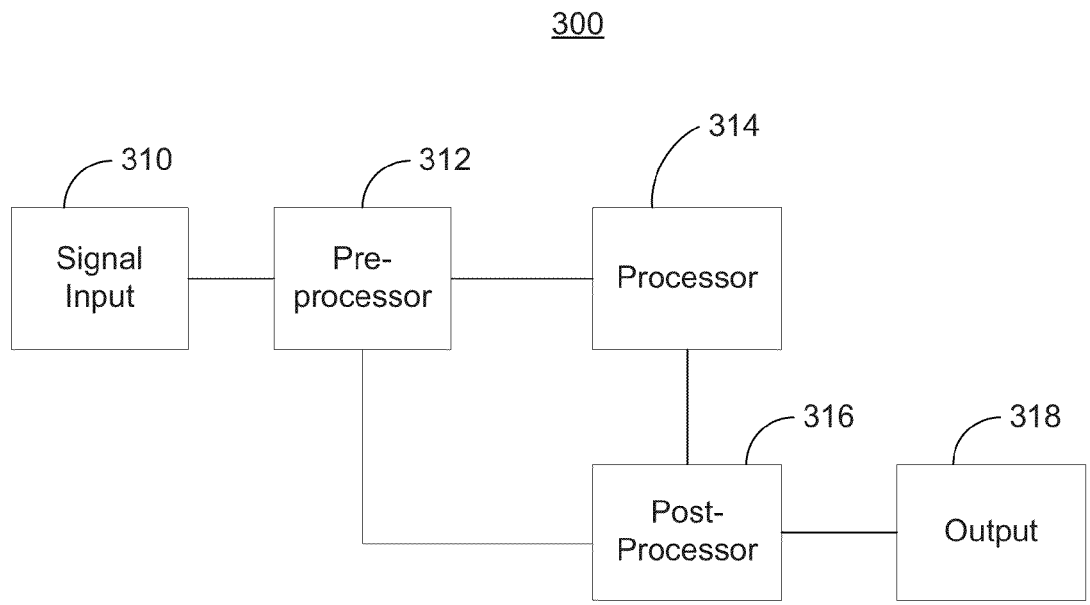
FIG. 3 shows a block diagram of an illustrative signal processing system in accordance with some embodiments of the present disclosure.

FIG. 3 is an illustrative processing system 300 in accordance with an embodiment that may implement the signal processing techniques described herein. In some embodiments, processing system 300 may be included in a patient monitoring system (e.g., patient monitoring system 10 of FIGS. 1-2). Processing system 300 may include input signal 310, pre-processor 312, processor 314, post-processor 316, and output 318. Pre-processor 312, processor 314, and post-processor 316 may be any suitable software, firmware, hardware, or combination thereof for calculating physiological parameters such as respiration information based on input signal 310. For example, pre-processor 312, processor 314, and post-processor 316 may include one or more hardware processors (e.g., integrated circuits), one or more software modules, computer-readable media such as memory, firmware, or any combination thereof. Pre-processor 312, processor 314, and post-processor 316 may, for example, be a computer or may be one or more chips (i.e., integrated circuits). Pre-processor 312, processor 314, and post-processor 316 may, for example, include an assembly of analog electronic components.

In some embodiments, processing system 300 may be included in monitor 14 and/or display monitor 26 of a patient monitoring system (e.g., patient monitoring system 10 of FIGS. 1-2). In the illustrated embodiment, input signal 310 may be a PPG signal. Input signal 310 may be a PPG signal that was sampled and generated at monitor 14, for example at 76 Hz. Input signal 310, pre-processor 312, processor 314, and post-processor 316 may reside entirely within a single device (e.g., monitor 14 or display monitor 26) or may reside in multiple devices (e.g., monitor 14 and display monitor 26).

Input signal 310 may be coupled to pre-processor 312. In some embodiments, input signal 310 may include PPG signals corresponding to one or more light frequencies, such as a Red PPG signal and an IR PPG signal. In some embodiments, the signal may include signals measured at one or more sites on a patient's body, for example, a patient's finger, toe, ear, arm, or any other body site. In some embodiments, signal 310 may include multiple types of signals (e.g., one or more of an ECG signal, an EEG signal, an acoustic signal, an optical signal, a signal representing a blood pressure, and a signal representing a heart rate). The signal may be any suitable biosignal or signals, such as, for example, electrocardiogram, electroencephalogram, electrogastrogram, electromyogram, heart rate signals, pathological sounds, ultrasound, or any other suitable biosignal. The systems and techniques described herein are also applicable to any dynamic signals, non-destructive testing signals, condition monitoring signals, fluid signals, geophysical signals, astronomical signals, electrical signals, financial signals including financial indices, sound and speech signals, chemical signals, meteorological signals including climate signals, any other suitable signal, and/or any combination thereof.

Pre-processor 312 may be implemented by any suitable combination of hardware and software. In an embodiment, pre-processor 312 may be any suitable signal processing device and the signal received from input signal 310 may include one or more PPG signals. An exemplary received PPG signal may be received in a streaming fashion, or may be received on a periodic basis as a sampling window, e.g., every 5 seconds. The received signal may include the PPG signal as well as other information related to the PPG signal, e.g., a pulse found indicator, the mean pulse rate from the PPG signal, the most recent pulse rate, an indicator for the most recent invalid sample, and an indicator of the last artifact for the PPG signal. It will be understood that input signal 310 may include any suitable signal source, signal generating data, signal generating equipment, or any combination thereof to be provided to pre-processor 312. The signal received at input signal 310 may be a single signal, or may be multiple signals transmitted over a single pathway or multiple pathways.

Pre-processor 312 may apply one or more signal processing operations to input signal 310. For example, pre-processor 312 may apply a pre-determined set of processing operations to input signal 310 to produce a signal that may be appropriately analyzed and interpreted by processor 314, post-processor 316, or both. Pre-processor 312 may perform any necessary operations to provide a signal that may be used as an input for processor 314 and post-processor 316 to determine physiological information such as respiration information. Examples include reshaping the signal for transmission, multiplexing the signal, modulating the signal onto carrier signals, compressing the signal, encoding the signal, filtering the signal, low-pass filtering, band-pass filtering, signal interpolation, downsampling of a signal, attenuating the signal, adaptive filtering, closed-loop filtering, any other suitable filtering, and/or any combination thereof.

Other signal processing operations may be performed by pre-processor 312 for each pulse and may be related to producing morphology metrics suitable as inputs to determine physiological information. Pre-processor 312 may perform calculations based on an analysis window of a series of recently received PPG signal sampling windows, e.g., a 45-second analysis window may correspond to the 9 most recent 5-second sampling windows. The physiological information may be respiration information, which may include any information relating to respiration, e.g., respiration rate, change in respiration rate, breathing intensity, etc. Because respiration has an impact on pulse characteristics, it may be possible to determine respiration information from a PPG signal. Morphology metrics may be parameters that may be calculated from the PPG signal that provide information related to respiration. Examples include a down metric for a pulse, kurtosis for a pulse, the delta of the second derivative between consecutive pulses, the up metric for a pulse, skew, b/a ratio, c/a ratio, peak amplitude of a pulse, center of gravity of a pulse, or area of a pulse, as described in more detail herein. Other information that may be determined by pre-processor 312 may include the pulse rate, the variability of the period of the PPG signal, the variability of the amplitude of the PPG signal, and an age measurement indicative of the age of the useful portion of the analyzed PPG signal.

In some embodiments, pre-processor 312 may be coupled to processor 314 and post-processor 316. Processor 314 and post-processor 316 may be implemented by any suitable combination of hardware and software. Processor 314 may receive physiological information and calculated parameters from pre-processor 312. For example, processor may receive morphology metrics for use in calculating morphology metric signals that may be used to determine respiration information, as well as pulse rate and an age for the morphology metric signals. For example, processor 314 may receive samples representing a number of morphology metric values, such as down metric calculations, kurtosis metric calculations, and delta of the second derivative (DSD) metric calculations from pre-processor 312. Processor 314 may utilize the received morphology metric values to calculate morphology metric signals and then to calculate respiration information signals and values from the morphology metric signals. Processor 314 may be coupled to post-processor 316 and may communicate respiration information to post-processor 316. Processor 314 may also provide other information to post-processor 316 such as the signal age related to the signal used to calculate the respiration information, and a time ratio representative of the useful portion of the respiration information signal. Pre-processor 312 may also provide information to post-processor 316 such as period variability, amplitude variability, and pulse rate information. Post-processor 316 may utilize the received information to calculate an output respiration information, as well as other information such as the age of the respiration information and status information relating to the respiration information output, e.g., whether a valid output respiration information value is currently available. Post-processor 316 may provide the output information to output 318.

Output 318 may be any suitable output device such as one or more medical devices (e.g., a medical monitor that displays various physiological parameters, a medical alarm, or any other suitable medical device that either displays physiological parameters or uses the output of post-processor 316 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

In some embodiments, all or some of pre-processor 312, processor 314, and/or post-processor 316 may be referred to collectively as processing equipment. For example, processing equipment may be configured to amplify, filter, sample and digitize an input signal 310 and calculate physiological information from the signal.

Pre-processor 312, processor 314, and post-processor 316 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by pre-processor 312, processor 314, and post-processor 316 to, for example, store data relating to input PPG signals, morphology metrics, respiration information, or other information corresponding to physiological monitoring.

It will be understood that system 300 may be incorporated into system 10 (FIGS. 1 and 2) in which, for example, input signal 310 may be generated by sensor unit 12 (FIGS. 1 and 2) and monitor 14 (FIGS. 1 and 2). Pre-processor 312, processor 314, and post-processor 316 may each be located in one of monitor 14 or display monitor 26 (or other devices), and may be split among multiple devices such as monitor 14 or display monitor 26. In some embodiments, portions of system 300 may be configured to be portable. For example, all or part of system 300 may be embedded in a small, compact object carried with or attached to the patient (e.g., a watch, other piece of jewelry, or a smart phone). In some embodiments, a wireless transceiver (not shown) may also be included in system 300 to enable wireless communication with other components of system 10 (FIGS. 1 and 2). As such, system 10 (FIGS. 1 and 2) may be part of a fully portable and continuous patient monitoring solution. In some embodiments, a wireless transceiver (not shown) may also be included in system 300 to enable wireless communication with other components of system 10. For example, communications between one or more of pre-processor 312, processor 314, and post-processor 316 may be over BLUETOOTH, 802.11, WiFi, WiMax, cable, satellite, Infrared, or any other suitable transmission scheme. In some embodiments, a wireless transmission scheme may be used between any communicating components of system 300.

Pre-processor 312 may determine the locations of pulses within a periodic signal (e.g., a PPG signal) using a pulse detection technique. For ease of illustration, the following pulse detection techniques will be described as performed by pre-processor 312, but any suitable processing device may be used to implement any of the techniques described herein.

Figure 4:
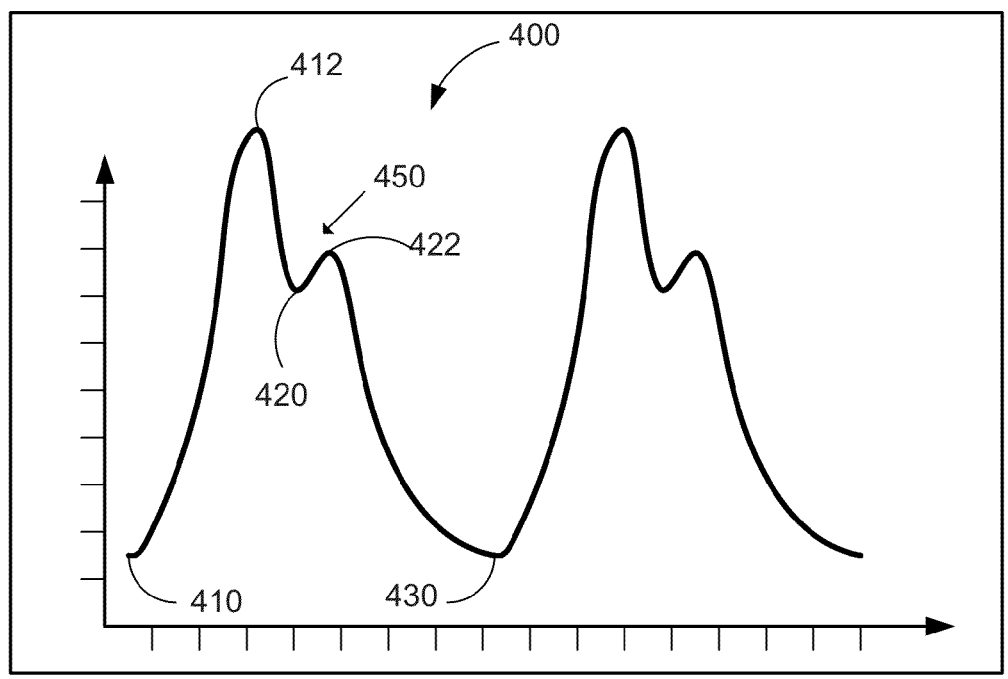
FIG. 4 shows an illustrative PPG signal that may be analyzed in accordance with some embodiments of the present disclosure.

An illustrative PPG signal 400 is depicted in FIG. 4. Pre-processor 312 may receive PPG signal 400 from input signal 310, and may identify reference points such as local minimum point 410, local maximum point 412, local minimum point 420, local maximum point 422, and local minimum point 430 in the PPG signal 400. Processor 312 may pair each local minimum point with an adjacent maximum point. For example, processor 312 may pair points 410 and 412 to identify one segment, points 412 and 420 to identify a second segment, points 420 and 422 to identify a third segment and points 422 and 430 to identify a fourth segment. The slope of each segment may be measured to determine whether the segment corresponds to an upstroke portion of the pulse (e.g., a positive slope) or a downstroke portion of the pulse (e.g., a negative slope) portion of the pulse. A pulse may be defined as a combination of at least one upstroke and one downstroke.

For example, the segment identified by points 410 and 412 and the segment identified by points 412 and 430 may define a pulse. Any suitable points (e.g., maxima, minima, zeros) or features (e.g., pulse waves, notches, upstrokes) of a physiological signal may be identified by processor 312 as reference points.

PPG signal 400 may include a dichrotic notch 450 or other notches (not shown) in different sections of the pulse (e.g., at the beginning (referred to as an ankle notch), in the middle (referred to as a dichrotic notch), or near the top (referred to as a shoulder notch)). Notches (e.g., dichrotic notches) may refer to secondary turning points of pulse waves as well as inflection points of pulse waves. Pre-processor 312 may identify notches and either utilize or ignore them when detecting the pulse locations. In some embodiments, pre-processor 312 may compute the second derivative of the PPG signal to find the local minima and maxima points and may use this information to determine a location of, for example, a dichrotic notch. Additionally, pre-processor 312 may interpolate between points in a signal or between points in a processed signal using any interpolation technique (e.g., zero-order hold, linear interpolation, and/or higher-order interpolation techniques). Some pulse detection techniques that may be performed by pre-processor 312 are described in more detail in co-pending, commonly assigned U.S. patent application Ser. No. 12/242,908, filed Sep. 30, 2008 and entitled "SYSTEMS AND METHODS FOR DETECTING PULSES IN A PPG SIGNAL," which is incorporated by reference herein in its entirety.

In some embodiments, reference points may be received or otherwise determined from any other suitable pulse detecting technique. For example, pulse beep flags generated by a pulse oximeter, which may indicate when the pulse oximeter is to emit an audible beep, may be received by processor 314, pre-processor 312, post-processor 316, or any combination thereof for processing in accordance with the present disclosure. The pulse beep flags may be used as reference points indicative of the occurrence of a pulses in temporally corresponding places in the associated PPG signal.

Figure 5:
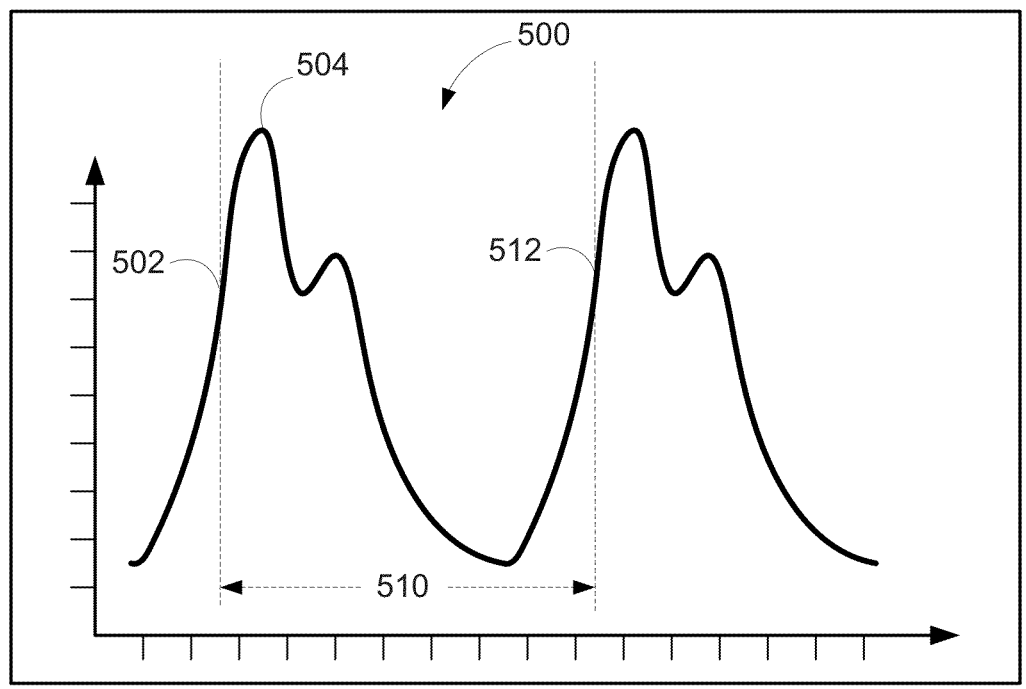
FIG. 5 shows an illustrative signal that may be analyzed in accordance with some embodiments of the present disclosure.
Figure 6:
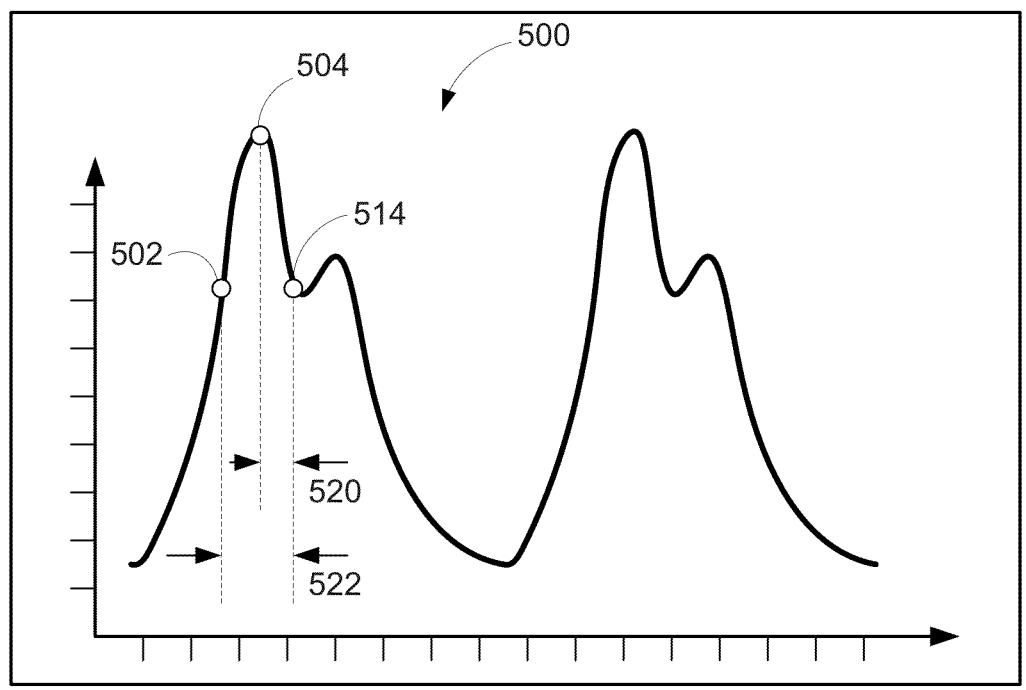
FIG. 6 shows the illustrative signal of FIG. 5 including illustrative fiducial points in accordance with some embodiments of the present disclosure.

An illustrative PPG signal 500 is depicted in FIG. 5. FIG. 6 shows the illustrative signal of FIG. 5 including further analysis. Processor 314 may receive PPG signal 500, and may locate successive reference points 502 and 512 corresponding to respective, successive pulse waves. In some embodiments, reference points may be, for example, maxima in the first derivative of PPG signal 500, as illustrated in FIG. 5 by reference points 502 and 512. Interval 510, between reference points 502 and 512, may correspond to the duration of a pulse wave. For example, the inverse of interval 510 may be proportional to a pulse rate (e.g., in units of beats per minute (BPM) or Hz).

In some embodiments, pre-processor 312 (or any other suitable processor) may locate a fiducial point at point 514 for further calculations based on a reference point. For example, using point 502 as a reference point, pre-processor 312 may locate point 514 by translating a particular time (or corresponding number of samples) from point 502 in a particular direction along PPG signal 500, as shown by time interval 522 of FIG. 6. Another exemplary reference point may be a maximum point 504 within interval 510. In some embodiments, processor 312 may use point 504 as a reference point to locate a further fiducial point at point 514, as shown in FIG. 6. For example, using point 504 as a reference point, processor 312 may locate point 514 by translating a particular time (or corresponding number of samples) from point 504 in a particular direction along PPG signal 500, as shown by time interval 520 of FIG. 6. Point 514 may be a fiducial point, and may be used in further physiological calculations. The number of samples defining a fiducial point from a reference point (or any other suitable point derived from the PPG signal or from the reference point) may be determined according to, for example, empirical analysis. In some embodiments, the fiducial point may be the same as a reference point (i.e., once a reference point is determined, no additional processing is necessary to identify a corresponding fiducial point).

Respiratory activities may cause particular changes in the morphology of a PPG signal throughout a respiratory cycle, including, for example, on a pulse by pulse basis. In some circumstances, these changes in morphology may be in addition to morphological change due to changes in stroke volume, pulse rate, blood pressure, any other suitable physiological parameters, or any combination thereof. Respiratory modulations may include baseline modulations, amplitude modulations, frequency modulations, respiratory sinus arrhythmia, any other suitable modulations, or any combination thereof. Respiratory modulations may exhibit different phases, amplitudes, or both, within a PPG signal and may contribute to complex behavior (e.g., changes) of the PPG signal. Morphology metrics may be calculated on any portion of a PPG signal, but in one exemplary embodiment each consecutive set of fiducial points may define a relevant portion of the PPG signal for calculating a morphology metric, and may be referred to herein as a fiducial-defined portion.

In some embodiments, a set of fiducial points on a sampled physiological signal or signal derived thereof (e.g., a derivative of a signal, a smoothed signal, a filtered signal, an amplified signal, or other processed signal) may be further processed (e.g., by pre-processor 312). In some embodiments, a set of fiducial points, corresponding to a subset of points on the sampled signal, may be used to create a fiducial signal or as a reference to calculate morphology metric values. For example, a single point on each pulse wave may be used to create the fiducial signal or as a basis for calculating a morphology metric value associated with a fiducial defined portion. The fiducial signal may be further analyzed to, for example, calculate physiological parameters (e.g., respiration information), signal quality metrics, any other suitable values, or any combination thereof, e.g., by processor 314 and post-processor 316.

In an illustrative example, in some embodiments, a set of fiducial points on a PPG signal (e.g., a collection of points of successive pulse waves each similar to point 514 of FIG. 6) may be outputted as a fiducial signal. In another illustrative example, a set of fiducial points on a PPG signals may be utilized as a basis to determine one or more sets of morphology metric values. The resulting fiducial signal or morphology metric values may be further processed to calculate respiration rate, respiratory modulation metrics, any other suitable respiration information, any other suitable physiological parameters, any other suitable metrics, or any combination thereof.

The selection of fiducial points may influence processing of the fiducial signal or morphology metric values. In some embodiments, selection of fiducial points may be optimized to enhance the performance of an analysis applied to the fiducial signal or morphology metric values. For example, a PPG signal may be pre-processed to emphasize key morphological changes, which may aid in the extraction of respiratory information using further processing (e.g., using an autocorrelation or wavelet transform). Pre-processing may include generating derived signals such as, for example, derivative, integral, or moving averaged signals, which may be more amenable to particular analysis in some circumstances. Pre-processing may also include determining one or more reference points, determining one or more fiducial points, or both.

Figure 7:
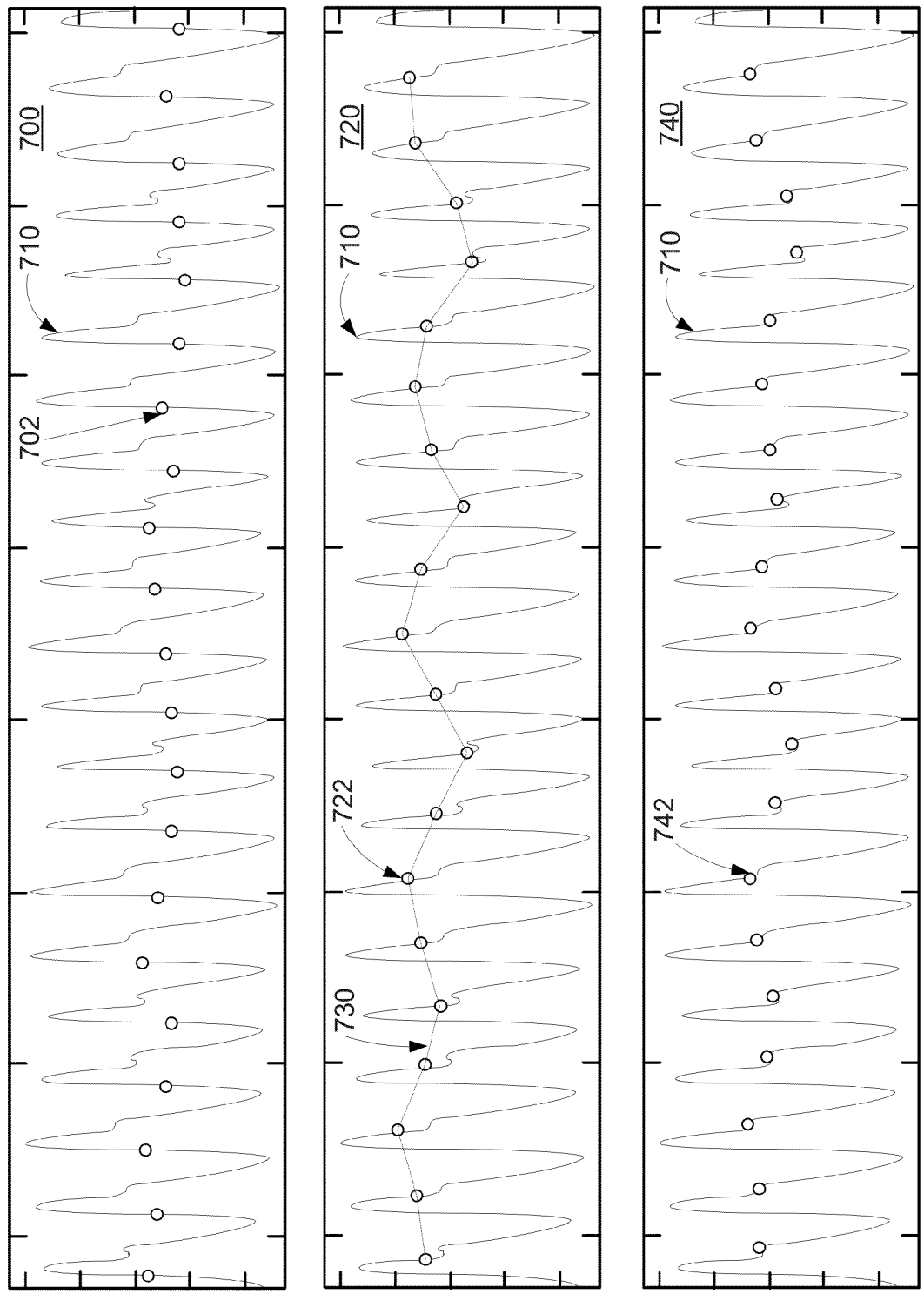
FIG. 7 shows illustrative graphs depicting a PPG signal from which fiducial points may be derived in accordance with some embodiments of the present disclosure.

FIG. 7 shows illustrative graphs 700, 720, and 740 depicting determining fiducial points from a PPG signal. Each of graphs 700, 720, and 740 include illustrative time series 710 shown by a solid line, and a set of points shown by a set of circles. The abscissa of graphs 700, 720, and 740 are in units of time, while the ordinate of graphs 700, 720, and 740 are in units of signal amplitude.

Time series 710 shows a series of pulse waves of an illustrative PPG signal. The set of points 702 represented by circles in graph 700 correspond to the peak in the first derivative of each pulse wave. In some embodiments, the set of points 702 may be used as reference points, fiducial points, or both. In the illustrated embodiment, the set of points 702 represents a set of reference points. Although points 702 correspond to the peak of the first derivative of each pulse wave, other reference points may utilized, such as the maximum amplitude of each pulse wave.

The set of points 722 represented by circles in graph 720 correspond to points 16 samples (i.e., about 210 milliseconds at a sampling rate of about 76 Hertz) to the right of the peak in the first derivative of each pulse wave (i.e., points 702). The set of points 722 may be a set of fiducial points, selected using the peaks in the first derivative of each pulse wave as reference points and locating a set of respective points spaced from the reference points by a particular time interval. Time series 730, including the set of points 722, represents a "fiducial signal" derived from time series 720. Fiducial points 722 may also be utilized to determine other parameters, such as determining one or more morphology metrics as described herein.

The set of points 742 represented by circles in graph 740 correspond to points 22 samples to the right of the peak in the first derivative of each pulse wave. The set of points 742 may be a set of fiducial points, selected using the peaks in the first derivative of each pulse wave as reference points and locating a set of respective points spaced from the reference points by a particular time interval. Although not depicted herein, the fiducial points defined by the set of points 742 may be utilized to determine a fiducial signal, determine morphology metrics, or other parameters as described herein. Fiducial points may also be located at other locations relative to the reference points.

In some embodiments, processor 314 or post-processor 316 may utilize fiducial points 722 or 742 as a basis for determining morphology metrics as described herein to determine physiological information. Time series 730 may also be processed to determine physiological information. For example, processor 314 or post-processor 316 may determine respiration information such as a respiration rate from morphology metrics based on fiducial points 722 or 742, or from time series 730. For example, respiratory activity may be observed by the oscillatory character (at a longer time scale than that of the pulse rate shown by time series 710) of time series 730. Respiration information (e.g., respiration rate, respiration modulation shape) may be calculated by processor 314 or post-processor 316 using any suitable mathematical processing techniques (e.g., using wavelet transforms, spectral transforms, curve-fitting). In some embodiments, a particular set of points (e.g., the set of points 722 located about 210 milliseconds to the right of the peak in first derivative) may allow processor 314, post-processor 316, or both to calculate physiological information with relatively more accuracy, relatively less computational requirements, relatively more consistency, any other suitable relative computational advantage, or any combination thereof.

Figure 8:
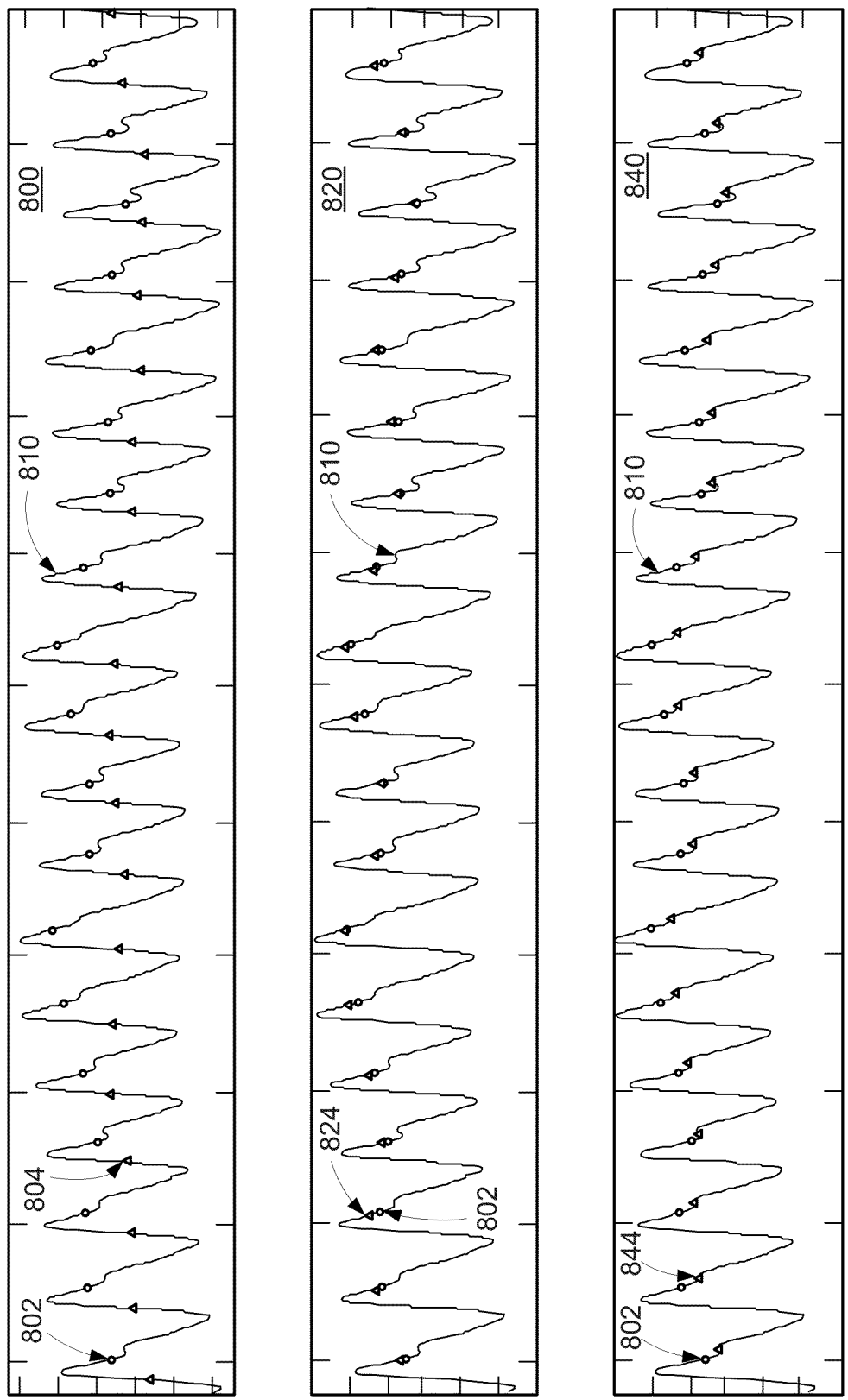
FIG. 8 shows illustrative graphs depicting a PPG signal from which reference points and fiducial points may be derived in accordance with some embodiments of the present disclosure.

FIG. 8 shows a PPG signal from which reference points and fiducial points may be derived as illustrated in graphs 800. Each graph includes a time series of an illustrative PPG signal shown by a solid line, a first set of points shown by triangles, and a second set of points shown by circles. The abscissa of each graph is in units of time, while the ordinate of each graph is in units of signal amplitude.

Time series 810 includes a series of pulse waves of an illustrative PPG signal. The set of points 804 represented by triangles in graph 800 correspond to the peak in the first derivative of each pulse wave. Although points 804 correspond to the peak of the first derivative of each pulse wave, other reference points may utilized, such as the maximum amplitude of each pulse wave. The set of points 802 represented by circles correspond to illustrative reference points (e.g., reference points indicating "pulse found"). Any suitable technique may be used to identify pulses in a PPG, including any known techniques or any future techniques currently not known.

The set of points 824 represented by triangles in graph 820 correspond to points located 14 samples (about 184 ms at a 76 Hz sampling rate) to the right of (i.e., after) the reference points of each pulse wave (i.e., peak in the first derivative points 804). The set of points 824 are roughly coincident with the set of points 802. In some embodiments, the set of points 824 may be used as a set of fiducial points, rather than locating the set of points 802. For example, pre-processor 312 may use the set of points 824 to indicate where a pulse has been detected. The use of the set of points 824 may allow processing system 300 to calculate physiological information with relatively more accuracy, relatively less computational requirements, relatively more consistency, any other suitable relative computational advantage, or any combination thereof. In some circumstances, the set of points 824 may be preferred to the set of points 802 because the set of points 824 are derived from the morphology of the signal and may be in phase with the morphology of the signal. In some circumstances, the set of points 802 may be dependent on the manner that location is determined, and the use of the set of points 824 may provide an improvement.

The set of points 844 represented by triangles in graph 840 corresponds to points located 22 samples to the right of the reference points of each pulse wave (i.e., peak in the first derivative points 804). The set of points represented by circles 802 corresponds to the same reference points of graph 800. In some embodiments, processor 312 may determine that the set of points 844 is not to be used as a set of fiducial points because, for example, the set of points 844 is not substantially coincident with the set of points 802.

FIG. 9 is flow diagram 900 showing illustrative steps for determining physiological information, in accordance with the present disclosure.

Step 902 may include pre-processor 312 determining one or more reference points of a physiological signal. Determining the one or more reference points of the physiological signal may include receiving the physiological signal from a sensor, conditioning the physiological signal (e.g., amplifying, filtering, sampling, digitizing), performing calculations on the physiological signal or conditioned signal thereof, selecting a time interval (or a corresponding number of samples) of the physiological signal or conditioned signal thereof to analyze, any other suitable processing, or any combination thereof. In some embodiments, a single reference point on a signal may be determined by pre-processor 312 such as, for example, an absolute minimum or maximum of a signal. In some embodiments, a set of reference points may be determined by pre-processor 312. For example, pre-processor 312 may be configured to process a PPG signal that includes a set of pulse waves, and determine a reference point for each pulse wave. Reference points on a signal may include minimums on the signal, maximums on the signal, zeros on the signal, minimums on a derivative (of any suitable order) of the signal, maximums on a derivative (of any suitable order) of the signal, zeros on a derivative (of any suitable order) of the signal, any other suitable points on a signal or other signal derived thereof, or any combination thereof. For example, pre-processor 312 may determine two reference points, which may be maxima in the first derivative of two successive pulse waves of a PPG signal. In a further example, pre-processor 312 may determine a reference point, which may be a maximum or a minimum of the first derivative of a single pulse wave of a PPG signal. In a further example, pre-processor 312 may determine a reference point, which may be a maximum of a pulse wave of a PPG signal.

Step 904 may include pre-processor 312 determining one or more fiducial points on the physiological signal of step 902 using the one or more reference points of step 902. Determining the one or more fiducial points of the physiological signal may include using a time interval relative to the one or more particular reference points of step 902, using a number of samples relative to the one or more particular reference points of step 902, any other suitable approaches of determining a location of one or more fiducial points on a signal, or any combination thereof. For example, determining a fiducial point may include locating a point on the physiological signal at a particular time interval or number of samples from a reference point.

Step 906 may include pre-processor 312 determining physiological information based at least in part on the determined one or more fiducial points of step 904. Determining physiological information may include performing calculations directly on the one or more fiducial points, generating morphology metric values and signals based on the fiducial points, generating a fiducial signal based on the one or more fiducial points, performing calculations on the morphology metric values or fiducial signal, calculating one or more physiological parameters (e.g., pulse rate, respiration rate, $SpO_2$, blood pressure), any other suitable processing to determine physiological information, or any combination thereof. In some embodiments, a pre-constructed program may be executed by processing system 300 to determine physiological information from one or more fiducial points. For example, a program executed by pre-processor 312 may take as inputs a set of fiducial points and calculate one or more sets of morphology metric values. Pre-processor 312 may derive morphology metric signals from the morphology metric values and processor 314 or post-processor 316 may determine respiration information such as respiration rate from the morphology metric values, e.g., by applying a continuous wavelet transform on a combined autocorrelation of the morphology metric signals. The transform may yield a dominant component (e.g., a particular scale in the wavelet domain), which may indicate a rate of an oscillatory physiological activity, such as a respiration rate. In a further example, a program executed by pre-processor 312 may take as inputs a set of fiducial points represented by a new time series. The program may determine one or more fiducial points of the new time series such as, for example, the peak to peak time interval of the fiducial signal, which may yield physiological information such as respiration rate. Processing system 300 may determine physiological information by performing any suitable calculation, executing any suitable analysis or program, performing any suitable database search, any other suitable steps, or any combination thereof.

In some embodiments, determining the one or more fiducial points of the physiological signal may include pre-processor 312 accessing fiducial information, as shown by step 908. Accessing fiducial information may include recalling a mathematical expression, accessing a database (e.g., a look up table), accessing memory, using a pre-set approach for determining fiducial points, receiving a user input selecting an approach for determining fiducial points, any other suitable accessing of stored information, any other suitable accessing of user inputted information, or any combination thereof. For example, step 908 may include using a physiological parameter value in a lookup table to determine a fiducial point type, a fiducial point location, or other suitable fiducial information. In a further example, step 908 may include inputting a physiological parameter value such as a pulse rate into a mathematical formula, which may output a fiducial point location relative to a reference point (e.g., a time interval or number of sample), or other suitable fiducial information.

FIG. 10 is flow diagram 1000 showing illustrative steps for determining respiratory information, in accordance with the present disclosure.

Step 1002 may include pre-processor 312 locating two reference points of a PPG signal. Locating the two reference points of the PPG signal may include determining a minimum, maximum, zero, any other suitable points on a signal or other signal derived thereof (e.g., a derivative of any suitable order), or any combination thereof. For example, the two reference points may be two successive maxima in the first derivative of the PPG signal. In a further example, the two reference points may be a successive maximum and a minimum of the first derivative of the PPG signal.

Step 1004 may include pre-processor 312 locating a maximum on the PPG signal between the two located reference points of step 1002. In some embodiments, pre-processor 312 may locate a single maximum signal value between the two reference points. For example, the two reference points may be successive maxima in the first derivative of the PPG signal, and the maximum on the PPG signal may correspond to a peak of a portion of the PPG signal (e.g., as shown by point 504 of FIG. 5). In a further example, the two reference points may be a maximum and a minimum of the first derivative of the PPG signal (e.g., corresponding to a respective upstroke and downstroke of a pulse wave), and the maximum may correspond to a peak of a portion of the PPG signal.

Step 1006 may include pre-processor 312 selecting a fiducial point of the PPG signal. In some embodiments, pre-processor 312 may select a fiducial point located a particular time interval (or corresponding number of samples) from the located maximum of step 1004. For example, pre-processor 312 may select a fiducial point located about 210 milliseconds (approximately 16 samples at a sampling rate of about 76 Hertz) to the right of the located maximum of step 1004. In some embodiments, the particular time interval may depend on physiological information (e.g., the patient's pulse rate, respiration rate, physiological history), and need not be a fixed interval. For example, the particular time interval may be the period corresponding to 10% of the average or instantaneous pulse period of the patient (e.g., 100 milliseconds for a pulse period of 1 second). In a further example, the particular time interval may be based at least in part on previously calculated respiration information such as respiration rate (e.g., using a look up table of various calculated respiration rates to find an optimum time interval). In some embodiments, pre-processor 312 may select multiple fiducial points. In some embodiments, pre-processor 312 may perform steps 1002 and 1004 repeatedly, locating a set of maxima between a corresponding set of pairs of reference points. A set of corresponding fiducial points may then be selected. For example, a fiducial point may be selected for each reference point of a PPG signal, resulting in a set of fiducial points.

In some embodiments, selecting the fiducial point of step 1006 may include pre-processor 312 accessing fiducial information, as shown by step 1010. Accessing fiducial information may include recalling a mathematical expression, accessing a database, accessing memory, using a pre-set approach for determining fiducial points, receiving a user input selecting an approach for determining fiducial points, any other suitable accessing of stored information, any other suitable accessing of user inputted information, or any combination thereof.

Step 1008 may include processing system 300 determining respiratory information based at least in part on the selected fiducial point of step 1006. Respiratory information may include respiration rate, respiratory modulation shape, any other suitable information, or any combination thereof. Processor 314 or post-processor 316 may determine respiratory information by calculating the peak to peak time interval of a set of selected fiducial points, generating morphology metric signals based on fiducial points, performing an autocorrelation of the set of selected fiducial points or morphology metric signals and determining one or more peaks, performing a transform (e.g., a wavelet transform, a Fourier transform) on the set of selected fiducial points, morphology metric signals, or autocorrelation sequences, performing any other suitable calculation, or any combination thereof.

FIG. 11 is flow diagram 1100 showing illustrative steps for generating a fiducial signal from a physiological signal, in accordance with the present disclosure.

Step 1102 may include pre-processor 312 locating two reference points of a PPG signal. Locating the two reference points of the PPG signal may include determining a minimum, maximum, zero, any other suitable points on a signal or other signal derived thereof (e.g., a derivative of any suitable order), or any combination thereof. For example, the two reference points may be two successive maxima in the first derivative of the PPG signal. In a further example, the two reference points may be a successive maximum and a minimum of the first derivative of the PPG signal.

Step 1104 may include pre-processor 312 locating a maximum on the PPG signal between the two located reference points of step 1102. In some embodiments, pre-processor 312 may locate a single maximum between the two reference points. For example, the two reference points may be successive maxima in the first derivative of the PPG signal, and the maximum on the PPG signal may correspond to peak of a portion of the PPG signal (e.g., as shown by point 504 of FIG. 5). In a further example, the two reference points may be a successive maximum and a minimum of the first derivative of the PPG signal, and the maximum on the PPG signal may correspond to a peak of a portion of the PPG signal.

Step 1106 may include pre-processor 312 selecting a fiducial point of the PPG signal. In some embodiments, pre-processor 312 may select a fiducial point located a particular time interval (or corresponding number of samples) from the located maximum of step 1104. For example, pre-processor 312 may select a fiducial point located about 210 milliseconds (approximately 16 samples at a sampling rate of about 76 Hertz) to the right of the located maximum of step 1104. In some embodiments, the particular time interval may depend on physiological information, and need not be a fixed interval. For example, the particular time interval may be the period corresponding to 10% of the average or instantaneous heart rate of the patient. In a further example, the particular time interval may be based at least in part on previously calculated respiration information. In some embodiments, pre-processor 312 may select a set of fiducial points. In some embodiments, pre-processor 312 may perform steps 1102 and 1104 repeatedly, locating a set of maxima between a corresponding set of pairs of reference points. A set of corresponding fiducial points may then be selected. For example, a fiducial point may be selected on each pulse wave of a set of pulse waves of a PPG signal, resulting in a set of fiducial points.

In some embodiments, selecting the fiducial point of step 1106 may include pre-processor 312 accessing fiducial information, as shown by step 1110. Accessing fiducial information may include recalling a mathematical expression, accessing a database, accessing memory, using a pre-set approach for determining fiducial points, receiving a user input selecting an approach for determining fiducial points, any other suitable accessing of stored information, any other suitable accessing of user inputted information, or any combination thereof.

Step 1108 may include processing system 300 generating a fiducial signal based at least in part on the selected fiducial point of step 1106. In some embodiments the fiducial signal includes a set of selected fiducial points (e.g., as shown by time series 730 of FIG. 7). At step 1108, processing system 300 may average, filter, output (e.g., via a communications interface), store in memory, or otherwise process, the fiducial signal. In some embodiments, physiological calculation may be performed using the fiducial signal of step 1108.

Figure 12:
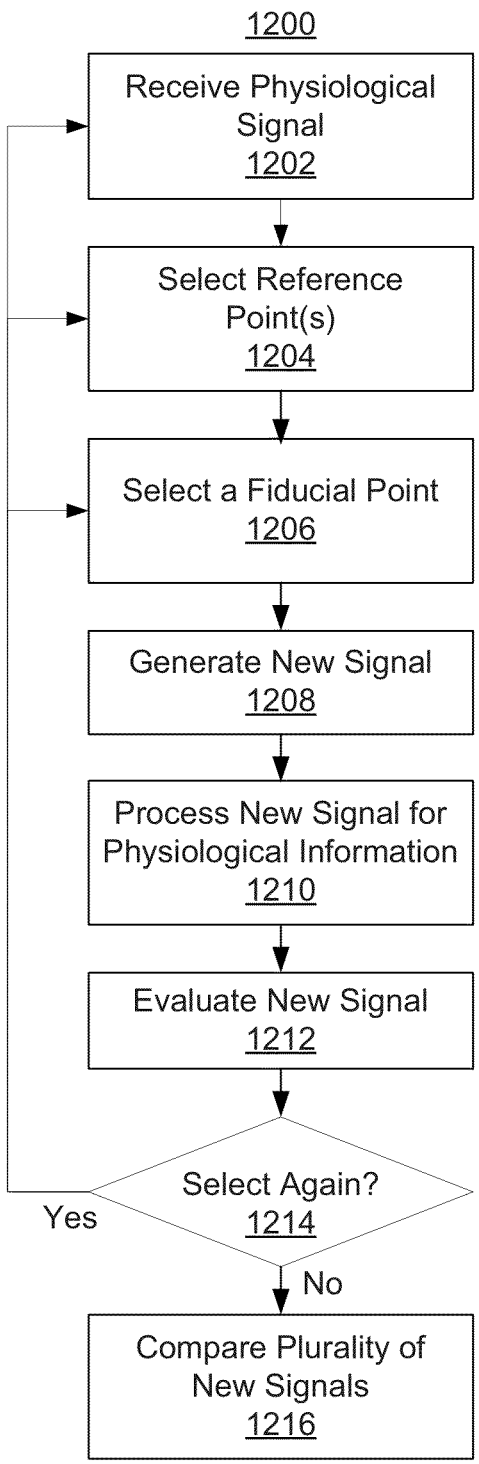
FIG. 12 is flow diagram showing illustrative steps for analyzing fiducial signals generated according to the steps of, for example, FIG. 11 in accordance with some embodiments of the present disclosure.

FIG. 12 is flow diagram 1200 showing illustrative steps for evaluating a set of fiducial signals, in accordance with the present disclosure.

Step 1202 may include pre-processor 312 receiving a physiological signal. In some embodiments, the physiological signal may be received by pre-processor 312 as input signal 310 from one or more physiological sensors (e.g., PPG sensors). In some embodiments, the physiological signal may have been stored in memory (e.g., ROM 52 or RAM 54 of FIG. 2), and may be recalled by pre-processor 312 from the memory. Step 1202 may include conditioning the physiological signal such as, for example, amplifying, filtering, baseline subtracting, sampling, digitizing, outputting input signal 310 to pre-processor 312, performing any other signal conditioning, or any combination thereof. In some embodiments, step 1202 may include pre-processor 312 calculating a derivative of the physiological signal, averaging the physiological signal (e.g., time averaging, ensemble averaging), subtracting two physiological signals to produce a single signal (e.g., subtracting noise background), calculating a ratio of two physiological signals to produce a single signal, performing any other suitable calculation, or any combination thereof.

Step 1204 may include pre-processor 312 selecting one or more reference points of a physiological signal as described above. Step 1206 may include pre-processor 312 selecting one or more fiducial points on the physiological signal of step 1202, using the one or more reference points of step 1204 as described above. Step 1208 may include pre-processor 312 generating a fiducial signal based at least in part on the selected fiducial points of step 1206. In some embodiments the fiducial signal includes a set of selected fiducial points (e.g., as shown by time series 730 of FIG. 7). At step 1208, pre-processor 312 may average, filter, output (e.g., via a communications interface), store in memory, or otherwise process, the fiducial signal.

Step 1210 may include processing system 300 processing the fiducial signal of step 1208 for physiological information. In some embodiments, step 1210 may include processor 314, post-processor 316, or both determining a physiological parameter such as, for example, pulse rate, respiration rate, blood pressure, any other suitable physiological parameter, or any combination thereof. In some embodiments, step 1210 may include processor 314, post-processor 316, or both determining a signal metric such as, for example, an amplitude, a phase difference, an offset, a signal to noise ratio, any other suitable signal metric of the fiducial signal, or any combination thereof. In some embodiments, step 1210 may include processor 314, post-processor 316, or both storing a physiological parameter value, signal metric, or both, in memory.

Step 1212 may include processor 314, post-processor 316, or both evaluating the fiducial signal generated at step 1208 based at least in part on the processed physiological information of step 1210. In some embodiments, the physiological information of step 1210 may be compared with reference physiological information (e.g., that may be stored in memory, or provided by an independent monitoring device) to determine a difference in values. For example, a time series of physiological parameters may be calculated at step 1210 and may be compared with a reference time series to determine a root mean square deviation (RMSD). The output of step 1212 may be a single metric (e.g., a RMSD value, a confidence value), a set of metrics (e.g., an array of differences), a qualitative indicator (e.g., a discriminant such as "sufficiently accurate" or "poor accuracy"), any other suitable output form, or any combination thereof.

Determination 1214 may include processor 314 or post-processor 316 determining whether to repeat any or all of steps 1202-1212, perform any other suitable steps, or any combination thereof. In some embodiments, a set of evaluations may be performed using determination 1214, and the set of evaluations may be compared at step 1216 to select a particular fiducial signal, and corresponding reference points and fiducial points.

In some embodiments, processing system 300 may perform step 1214 to evaluate a set of fiducial signals by repeating at least steps 1206-1212, selecting different fiducial points at step 1206 for each evaluation using a particular reference point(s) of step 1204. For example, pre-processor 312 may select various fiducial points for a particular physiological signal and reference point(s), and processor 314, post-processor 316, or both may evaluate the fiducial signals corresponding to each of the various fiducial points, as shown by step 1216.

In some embodiments, processing system 300 may perform step 1214 to evaluate a set of fiducial signals by repeating at least steps 1204-1212, selecting different fiducial points at step 1206 for each evaluation, based on a set of reference points of step 1204. For example, pre-processor 312 may select various combinations of reference points and fiducial points for a particular physiological signal, and processor 314 or post-processor 316 may evaluate the fiducial signals corresponding to each of the various combinations, as shown by step 1216.

In some embodiments, processing system 300 may perform step 1214 to evaluate a set of fiducial signals by repeating at least steps 1202-1212, selecting different fiducial points at step 1206 for each evaluation, based on a set of reference points of step 1204, for a set of physiological signals of step 1202. For example, pre-processor 312 may select various combinations of reference points and fiducial points for each physiological signal of the set of physiological signals, and processor 314 or post-processor 316 may evaluate the fiducial signals corresponding to each of the various combinations, as shown by step 1216.

Step 1216 may include processor 314 or post-processor 316 comparing a set of fiducial signals based at least in part on the evaluation of step 1212. In some embodiments, step 1216 may include processor 314 or post-processor 316 selecting the fiducial signal (along with the corresponding reference points and fiducial points) corresponding to a lowest RMSD value.

In an illustrative example, pre-processor 312 may receive a PPG signal including a set of successive pulse waves at step 1202. Pre-processor 312 may select a set of reference points on the PPG signal corresponding to the successive peaks in the first derivative of the PPG signal at step 1204. Also, at step 1204, pre-processor 312 may select a maximum in the PPG signal located between each set of successive reference points. At step 1206, pre-processor 312 may select a fiducial point corresponding to each reference point, located a particular time interval away from the reference point, generating a set of fiducial points. Pre-processor 312 may generate a fiducial signal at step 1208, including the set of fiducial points of step 1206, and processor 314, post-processor 316, or both may determine physiological information such as values of respiration information at step 1210. At step 1212, processor 314 or post-processor 316 may evaluate a series of values for respiration information of step 1210 against a reference series of values of respiration information by calculating a RMSD value. Processing system 300 may repeat steps 1206-1212 to generate a set of fiducial signals and corresponding evaluations, using determination 1214. At step 1216, processor 314 or post-processor 316 may compare the set of evaluations generated at step 1212, and select a particular fiducial signal along with corresponding fiducial points. Processing system 300 may use the time interval of the corresponding fiducial points as a pre-set time interval for subsequent analysis.

Figure 13:
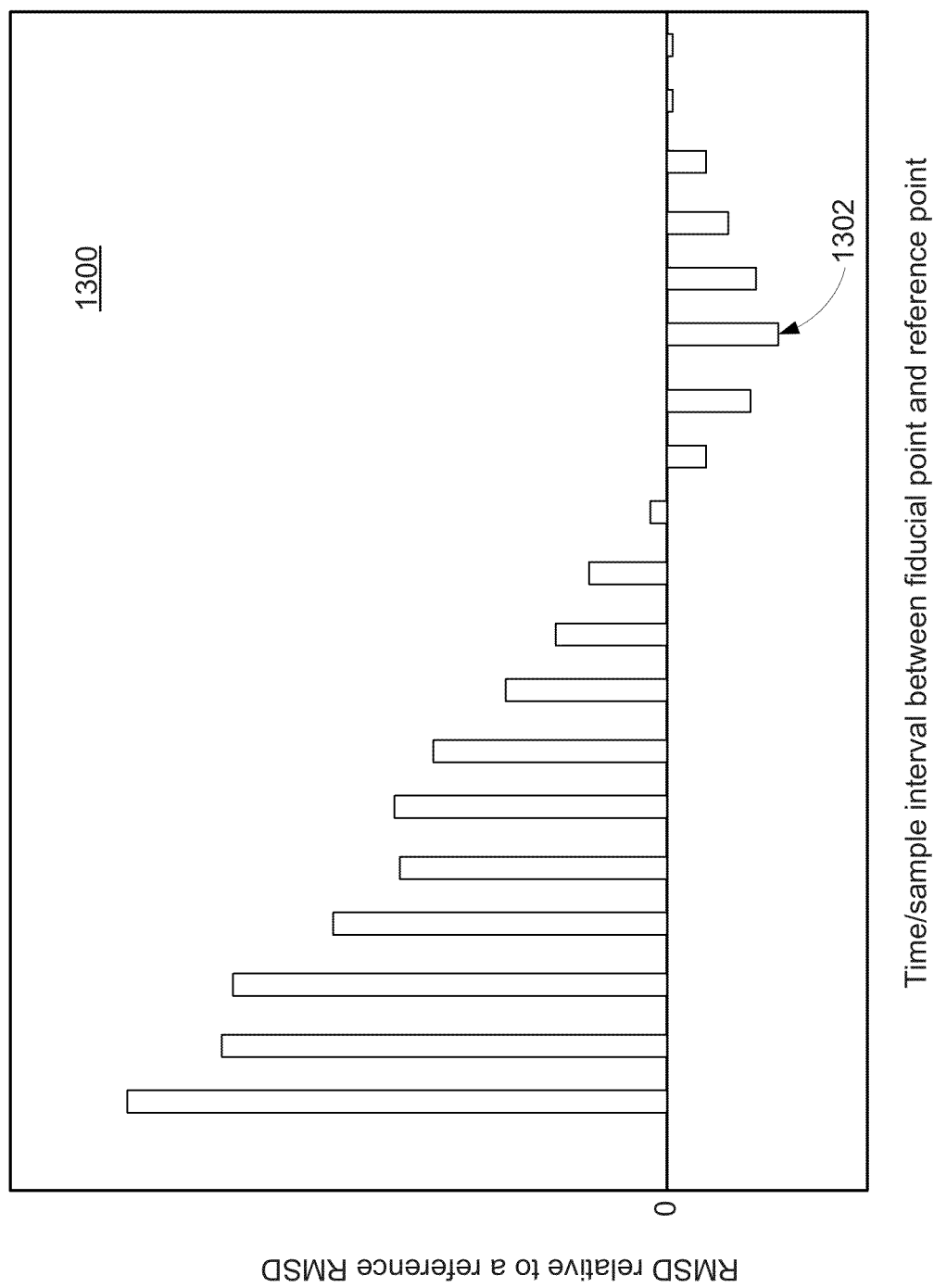
FIG. 13 shows a chart of an illustrative comparison for various fiducial point selections in accordance with some embodiments of the present disclosure.

FIG. 13 shows an illustrative comparison for various fiducial point selections on a particular PPG signal, in accordance with the present disclosure. The abscissa of graph 1300 is in units of time interval, increasing to the right. The ordinate of graph 1300 is in units of RMSD relative to a reference RMSD. The RMSD value is calculated between respiration information such as respiration rate derived from a fiducial signal corresponding to each time interval, and a reference respiration rate (e.g., calculated by a reference analysis or program or calculated using an independent monitoring device). The maximum reduction is shown by relative RMSD 1302. In some embodiments, the time interval corresponding to RMSD 1302 may be used as a preset time interval to locate fiducial points relative to a reference point. In some embodiments, a database of optimal time intervals may be created, and mapped across pulse rate, respiration rate, any other suitable parameter, or any combination thereof.

Any of the illustrative steps of flow diagrams 900-1200 may be combined with other steps, omitted, rearranged, or otherwise altered in accordance with the present disclosure.

Figure 14:
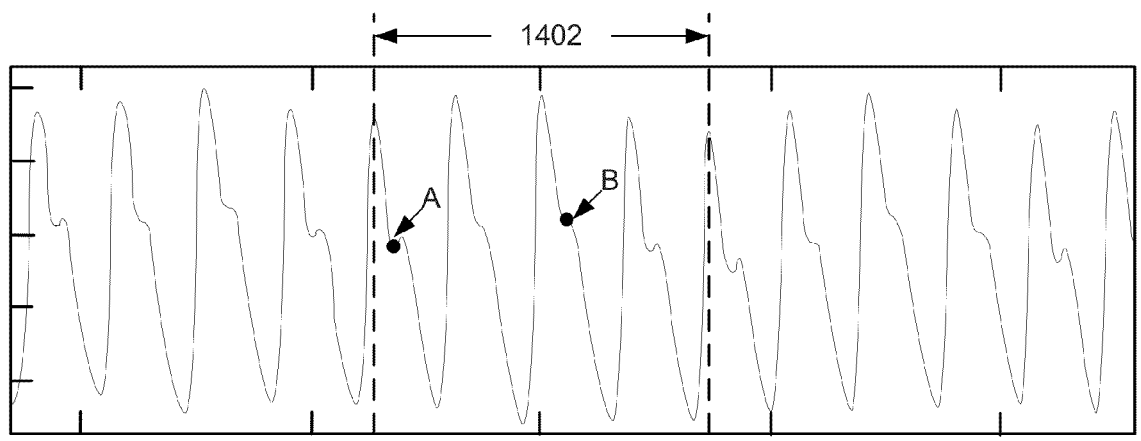
FIG. 14 shows an illustrative PPG signal having morphology characteristics relating to respiration in accordance with some embodiments of the present disclosure.
Figure 15:
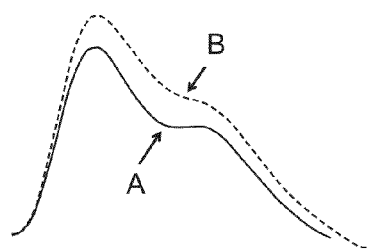
FIG. 15 illustrates an effect of respiration on a PPG signal in accordance with some embodiments of the present disclosure.

An example of a PPG signal changing its morphology over a series of pulse cycles associated with a respiratory cycle is depicted in FIG. 14 and FIG. 15. A respiratory cycle may typically have a longer period (lower frequency) than a pulse cycle and may span a number of pulse periods. A respiratory cycle may span a number of pulse cycles based on the relative respiration rate and pulse rate. An exemplary respiratory cycle 1402 may span four pulse periods as depicted in FIG. 14. Respiration may impact the shape of the pulse waveform, e.g., by amplitude and frequency modulation. For example, as depicted in FIG. 15, a first pulse associated with the respiratory cycle may have a relatively low amplitude as well as an obvious distinct dichrotic notch as indicated by point A. A second pulse may have a relatively high amplitude as well as a dichrotic notch that has been washed out as depicted by point B. FIG. 15 depicts the pulses associated with point A and B superimposed on the same scale for comparison. By the end of the respiratory cycle the pulse features may again be similar to the morphology of A. Respiration may have varied effects on the morphology of a PPG signal other than those depicted in FIG. 15.

In some embodiments, pre-processor 312 may calculate morphology metrics to be used as inputs to determine respiration information. Pre-processor 312 may receive a PPG signal as input signal 310 and may perform various filtering operations before calculating morphology metrics. Although a PPG signal may be described herein, it will be recognized that morphology metrics may be calculated from various other signals that may include respiration information. The PPG signal may be filtered to remove any artifacts outside of the bandwidth of interest for respiration. The PPG signal may be filtered in a manner to achieve a net zero phase change, for example by filtering once in the forward direction and then again in the reverse direction. An example filter may be a third order Butterworth filter with a cutoff frequency of 7 Hz. Other filters may be used to remove artifacts outside of the bandwidth of interest for respiration, and filters may be chosen to remove varying degrees of artifacts. Other operations may also be performed, such as establishing fiducial points as described herein.

Pre-processor 312 may calculate one or more sets of morphology metric values from the received signal. A PPG signal to be evaluated may be in the form of samples having a corresponding sampling rate. For example, a sampling rate of a PPG signal may be 76 Hz.

Figure 16:
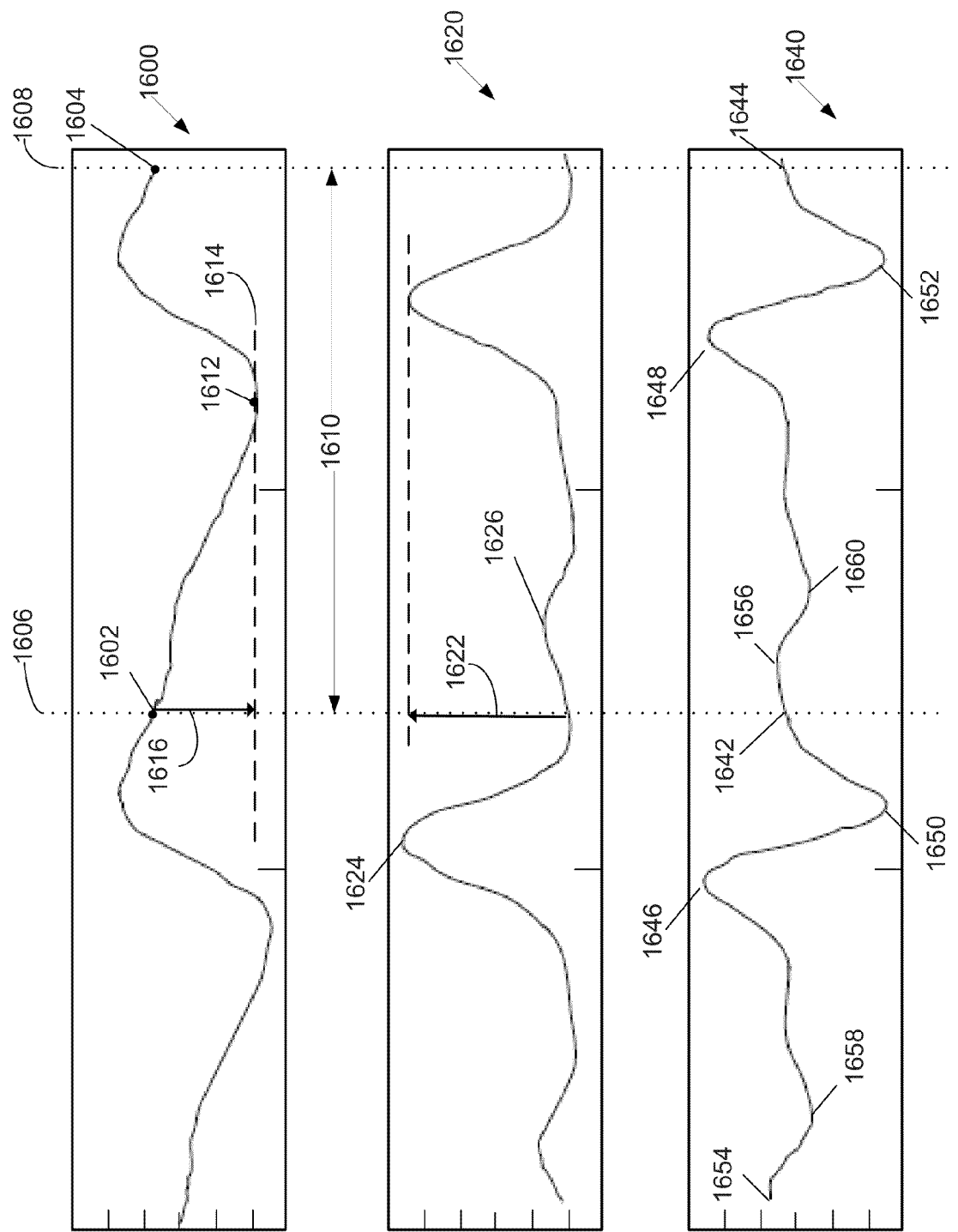
FIG. 16 shows an illustrative PPG signal, a first derivative of the PPG signal, and a second derivative of the PPG signal in accordance with some embodiments of the present disclosure.

FIG. 16 depicts signals used for calculating morphology metrics from a received PPG signal. The abscissa of each plot of FIG. 16 may be represent time and the ordinate of each plot may represent magnitude. PPG signal 1600 may be a received PPG signal, first derivative signal 1620 may be a signal representing the first derivative of the PPG signal 1600, and second derivative signal 1640 may be a signal representing the second derivative of the PPG signal 1600. As will be described below, these signals may be utilized to calculate morphology metrics that may be used as inputs by processor 314 or post-processor 316 to determine respiration information such as respiration rate. Although particular morphology metric determinations are set forth below, each of the morphology metric calculations may be modified in any suitable manner. Any of a plurality of morphology metrics may be utilized in combination to determine respiration information.

Exemplary fiducial points 1602 and 1604 are depicted for PPG signal 1600, and fiducial lines 1606 and 1608 demonstrate the location of fiducial points 1602 and 1604 relative to first derivative signal 1620 and second derivative signal 1640. The fiducial points may be determined by pre-processor 312 as described herein. Fiducial points 1602 and 1604 may define a fiducial-defined portion 1610 of PPG signal 1600. The fiducial points 1602 and 1604 may define starting ending points for determining morphology metrics as described herein, and the fiducial-defined portion 1610 may be define a relevant portion of data for determining morphology metrics as described herein. It will be understood that other starting points, ending points, and relative portions of data may be utilized to determine morphology metrics.

An exemplary morphology metric may be a down metric. The down metric is the difference between a first (e.g., fiducial) sample of a fiducial-defined portion (e.g., fiducial defined portion 1610) of the PPG signal (e.g., PPG signal 1600) and a minimum sample (e.g., minimum sample 1612) of the fiducial-defined portion of the PPG signal. A down metric may also be calculated based on other points of a fiducial-defined portion. The down metric is indicative of physiological characteristics which are related to respiration, e.g., amplitude and baseline modulations of the PPG signal. In an exemplary embodiment fiducial point 1602 defines the first location for calculation of a down metric for fiducial-defined portion 1610. In the exemplary embodiment the minimum sample of fiducial-defined portion 1610 is minimum point 1612, and is indicated by horizontal line 1614. The down metric may be calculated by subtracting the value of minimum point 1612 from the value of fiducial point 1602, and is depicted as down metric 1616.

Figure 17:
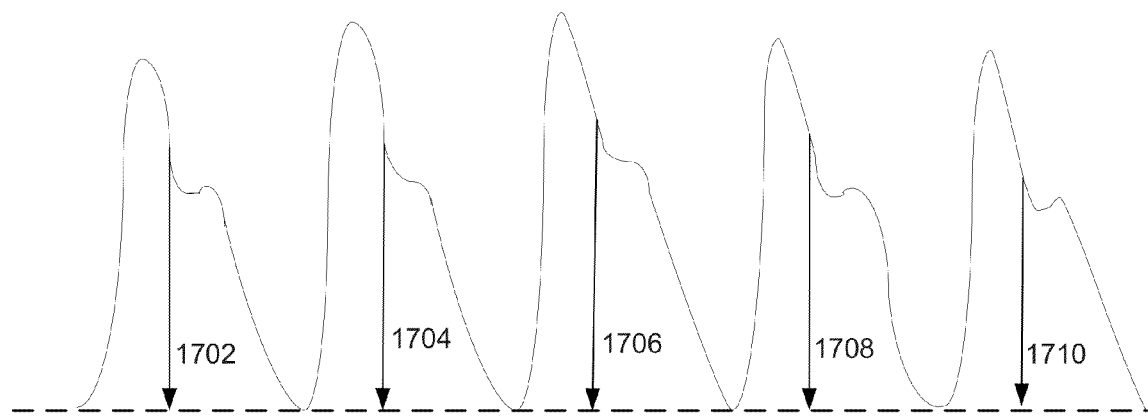
FIG. 17 shows an illustrative amplitude modulated PPG signal in accordance with some embodiments of the present disclosure.
Figure 18:
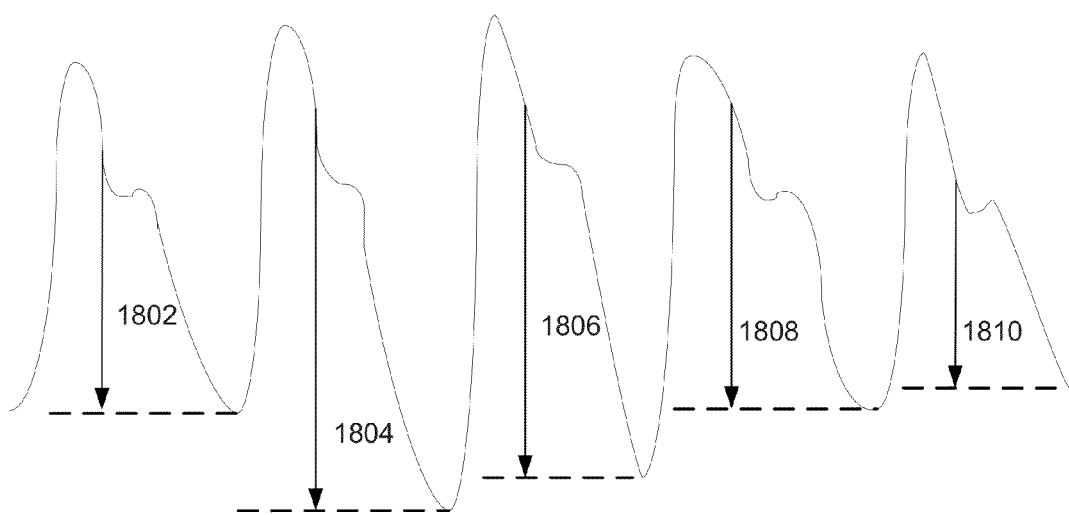
FIG. 18 shows an illustrative baseline and amplitude modulated PPG signal in accordance with some embodiments of the present disclosure.

A more detailed view of down metrics for multiple fiducial-defined portions is depicted in FIG. 17 for an amplitude modulated PPG signal. Each fiducial-defined portion has an associated down metric 1702, 1704, 1706, 1708, and 1710. The values and change in values of the down metric may be utilized as described herein to generate morphology metric signals that are used as an input to determine respiration information, such as respiration rate. FIG. 18 depicts down metrics for a PPG signal that includes baseline as well as amplitude modulation. Each fiducial-defined portion has an associated down metric 1802, 1804, 1806, 1808, and 1810. The values and change in values of the down metric may be utilized as described herein to generate morphology metric signals that are used as an input to determine respiration information.

Another exemplary morphology metric may be a kurtosis metric for a fiducial-defined portion. Kurtosis measures the peakedness of the first derivative 1620 of the PPG signal. The peakedness is sensitive to both amplitude and period (frequency) changes, and may be utilized as an input to determine respiration information, such as respiration rate. Kurtosis may be calculated based on the following formulae:

$$D = \frac{1}{n}\sum_{i=1}^{n}(x_i' - \overline{x'})^2$$

$$\mathrm{Kurtosis} = \frac{1}{nD^2}\sum_{i=1}^{n}(x_i' - \overline{x'})^4$$

where:
$x_i'$=ith sample of $1^{st}$ derivative;
$\overline{x'}$=mean of 1st derivative of fiducial-defined portion;
n=set of all samples in the fiducial-defined portion Another exemplary morphology metric may be a delta of the second derivative (DSD) between consecutive fiducial-defined portions, e.g., at consecutive fiducial points. Measurement points 1642 and 1644 for a DSD calculation are depicted at fiducial points 1602 and 1604 as indicated by fiducial lines 1606 and 1608. The second derivative is indicative of the curvature of a signal. Changes in the curvature of the PPG signal are indicative of changes in internal pressure that occur during respiration, particularly changes near the peak of a pulse. By providing a metric of changes in curvature of the PPG signal, the DSD morphology metric may be utilized as an input to determine respiration information, such as respiration rate. The DSD metric may be calculated for each fiducial-defined portion by subtracting the second derivative of the next fiducial point from the second derivative of the current fiducial point.

Another exemplary morphology metric may be an up metric measuring the up stroke of the first derivative signal 1620 of the PPG signal. The up stroke may be based on an initial starting sample (fiducial point) and a maximum sample for the fiducial-defined portion and is depicted as up metric 1622 for a fiducial point corresponding to fiducial line 1606. The up metric may be indicative of amplitude and baseline modulation of the PPG signal, which may be related to respiration information as described herein. Although an up metric is described herein with respect to the first derivate signal 1620, it will be understood that an up metric may also be calculated for the PPG signal 1600 and second derivative signal 1640.

Another exemplary morphology metric may be a skew metric measuring the skewness of the original PPG signal 1600 or first derivative 1620. The skew metric is indicative of how tilted a signal is, and increases as the PPG signal is compressed (indicating frequency changes in respiration) or the amplitude is increased. The skewness metric is indicative of amplitude and frequency modulation of the PPG signal, which may be related to respiration information as described herein. Skewness may be calculated as follows:

$$g1 = \frac{m_3}{m_2^{3/2}} = \frac{\frac{1}{n}\sum_{i=1}^{n}(x_i - \bar{x})^3}{\left(\frac{1}{n}\sum_{i=1}^{n}(x_i - \bar{x})^2\right)^{3/2}}$$

where:
$x_i$=ith sample;
$\bar{x}$=mean of the samples of the fiducial-defined portion;
$m_3$=third moment;
$m_2$=second moment; and
n=total number of samples.

Another exemplary morphology metric may be a b/a ratio metric (i.e., b/a), which is based on the ratio between the a-peak and b-peak of the second derivative signal 1640. PPG signal 1600, first derivative signal 1620, and second derivative signal 1600 may include a number of peaks (e.g., four peaks corresponding to maxima and minima) which may be described as the a-peak, b-peak, c-peak, and d-peak, with the a-peak and c-peak generally corresponding to local maxima within a fiducial defined portion and the b-peak and d-peak generally corresponding to local minima within a fiducial defined portion. For example, the second derivative of the PPG signal may include four peaks: the a-peak, b-peak, c-peak, and d-peak. Each peak may be indicative of a respective systolic wave, i.e., the a-wave, b-wave, c-wave, and d-wave. On the depicted portion of the second derivative of the PPG signal 1640, the a-peaks are indicated by points 1646 and 1648, the b-peaks by points 1650 and 1652, the c-peaks by points 1654 and 1656, and the d-peaks by points 1658 and 1660. The b/a ratio measures the ratio of the b-peak (e.g., 1650 or 1652) and the a-peak (e.g., 1646 or 1648). The b/a ratio metric may be indicative of the curvature of the PPG signal, which demonstrates frequency modulation based on respiration information such as respiration rate. The b/a ratio may also be calculated based on the a-peak and b-peak in higher order signals such as PPG signal and first derivative PPG signal 1620.

Another exemplary morphology metric may be a c/a ratio (i.e., c/a), which is calculated from the a-peak and c-peak of a signal. For example, first derivate PPG signal 1620 may have a c-peak 1626 which corresponds to the maximum slope near the dichrotic notch of PPG signal 1600, and an a-peak 1624 which corresponds to the maximum slope of the PPG signal 1600. The c/a ratio of the first derivative is indicative of frequency modulation of the PPG signal, which is related to respiration information such as respiration rate as described herein. A c/a ratio may be calculated in a similar manner for PPG signal 1600 and second derivative signal 1640.

Another exemplary morphology metric may be a i_b metric measuring the time between two consecutive local minimum (b) locations 1650 and 1652 in the second derivative 1640. The i_b metric is indicative of frequency modulation of the PPG signal, which is related to respiration information such as respiration rate as described herein. The i_b metric may also be calculated for PPG signal 1600 or first derivative signal 1620.

Another exemplary morphology metric may be a peak amplitude metric measuring the amplitude of the peak of the original PPG signal 1600 or of the higher order derivatives 1620 and 1640. The peak amplitude metric is indicative of amplitude modulation of the PPG signal, which is related to respiration information such as respiration rate as described herein.

Another exemplary morphology metric may be a center of gravity metric measuring the center of gravity of a fiducial-defined portion from the PPG signal 1600 in either or both of the x and y coordinates. The center of gravity is calculated as follows:

Center of gravity $(x) = \Sigma(x_i * y_i)/\Sigma y_i$

Center of gravity $(y) = \Sigma(x_i * y_i)/\Sigma x_i$

The center of gravity metric of the x coordinate for a fiducial-defined portion is indicative of frequency modulation of the PPG signal, which is related to respiration information such as respiration rate as described herein. The center of gravity metric of the y coordinate for a fiducial-defined portion is indicative of amplitude modulation of the PPG signal, which is related to respiration information such as respiration rate as described herein.

Another exemplary morphology metric is an area metric measuring the total area under the curve for a fiducial-defined portion of the PPG signal 1600. The area metric is indicative of frequency and amplitude modulation of the PPG signal, which is related to respiration information such as respiration rate as described herein.

Although a number of morphology metrics have been described herein, it will be understood that other morphology metrics may be calculated from PPG signal 1600, first derivative signal 1620, second derivative signal 1640, and any other order of the PPG signal. It will also be understood that any of the morphology metrics described above may be modified to capture aspects of respiration information or other physiological information that may be determined from a PPG signal.

Figure 19:
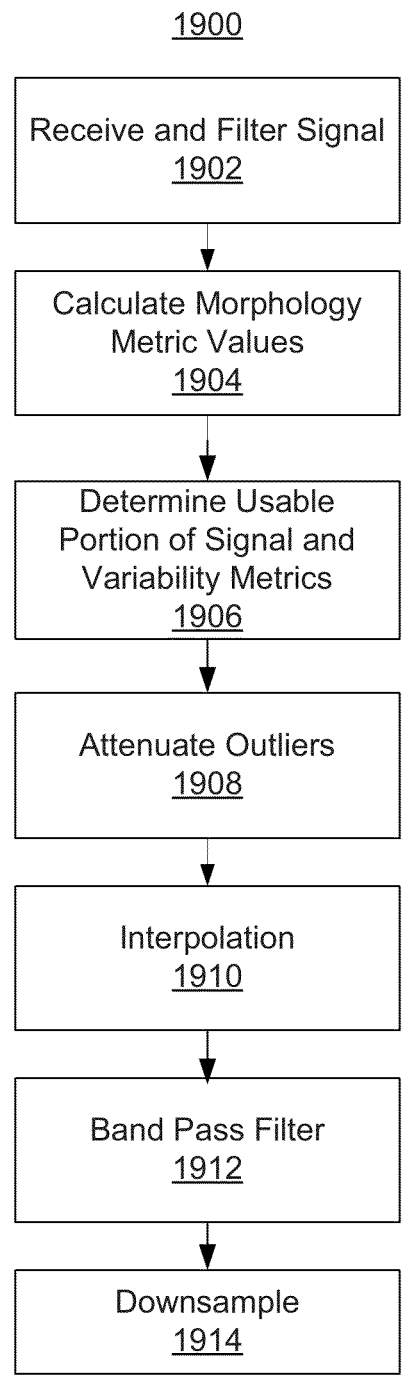
FIG. 19 is flow diagram showing illustrative steps for generating morphology metric signals from a PPG signal in accordance with some embodiments of the present disclosure.

FIG. 19 depicts steps 1900 for generating a morphology metric signal from a PPG signal. The steps described in FIG. 19 may be performed by pre-processor 312, processor 314, a combination of pre-processor 312 and processor 314, or other portions or components of processing system 300. Although steps may be described as being performed by a particular component of processing system 300, it will be recognized that such description is exemplary only. Steps 1900 may be performed in alternative order, steps may be omitted, and additional steps may be inserted into the sequence of steps 1900.

At step 1902, an input signal 310 for computing a morphology metric related to respiration information such as respiration rate may be received, e.g., by pre-processor 312. The received signal may be received directly from a sensor and require further processing to be converted into a digital signal, or may be a digital signal that has previously been processed, e.g., a sampled digital output received from a pulse oximetry device. An exemplary received signal may be a PPG signal from a pulse oximetry device, which may be sampled at a sampling rate, for example, 76 Hz. The received signal may encompass a sampling window such as 5 seconds. Pre-processor 314 may locate reference points and fiducial points to identify one or more fiducial-defined portions, each of which may be utilized to calculate one or more morphology metrics which may be used to generate one or more morphology metric signals for an analysis window (e.g., a 45 second analysis window of the 9 most recent sampling windows) as described herein. The received signal may also be filtered to remove artifacts outside of the bandwidth of interest for respiration. The filter may be a low pass filter or any other filter that removes information outside of the bandwidth of interest. The filter may be implemented in any suitable manner, e.g., with a third order butterworth filter having a cutoff frequency of 7 Hz. The cutoff frequency may be any frequency appropriate to recognize morphology features related to respiration, and may vary based on physiological parameters such as heart rate. In order to maintain morphology features, the feature set may be filtered in a manner to achieve a zero net phase change, e.g., by filtering the PPG signal twice, once in each direction.

At step 1904, pre-processor 312 may calculate morphology metric values from the received signal. Morphology metric values may be calculated for each fiducial-defined portion of the analysis window, e.g., each fiducial-defined portion of the 45 second analysis window. A morphology metric may be any measurement of the form or structure of a signal that may relate to a given physiological characteristic such as respiration information. In an exemplary application, the morphology metric may relate to respiration information such as respiration rate and may be determined from a sampled PPG signal. Morphology metrics may include down metric, kurtosis metric, DSD metric, up metric, skew metric, b/a ratio metric, c/a ratio metric, i_b metric, peak amplitude metric, center of gravity metric, and area metric, and may be calculated as described herein. As described herein, multiple morphology metric values may be calculated from the PPG signal, the first and second derivative of the PPG signal, and other order derivative of the PPG signal, or from any combination thereof.

At step 1906, pre-processor 312 may determine a usable portion of the input signal 310. Portions of the received signal may include samples with values that are unlikely to reflect actual values as a result of inaccurate measurement, user error, or other factors. Input signal 310 may be analyzed to identify divergences in the signal baseline, motion artifacts, divergences in pulse period, and any other signal features that may indicate inaccurate measurement, user error, or other factors. Based on this analysis, pre-processor 312 may identify portions of the input signal 310 to be ignored by processor 314 in calculating values such as respiration information. Only those portions of the calculated morphology metric values that correspond to the usable portion of the input signal may be provided to processor 314. Pre-processor 312 may also calculate additional values relating to the usable portion of the signal, such as variability of the signal amplitude, variability of the pulse period, an average age for the usable portion of the signal, and other parameters relating to the quality of the PPG signal. The amplitude variability, pulse period variability, age, and other parameters may be provided to processor 314, post-processor 316, or both.

At step 1908, one or more sets of the received morphology metric values may be attenuated by processor 314 to adjust outliers. In an exemplary embodiment, pre-processor 312 may calculate a series of morphology metric values for a set of fiducial-defined portions. A threshold may be calculated for determining which values should be attenuated, and an attenuation value may be determined to attenuate outliers. The attenuation value may modify outliers in any manner, such as with a cutoff value or by reducing the outliers based on a percentage or other formula. In an exemplary embodiment, the attenuation value may be equal to the threshold and any outliers that exceed the threshold may be set to the threshold. The threshold may be calculated based on characteristics of the underlying signal, the morphology metrics, empirically determined values, any other suitable technique, or any combination thereof. The threshold may be the same for positive and negative values or each polarity may have its own threshold and attenuation value. An exemplary threshold may be based on the standard deviation of a series of calculated morphology metric values multiplied by a constant. The exemplary attenuation value may be equal to the threshold, and the threshold and attenuation values may be the same for negative values.

At step 1910, the attenuated series of morphology metric values may be interpolated by processor 314 to derive a morphology metric signal that may be indicative of respiration information such as respiration rate. An exemplary interpolation technique may be to perform linear interpolation on the time series of calculated morphology metrics. It will be understood that any suitable interpolation technique may be used to derive the morphology metric signal, such as higher order curve-fitting techniques. The interpolation may be performed at a rate different from the sampling rate of the original PPG signal that formed the basis of the morphology metric. For example, morphology metrics calculated from an exemplary 76 Hz PPG input may be interpolated at a ⅙ of the original rate, or at 12.66 Hz, to create an interpolated morphology metric signal.

At step 1912, the interpolated morphology metric signal may be filtered by processor 314 to smooth the signal and remove information that is outside the interest for respiration. An exemplary filter may be a band-pass filter that removes information outside of the bandwidth of interest for respiration. For three exemplary sets of morphology metrics, the exemplary pass bands may be 0.15 Hz-0.9 Hz (down metric), 0.07-0.7 Hz (kurtosis metric), and 0.07-0.7 Hz (DSD metric). The feature set may be filtered twice, once in each direction, to achieve a zero net phase change. It will be understood that that the filter may be implemented in any suitable manner, and that any suitable pass bands may be used for the filter.

At step 1914, the filtered morphology metric signal may be downsampled by processor 314 to a sampling rate to be used as an input to derive respiration information such as respiration rate. For example, the filtered morphology metric signal may be downsampled to a lower frequency value such as 2.53 Hz. This sampling rate may be common for multiple morphology metrics, such that different morphology metrics may be more easily compared to determine respiration information such as respiration rate.

Steps 1900 may be repeated to generate each morphology metric signal. In an exemplary embodiment, steps 1900 may be repeated to generate a down metric signal, a kurtosis metric signal, and a DSD metric signal. It will be understood that any number or combination of morphology metric signals may be generated for the morphology metrics described herein.

Figure 20:
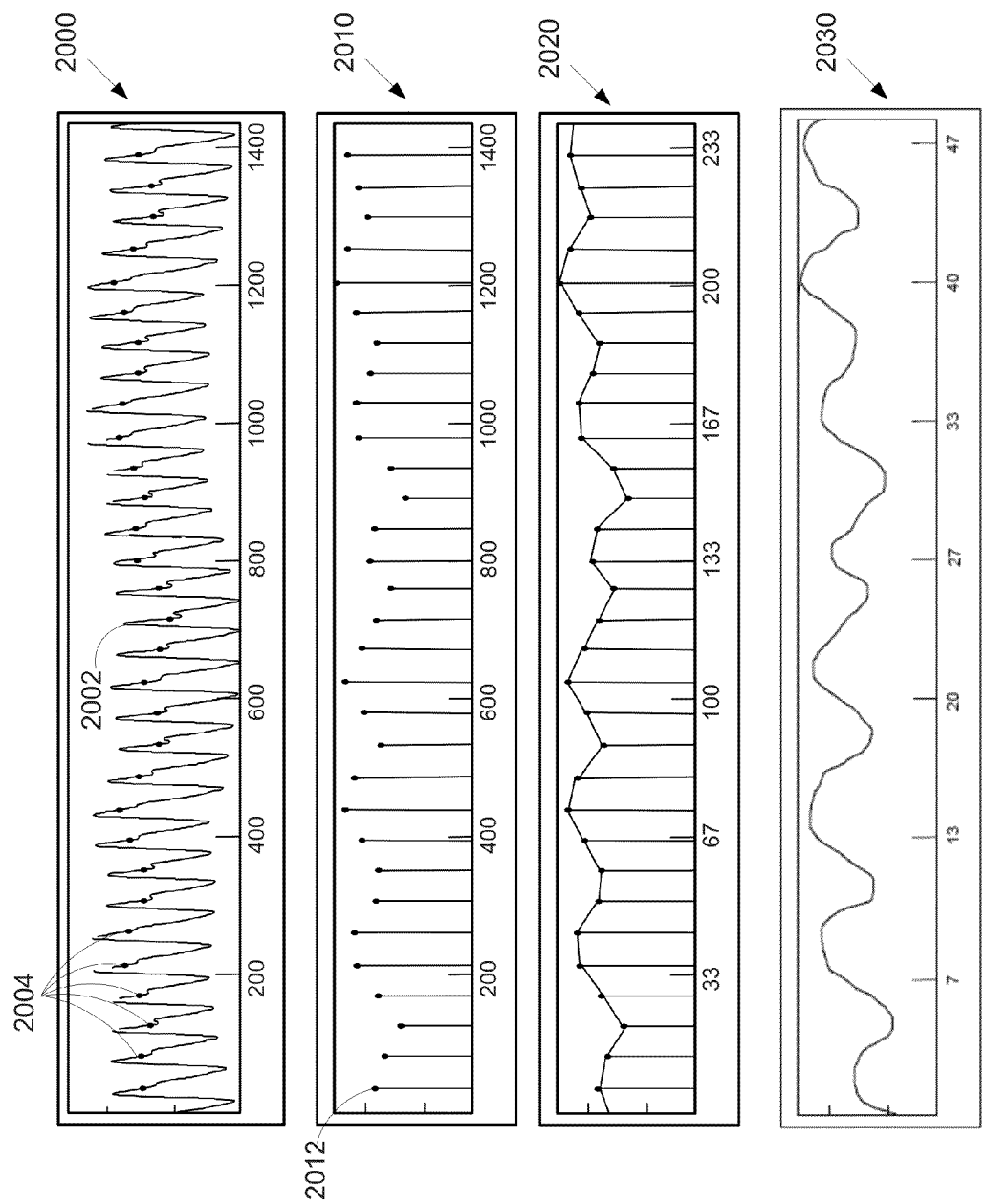
FIG. 20 shows a series of graphs illustrating how a down metric signal may be generated from a PPG signal in accordance with some embodiments of the present disclosure.

FIG. 20 depicts a set of plots 2000, 2010, 2020, and 2030 depicting aspects of the signal processing steps for calculating a morphology metric signal from a PPG signal as described herein. Specifically, FIG. 20 depicts an exemplary calculation of a down metric signal from an exemplary PPG signal 2002 in accordance with the steps described herein. Although FIG. 20 depicts an example of determining a down metric, each morphology metric may be processed in a similar manner. Alternatively, each morphology metric may have its own process or set of parameters to derive a signal useful for determining respiration information from a PPG signal. With respect to any morphology metric, additional operations such as filtering and calculation steps may be performed, and steps discussed below may be omitted.

PPG signal 2002 may be received, e.g., by pre-processor 312 as input signal 310, as digital data with a sampling rate based on the output of a device such as a pulse oximeter. Input signal may be streamed to pre-processor 312 or may be received in discrete sampling windows, e.g., every 5 seconds of data. Plot 2000 may be depicted in units of samples on the abscissa and magnitude on the ordinate, based on a sampling rate of 76 Hz. Although 76 Hz is an exemplary sampling rate, any sampling rate may be utilized to provide an interface with a pulse oximeter or other device providing the PPG signal. Plot 2000 may depict a portion of an analysis window used to generate morphology metric signals. An exemplary analysis window may include 45 seconds of samples, and morphology metrics may be recalculated for the analysis window for each new 5 second sampling window of PPG values that is received.

Plot 2000 depicts a portion of an analysis window for which a morphology metric signal may be determined from the PPG signal. Fiducial points 2004 may be calculated as described herein and may be utilized in determining a down metric for PPG signal 2002 for each fiducial defined portion. Although a down metric is described herein, PPG signal 2002 (and the first and second derivative of PPG signal 2002) may be utilized to determine other morphology metrics as described herein. The fiducial point 2004 locations depicted in plot 2000 are exemplary, and other fiducial point 2004 locations may be used to determine the down metric and other morphology metrics.

A down metric may be calculated for each fiducial-defined portion of the PPG signal as described herein, e.g., by calculating the difference between the amplitude at the fiducial point and the lowest-amplitude sample for each fiducial-defined portion. The resulting morphology metric values may be provided to processor 314, and any unusable portions of the analysis window may be removed as described herein. In the exemplary embodiment depicted in FIG. 20, the complete set of down metric values depicted in plot 2010 may be provided to processor 314 as a portion of an analysis window. Plot 2010 is depicted in units of samples on the abscissa and magnitude on the ordinate, based on the original sampling rate of the received PPG signal 2002, e.g., 76 Hz. Each down metric 2012 may be located at the starting fiducial point for each respective fiducial-defined portion. Once the down metric values are calculated, those values may be attenuated as described herein. A standard deviation may be calculated for the down metric values. A threshold may be based on that standard deviation multiplied by a constant, e.g., 1.6. Any down metric values exceeding 1.6*(standard deviation of down metrics) may be attenuated to the threshold value. It will be recognized that other suitable threshold values and attenuation values may be utilized as described herein.

A linear interpolation of the down metric values may then be performed. The linear interpolation may be at a lower frequency than the 76 Hz PPG input signal, e.g., at 12.66 Hz. Plot 2020 depicts a linear interpolation of the attenuated down metric values. The interpolated values may then be filtered to remove information outside of the bandwidth of interest as described herein. For example, a window of interest may capture respiration rate information ranging from 3 to 50 breaths per minute, e.g., using a bandpass filter. The resulting morphology metric signal may be downsampled to a lower frequency value such as 2.53 Hz. This sampling rate may be a common for multiple morphology metrics, such that different morphology metrics may be compared on the same scale to determine respiration information such as respiration rate. It will be understood that downsampling may be accomplished in any suitable manner, and that the resulting signal may have any suitable frequency. Plot 2030 depicts the resulting morphology metric signal.

Figure 21:
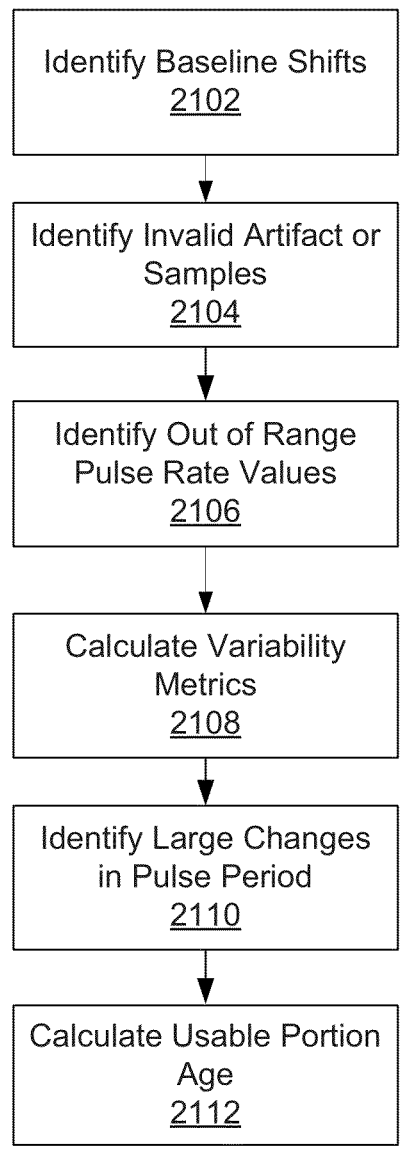
FIG. 21 is a flow diagram showing illustrative steps for determining which portions of the analysis window include useable data in accordance with some embodiment of the present disclosure.

In an exemplary embodiment, pre-processor 312 may perform a number of tests to determine whether any portions of the information calculated from the analysis window (e.g., one or more morphology metrics calculated for a 45 second analysis window) should be ignored, discarded, or deemphasized, and calculate a number of related values. FIG. 21 depicts steps for determining which portions of the analysis window include useable data. The steps depicted in FIG. 21 may be executed in any order, any or all of the steps may be omitted, and additional steps may be included.

At step 2102, pre-processor 312 may identify any large baseline shifts that may result in unusable or degraded performance for the calculation of respiration information. The PPG signal may be filtered in any suitable manner. For example, the original PPG signal may be filtered with a $3^{rd}$ order Butterworth filter about a region of interest such as 0.07 to 0.7 Hz. To achieve a zero phase change, the signal may be filtered twice, once in each direction. The absolute value of each sample of the resulting signal may be compared to a threshold corresponding to a baseline shift, for example, at 2.9 multiplied by the standard deviation of the baseline signal. It will be understood that any suitable threshold may be used and that the threshold may be based on any suitable baseline other than the standard deviation. Any samples that exceed the threshold may indicate areas of data to be ignored or deemphasized in future calculations such as for respiration information. The portion of the data to be ignored or deemphasized may be determined in any suitable manner. For example, pre-processor 312 may identify the largest section of the resulting signal that does not include any outliers. That portion of the signal may be used for subsequent calculations, and in some instances an additional buffer section (e.g., 5 seconds) may be removed from the usable portion adjacent to any identified outliers.

At step 2104, pre-processor 312 may identify invalid artifacts or samples in the usable portion identified in step 2102. It will be understood that the presence of an invalid artifact or sample may be determined in any suitable manner. For example, a last artifact or invalid sample flag may be received with the PPG signal as described herein. If either flag is asserted during a portion of the usable portion of the PPG signal from step 2102, portions of the PPG signal corresponding to the last artifact or invalid sample flag may be removed from the usable portion in any suitable manner. For example, portions corresponding to an invalid artifact or sample may be removed by ignoring the artifact or invalid sample event and any portions of the usable signal that occur prior to the artifact or invalid sample event.

At step 2106, pre-processor 312 may identify any out of range pulse values within the usable portion of the analysis window. The appropriate range may be determined in any suitable manner. For example, a valid pulse rate range may be 40 to 170 beats per minute. Pre-processor 312 may maintain a running average of the pulse rate corresponding to a portion of the analysis windows, e.g., for each 5 second sampling window. If at any time the running average is less than the minimum pulse rate (e.g., 40 beats per minute) or is greater than the maximum pulse rate (e.g., 170 beats per minute), portions of the overall analysis window that correspond to the out of range portion may be ignored or deemphasized in any suitable manner, e.g., by ignoring all data that precedes the out of range portion.

At step 2108, pre-processor 312 may calculate variability metrics for the remaining usable portion of the analysis window (e.g., after steps 2102-2106) for subsequent use by processor 314, post-processor 316, or both. An amplitude variability metric may be calculated in any suitable manner. For example, the amplitude variability metric may be calculated by subtracting the minima from the maxima for each fiducial-defined portion. An amplitude difference may be calculated for each set of consecutive fiducial-defined portions. Once all of the amplitude and amplitude difference values are calculated, an amplitude variability metric may be the sum of the amplitude difference values divided by the sum of the amplitude values. Calculation of the amplitude variability metric may be performed as follows:

$$amp(i) = \text{max sample in } i\text{th pulse} - \text{min sample in } i\text{th pulse}$$

$$ampDiff(i) = |amp(i+1) - amp(i)|$$

$$\text{Amplitude Variability} = \frac{\sum_{i=1}^{n-1} ampDiff(i)}{\sum_{i=1}^{n-1} amp(i)}$$

A period variability metric may be based on a period which and may be calculated in any suitable manner. For example, a period variability metric may be calculated for each fiducial-defined portion. A period difference may be calculated for each set of consecutive fiducial-defined portions. Once all of the period and period difference values are calculated, a period variability metric may be the sum of the period difference values divided by the average pulse period over the 45 second analysis window. Calculation of the period variability metric may be performed as follows:

$$perDiff(i) = |period(i) - period(i+1)|$$

$$\text{Pulse Period} = \left(\frac{1}{dt}\right) * \frac{60}{\text{Mean Non-Zero Pulse Rate over last 45 seconds}}$$

$$\text{Period Variability} = \frac{\sum_{i=1}^{n-1} perDiff(i)}{\text{Pulse Period}}$$

$$dt = \text{Sample Period} = .0132 \text{ ms}$$

At step 2110, pre-processor 312 may identify any portions of the usable portion of the analysis window where adjacent fiducial-defined portions have a pulse period difference that exceeds a threshold. A threshold for the pulse period difference may be determined in any suitable manner. For example, if the difference between the pulse period for two consecutive fiducial-defined portions exceeds 30% of the average pulse period for the analysis window, any data corresponding to these fiducial-defined portions may be ignored, e.g., by excluding any data of the usable portion of the analysis window that occurs prior to the invalid pulse period.

At step 2112, pre-processor 312 may calculate the age of the usable portion of the analysis window. The age of the usable portion of the analysis may be calculated in any suitable manner. For example, if the full analysis window of 45 seconds is usable, the age of the analysis window may be 22.5 seconds. As another example, if the most recent 10 seconds of the analysis window are not usable, and only the prior 35 seconds of the analysis window are usable, the age may be 27.5 seconds, i.e., 10 seconds (first valid sample) plus 45 seconds (last valid sample) divided by 2.

Figure 22A:
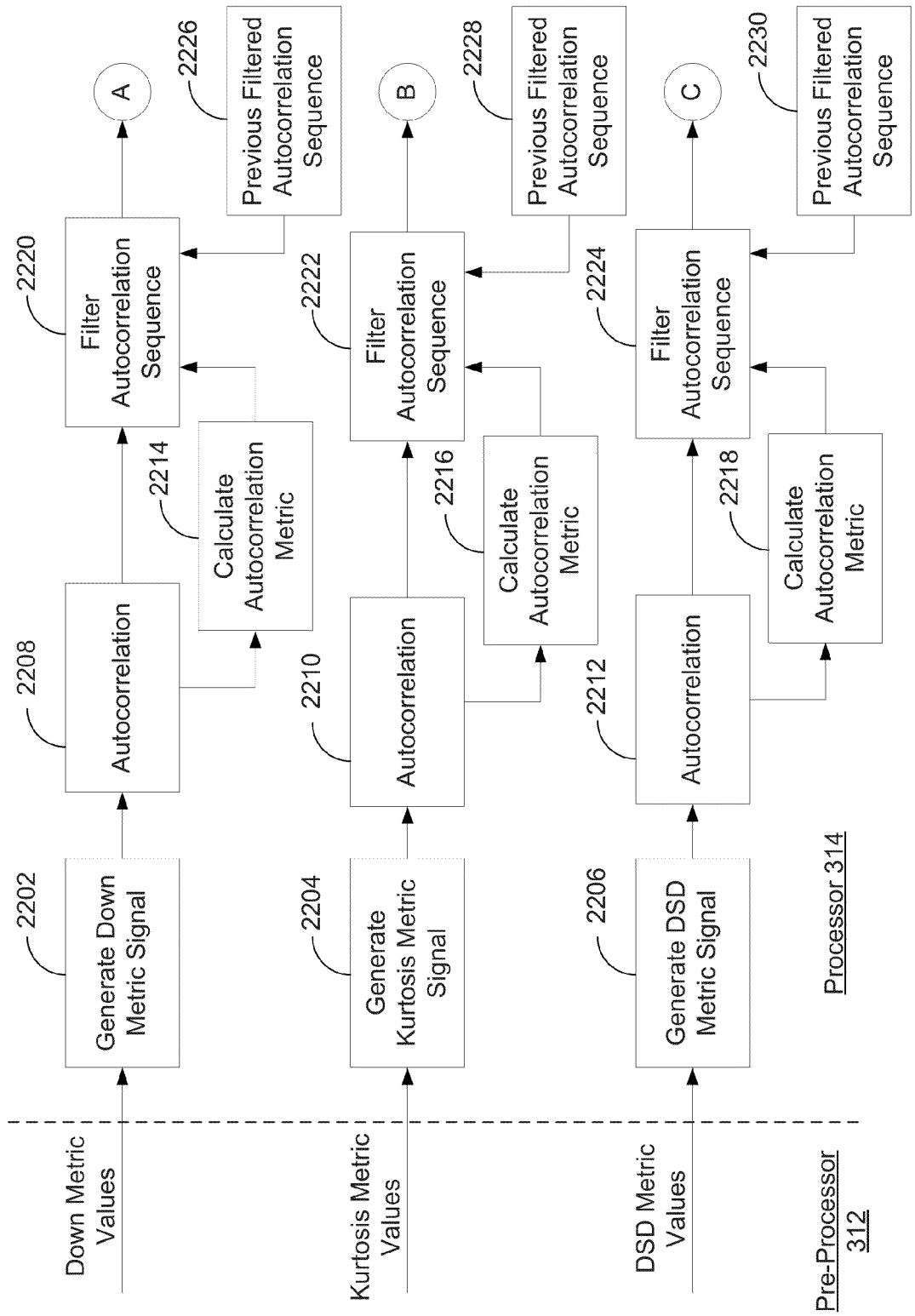
FIGS. 22A and 22B is a flow diagram showing illustrative steps for generating respiration information utilizing autocorrelation of morphology metric signals in accordance with some embodiments of the present disclosure.
Figure 22B:
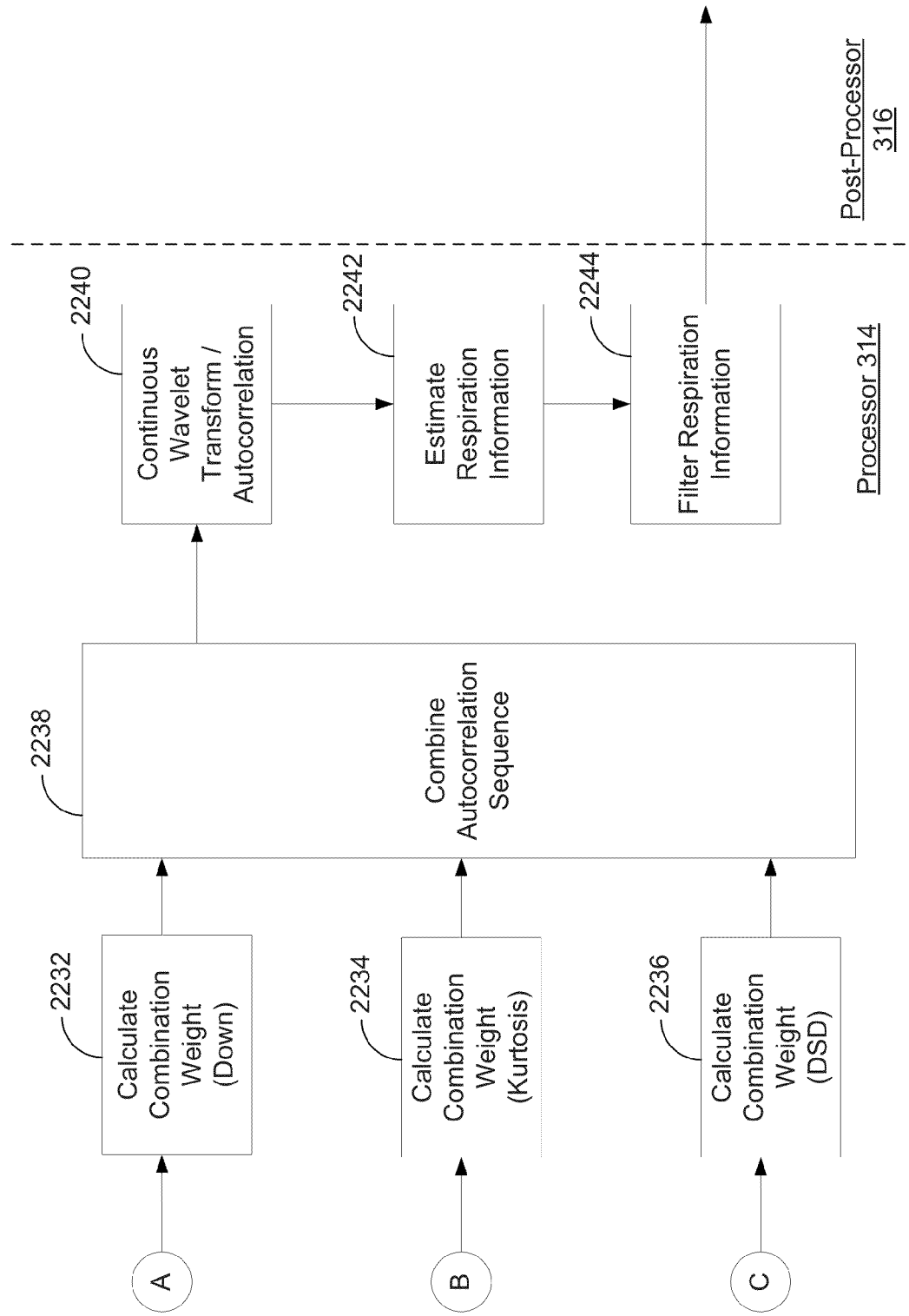

Steps for generating respiration information such as a respiration rate are depicted in FIGS. 22A and 22B. In an exemplary embodiment, processor 314 may perform the steps described herein, however it will be understood that some or all of the steps may be performed by pre-processor 312, post-processor 316, or other suitable processing circuitry. In an exemplary embodiment processor 314 may receive one or more sets of morphology metric values from pre-processor 312. In an exemplary embodiment processor 314 may receive sets of morphology metric values for the down metric, kurtosis metric, and DSD metric. It will be understood that any number of sets of morphology metric values may be received, and that the types of morphology metrics may be any suitable metrics as described herein. In an exemplary embodiment, at step 2202 processor 314 may derive a down metric signal as described herein, including attenuating outliers, interpolating the samples to generate a signal, band pass filtering the signal, and downsampling. Processor 314 may also generate a kurtosis metric signal at step 2204 and a DSD metric signal at step 2206 in a similar manner.

At steps 2208, 2210, and 2212 an autocorrelation sequence may be generated for each morphology metric signal, e.g., the down metric signal, kurtosis metric signal, and DSD metric signal, respectively. Autocorrelation is the cross-correlation of a signal with itself, and to the extent that the underlying signal includes regular or repeating patterns the peaks of the autocorrelation may correspond to periodic components of the underlying signal. The autocorrelations of the morphology metric signals may be utilized to determine respiration information such as respiration rate as described herein. However, a single autocorrelation sequence corresponding to a single autocorrelation metric may not provide sufficient information to determine the respiration information with a desired accuracy or certainty. Accordingly, a plurality of autocorrelation sequences corresponding to respective morphology metric signals may be utilized to determine respiration information. The formula for the autocorrelation is the following:

$$R_{xx}(m) = \sum_{n \in S} x(n) \times (n-m), \text{ for } m = -M, \ldots, M$$

where:
S = the signal support of the finite segment;
M = the maximum lag computed for the autocorrelation.

For real signals with a maximum point located at the central point of the autocorrelation (i.e., where the signal is being compared directly with itself without any time lag) the autocorrelation sequence may be symmetric about the central point. Accordingly, it may be possible to calculate the autocorrelation for one half of the overall lag about zero (e.g., from −M to 0, or from 0 to M) and duplicate the result about the central point. Accordingly, the autocorrelation sequence may be calculated as follows:

$$R_{xx}(m) = \begin{cases} \sum_{n=0}^{\min(\max(L-m,0),L)} x(n+m)x(n), & \text{for } m = 0, \ldots, M \\ R_{xx}(-m), & \text{for } m = -M, \ldots, -1 \end{cases}$$

Figure 23:
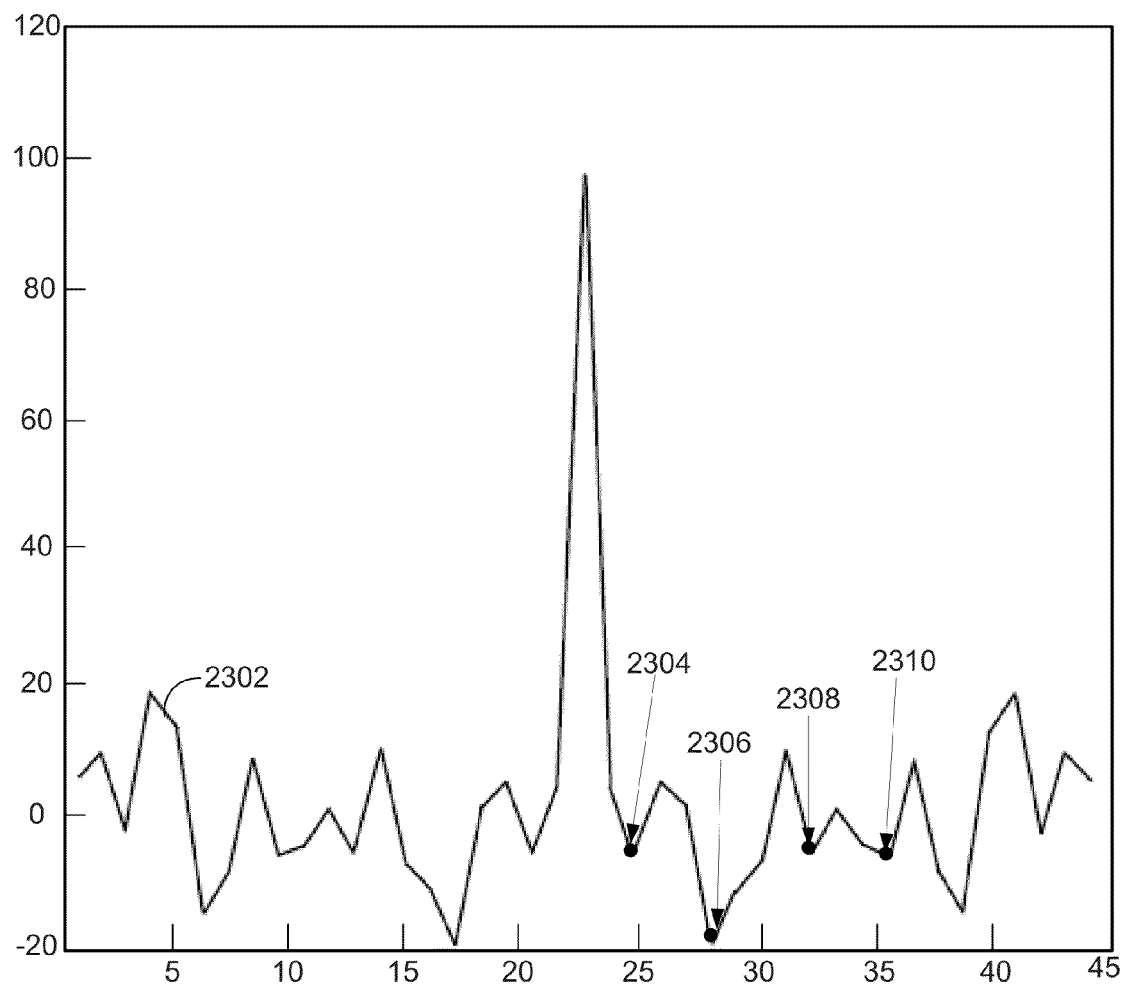
FIG. 23 depicts aspects of determining an illustrative autocorrelation metric from an autocorrelation sequence in accordance with some embodiments of the present disclosure.

At steps 2214, 2216, and 2218 an autocorrelation metric may be calculated for each of the autocorrelation sequences, which in an exemplary embodiment may be a down metric autocorrelation sequence, kurtosis metric autocorrelation sequence, and DSD metric autocorrelation sequence. An autocorrelation metric may quantify the regularity or periodicity of the underlying morphology metric signal based on the autocorrelation sequence. FIG. 23 depicts an exemplary autocorrelation sequence 2302. The abscissa of FIG. 23 is in units of seconds and spans an exemplary 45 second analysis window for a complete autocorrelation sequence, while the ordinate may represent the magnitude of the autocorrelation sequence. As described above, the autocorrelation sequence may be symmetric about the central or maximum point.

The central point of the autocorrelation sequence corresponds to the underlying morphology signal compared with itself without a time lag. The remaining points of the autocorrelation sequence may indicate the regularity or periodicity of the signal. It will be understood that any suitable analysis of the autocorrelation signal may be performed to analyze the regularity or periodicity of the underlying signal. For example, the autocorrelation sequence will have larger magnitude (positive or negative) repeating peaks if a signal is regular or periodic. Accordingly, the peaks may be utilized to calculate an autocorrelation metric which is representative of the regularity or periodicity of the morphology metric signal. In an exemplary embodiment the first four local minima 2304, 2306, 2308, and 2310 to the right of the central point may be selected. Because the autocorrelation sequence is symmetric, local minima to the left of the central point should be identical. If there are fewer than four local minima (e.g., due to a low respiration rate or if the usable portion of the morphology metric signal is limited) then all of the local minima to the right of the central point may be used to calculate the autocorrelation metric.

In an exemplary embodiment the local minima 2304, 2306, 2308, and 2310 may be normalized in any suitable manner, e.g., by dividing the magnitude of each of local minima 2304, 2306, 2308, and 2310 by the magnitude of the central point. A threshold may be calculated in any suitable manner. Any normalized local minima that do not exceed a threshold may be discarded. It will be understood that the autocorrelation metric may be calculated in any suitable manner from the normalized minima. For example, the resulting normalized local minima may be averaged to calculate the autocorrelation metric. An autocorrelation metric may be calculated in this manner for each autocorrelation sequence.

Referring again to FIG. 22A, once the autocorrelation metrics are calculated at steps 2214, 2216, and 2218, each of the autocorrelation sequences may be filtered with previous filtered autocorrelation sequences 2226, 2228, and 2230 at steps 2220, 2222, and 2224. Exemplary previous filtered autocorrelation sequences 2226, 2228, and 2230 may be the filtered autocorrelation sequences for a previous set of received data, e.g., the 45 second analysis window established by the previous 5 seconds of received PPG data. Filtering of the autocorrelation sequences may be performed in any suitable manner. In an exemplary embodiment, processor 314 may calculate a filter weight for each autocorrelation sequence based on the autocorrelation metric and a time ratio. The time ratio may be based on the length of the usable portion of the analysis window divided by the length of the analysis window. The filter weight may be calculated for each autocorrelation sequence by multiplying each autocorrelation metric and the time ratio. If the resulting filter weight exceeds a predetermined limit such as 1, the filter weight may be set to the predetermined limit. In addition, because the filter is an infinite impulse response filter, the filter weight (wt) may be phased in during startup. The filter weight may be phased in using any suitable technique, such as the following:

$$wt = \max\left(wt, \frac{1}{\text{number of points processed}}\right)$$

For example, for the first point to be processed, the weight will be set to 1, since the filter weight is also limited to 1. For the second point, the filter weight will be compared to 0.5, and so on until the filter weight exceeds the threshold and is used to calculate the remaining points of the filtered autocorrelation sequence. Once the filter weight is calculated, each point of the autocorrelation sequence may filtered in an infinite impulse response filter with the corresponding value from the previous filtered correlation sequence as follows:

FilteredSeq=wt*NewSeq+(1−wt)*PrevSeq where:
FilteredSeq=Filtered Autocorrelation Sequence;
wt=Filter Weight;
NewSeq=Autocorrelation Sequence;
PrevSeq=Previous Filtered Autocorrelation Sequence.

Processor 314 may also calculate a sequence age for each filtered autocorrelation sequence. The sequence age may be calculated in any suitable manner. In an exemplary embodiment, the sequence age may be based on the filter weight, the age of the previous filtered autocorrelation sequence, and the age of the autocorrelation sequence as follows:

SequenceAge=wt*CurrentAge+(1−wt)*PrevAge where:
SequenceAge=Filtered Autocorrelation Sequence Age;
wt=Filter Weight;
CurrentAge=Autocorrelation Sequence Age;
PrevAge=Previous Filtered Autocorrelation Sequence Age.

Once the filtered autocorrelation sequences and corresponded sequence ages have been calculation, processing may continue as depicted in FIG. 22B. Processor 314 may calculate a combination weight for each of the filtered autocorrelation sequences at steps 2232, 2234, and 2236. Each of the filtered autocorrelation sequences may be based on a different morphology metric signal and each morphology metric signal captures respiration information in a different manner. A combination weight for each filtered autocorrelation sequence may be calculated to adjust the relative emphasis of each of the filtered autocorrelation sequences in calculating respiration information. The combination weight may be calculated in any suitable manner to modify the relative weight of each of a plurality of autocorrelation sequences in a manner to accurately determine respiration information. In an exemplary embodiment a combination weight may be representative of the regularity of the autocorrelation metric as well as consistency of the filtered autocorrelation sequence over time. For each filtered autocorrelation sequence the weight of the current sequence ($w_{new}$) may be calculated based on the autocorrelation metric and a Pearson correlation coefficient:

$$W_{new}=(A_x+r)^{12}$$

where:
$A_x$=autocorrelation metric;
r=Pearson correlation coefficient.

The Pearson correlation coefficient may be calculated as follows:

$$r = \frac{1}{n-1} \sum_{i=1}^{n-1} \left(\frac{X_i - \overline{X}}{s_X}\right)\left(\frac{Y_i - \overline{Y}}{s_Y}\right)$$

where:
X=current filtered autocorrelation sequence;
Y=previous filtered autocorrelation sequence;
$S_X$, $S_Y$=sample standard deviation; and
$\overline{X}$, $\overline{Y}$=sample mean.

$$\left(\frac{X_i - \overline{X}}{s_X}\right), \left(\frac{Y_i - \overline{Y}}{s_Y}\right) = \text{standard score}$$

Once the weight of the current sequence is calculated, the combination weight may be calculated as follows:

$$w_C = (b * w_{new} + (1-b) * w_{Cprev}) * t\text{Ratio}$$

where:
$w_C$=combination weight;
$w_{new}$=weight of the current sequence;
$w_{Cprev}$=weight of the previous sequence;
b=0.01*tRatio; and
tRatio=time ratio.

A combination weight $w_{c-D}$ for the filtered autocorrelation sequence associated with the down metric signal may be calculated at step 2232, a combination weight $w_{c-K}$ for the filtered autocorrelation sequence associated with the kurtosis metric signal may be calculated at step 2234, and a combination weight $w_{c-DSD}$ for the filtered autocorrelation sequence associated with the DSD metric signal may be calculated at step 2236. It will be understood that an autocorrelation metric may be calculated in a similar manner for any other autocorrelation sequence associated with any other morphology metric. At step 2238, processor 314 may generate a combined autocorrelation sequence from the filtered autocorrelation sequences based on the combination weights. For example, the combined autocorrelation sequence may be generated according to the following:

$$\text{Combined Sequence} = \frac{(w_{C-D} * S_D + w_{C-K} * S_K + w_{C-DSD} * S_{DSD})}{(w_{C-D} + w_{C-K} + w_{C-DSD})}$$

where:
$w_{C-D}$=combination weight for down metric sequence;
$w_{C-K}$=combination weight for kurtosis sequence;
$w_{C-DSD}$=combination weight for DSD sequence;
$S_D$=filtered down sequence;
$S_K$=filtered kurtosis sequence; and
$S_{DSD}$=filtered DSD sequence.

Processor 314 may calculate a combined autocorrelation age for the combined autocorrelation sequence. The combined autocorrelation age may be calculated in any suitable manner. In an exemplary embodiment the combined autocorrelation age may be based on the previously calculated signal age and combination weight for each of the autocorrelation sequences as follows:

$$\text{CombineAge} = \frac{(w_{C-D} * \text{Age}_D + w_{C-K} * \text{Age}_K + w_{C-DSD} * \text{Age}_{DSD})}{(w_{C-D} + w_{C-K} + w_{C-DSD})}$$

where:
$w_{C-D}$=combination weight for down metric sequence;
$w_{C-K}$=combination weight for kurtosis sequence;
$W_{C-DSD}$=combination weight for DSD sequence;
$\text{Age}_D$=age of down sequence;
$\text{Age}_K$=age of kurtosis sequence; and
$\text{Age}_{DSD}$=age of DSD sequence.

At step 2240 processor 314 may derive respiration information from the combined autocorrelation sequence. Respiration information may be derived from the combined autocorrelation sequence in any suitable manner. In one exemplary embodiment of deriving respiration information from the combined autocorrelation sequence, processor 314 may utilize a wavelet transform to derive respiration information. Although a number of wavelet parameters may be utilized to derive respiration information from the combined autocorrelation sequence, exemplary parameters are described below. An exemplary wavelet transform method may be a continuous wavelet transform and an exemplary wavelet may be a real Morlet wavelet. Scale parameters may be selected in any manner that captures respiration information. For example, a characteristic frequency range may be selected based on a range of frequency for respiration, such as 0.05 Hz (3 breaths per minute) to 1.0 Hz (60 breaths per minute). The scale resolution may be selected to determine the number of scales that are generated by the continuous wavelet transform. A smaller scale resolution (i.e., a larger number of scales corresponding to the characteristic frequency range of the corresponding wavelets) may be more computationally intensive but may yield greater accuracy in deriving respiration information. In an exemplary embodiment 60 scales may correspond to the characteristic frequency range of the corresponding wavelets.

Figure 24:
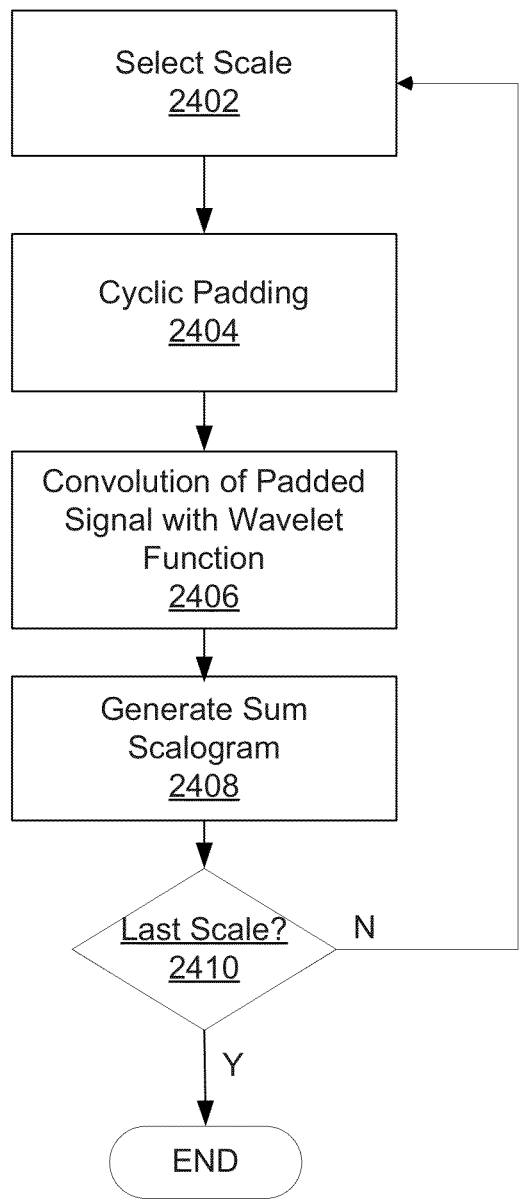
FIG. 24 is a flow diagram showing illustrative steps for generating a scalogram from a combined autocorrelation sequence in accordance with some embodiments of the present disclosure.

Steps for generating a scalogram from the combined autocorrelation sequence are depicted in FIG. 24. In the discussion of the technology which follows herein, the "scalogram" may be taken to include all suitable forms of rescaling including, but not limited to, the original unscaled wavelet representation, linear rescaling, any power of the modulus of the wavelet transform, or any other suitable rescaling. In addition, for purposes of clarity and conciseness, the term "scalogram" shall be taken to mean the wavelet transform, T(a,b) itself, or any part thereof. For example, the real part of the wavelet transform, the imaginary part of the wavelet transform, the phase of the wavelet transform, any other suitable part of the wavelet transform, or any combination thereof is intended to be conveyed by the term "scalogram." The steps described are exemplary only, and it will be understood that some of the steps may be rearranged or omitted, and that additional steps may be added. These steps may be repeated for each scale to generate the scalogram. It will be understood that the term scalogram may refer to any suitable scalogram or modification thereof, e.g., a combined sum scalogram or sum scalogram vector as described herein. Although the steps of FIG. 24 are described as being performed by processor 314, it will be understood that one or more of pre-processor 312, post-processor 316, or other processing circuitry may perform some or all of the processing steps. At step 2402, processor 314 may select the scale to be generated. In an exemplary embodiment, the first scale may be associated with the highest characteristic frequency of the characteristic frequency range, e.g., 1.0 Hz. At step 2404, processor 314 may perform cyclic padding on the combined autocorrelation sequence.

Figure 25:
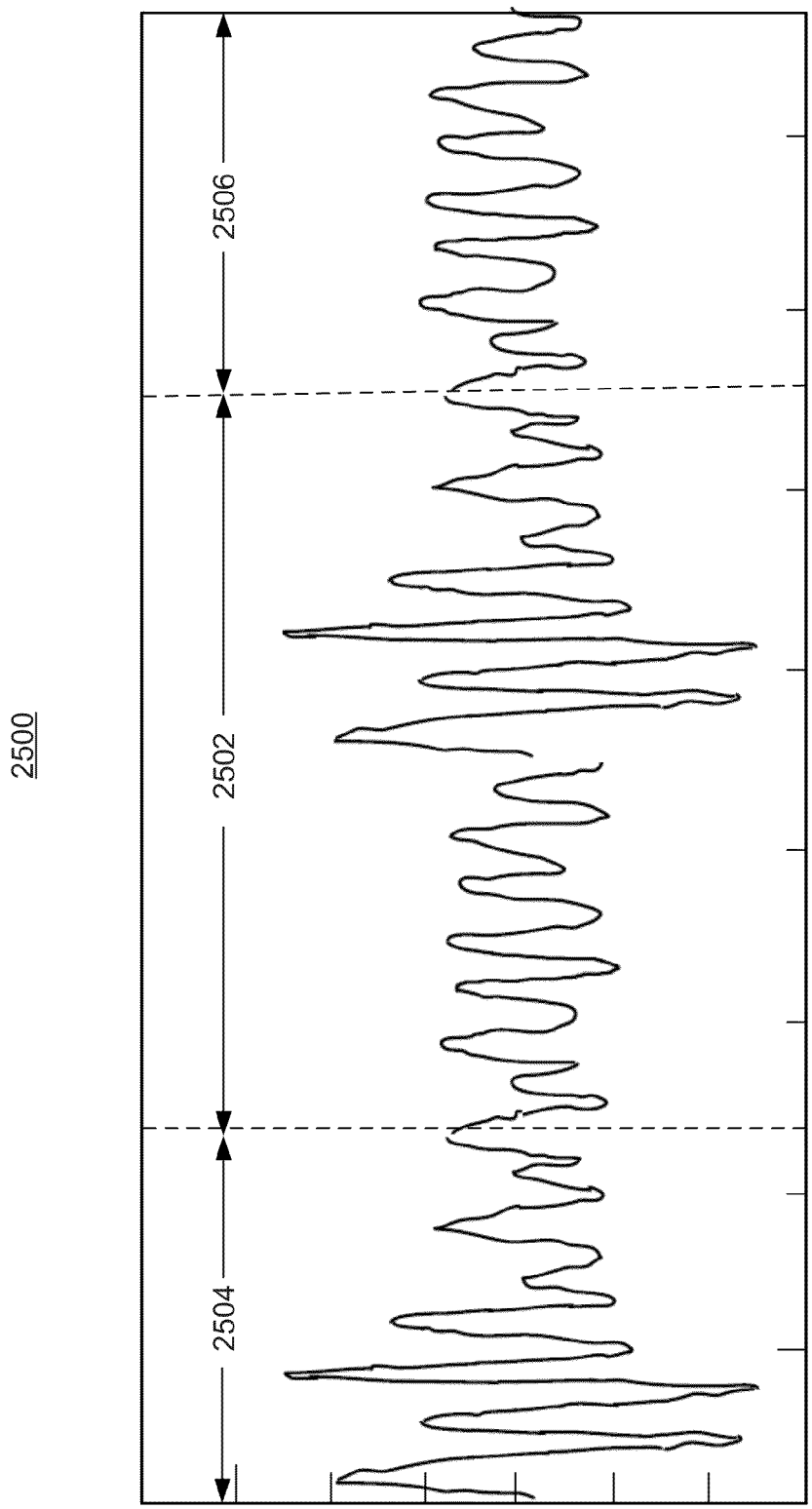
FIG. 25 depicts cyclical padding of a combined autocorrelation sequence in accordance with some embodiments of the present disclosure.

Cyclical padding is depicted in more detail in FIG. 25. Signal 2502 may represent the combined autocorrelation sequence. It may be desirable to provide padding on either or both sides of signal 2502 for purposes of performing the wavelet transform, e.g., to account for edge effects when performing a convolution with the mother wavelet. Padding may be performed in any suitable manner. In an exemplary embodiment, padding may be performed by repeating a portion of the original signal and attaching the repeated portion to the signal. For example, padding 2504 may correspond to the later samples of signal 2502 and may attach to the beginning of signal 2502. In an exemplary embodiment padding 2504 may be equal to the final 50% of signal 2502. Padding 2506 may correspond to the earlier samples of signal 2502 and may attach to the end of signal 2502. In an exemplary embodiment padding 2506 may be equal to the initial 50% of signal 2502.

It may also be desirable to dynamically scale the padding to correspond to the length of the wavelet. Dynamic scaling may be performed in any suitable manner to modify the padding length relative to the wavelet length. The wavelet length increases with higher scale values. Accordingly, in an exemplary embodiment, for each scale value a new pad length may be calculated and a new padded signal created based on the wavelet length. For example, an original signal of length N may be expressed as follows:

$$x=[x(x(0),x(1),x(2),\ldots x(N-1)]$$

If m represents the amount of padding, the signal with padding may be expressed as follows:

$$x=[x(N-m),x(N-m+1),\ldots x(N-1),x(0),x(1),\ldots x(N-1),x(0),x(1)\ldots x(m-1)]$$

The resulting signal length L for the padded signal is 2*m+N. Dynamic scaling may modify the m term based on the wavelet length. In an exemplary embodiment, the padding length may be equal to 50% of the wavelet length. It will be understood that other relationships between the padding length and wavelet length may be selected.

Referring again to FIG. 24, at step 2406 processor 314 may perform a wavelet transform such as a continuous wavelet transform. The continuous wavelet transform of a signal x(t) in accordance with the present disclosure may be defined as:

$$T(a,b) = \frac{1}{\sqrt{a}} \int_{-\infty}^{\infty} x(t)\psi^*\left(\frac{t-b}{a}\right) dt$$

where:
a=scale value;
b=shift parameter; and
ψ(t)=wavelet function and * denotes complex conjugate.

In an embodiment the wavelet transform may be defined as:

$$WT(a,b) = \frac{1}{\sqrt{a}} \sum_{n \in S} x_{new}(n)\psi^*\left(\frac{n-b}{a}\right) \Delta T$$

where:
ΔT sampling interval;
$x_{new}$=padded combined autocorrelation sequence; and
S=support of the signal.

If a real Morlet wavelet is used, it may not be necessary to utilize the complex conjugate of the wavelet function.

Figure 26:
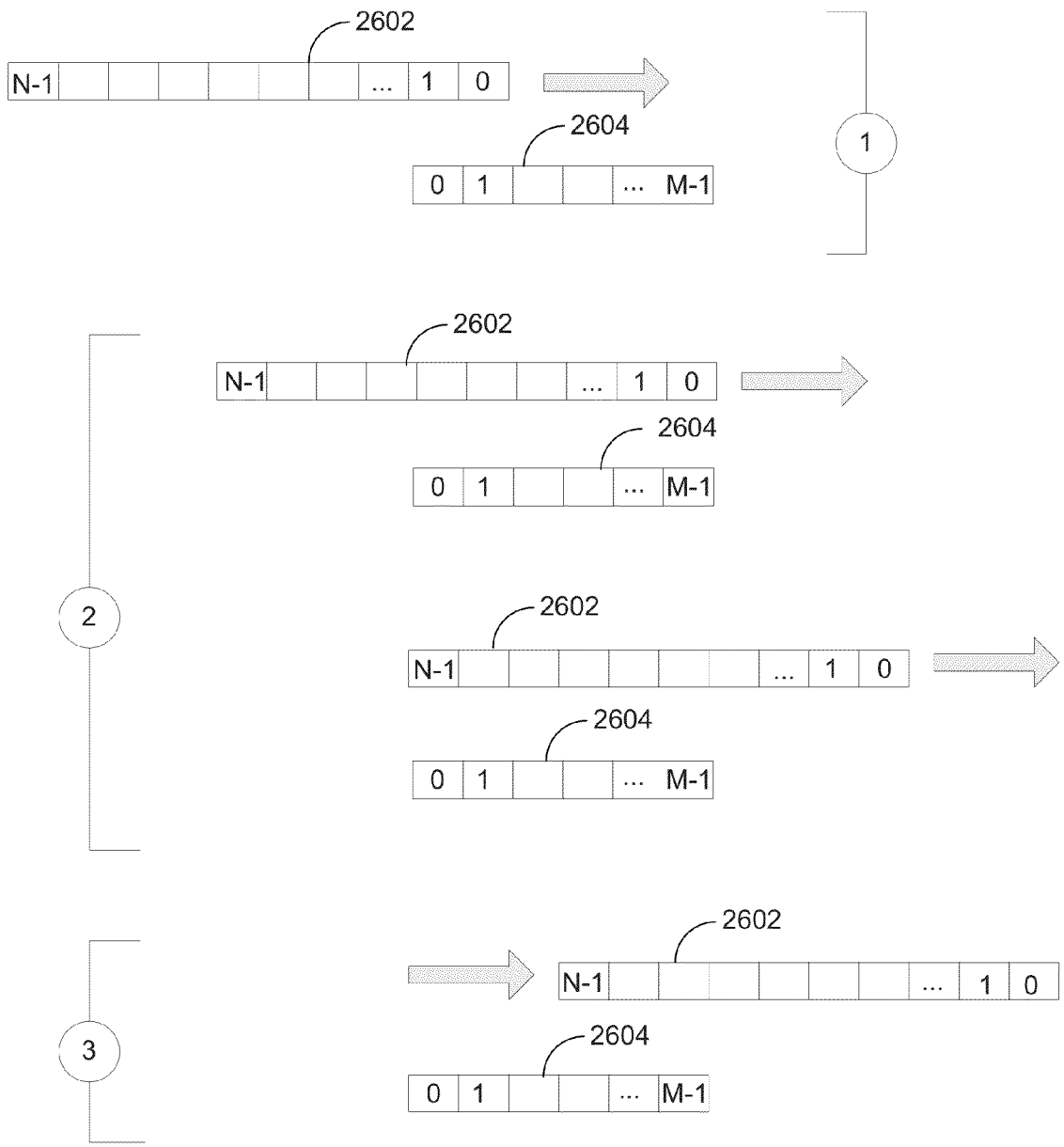
FIG. 26 depicts convolution of a padded combined autocorrelation sequence with a mother wavelet in accordance with some embodiment of the present disclosure.

FIG. 26 depicts aspects of the convolution of the padded combined autocorrelation sequence 2602 with the wavelet function 2604. It will be understood that convolution of the padded combined autocorrelation sequence 260 with the wavelet function 2604 may be performed in any suitable manner. In an exemplary embodiment, padded combined autocorrelation sequence 2602 may have N samples and wavelet function 2604 may have M samples. The convolution may be depicted as the padded combined autocorrelation sequence 2602 incrementally translating across the wavelet function 2604 and being combined where the functions overlap at each translation point. Region 1 of FIG. 26 depicts an example of a first region where there is not complete overlap between the signals, i.e., the first M−1 samples of the convolution. Region 2 of FIG. 26 depicts examples of a second region in which there is complete overlap of the signals, i.e., the M through N−1 samples of the convolution. Region 3 of FIG. 26 depicts an example of a third region where there is not complete overlap between the signals, i.e., the N through M+N−2 samples of the convolution.

At the edges of the convolution (e.g., some or all of regions 1 and 3 as described above) there may be an undesirable edge effect. The high fidelity portion of the convolution result may be located in the central portion of the convolution. It will be understood that the edge effect may be compensated for in any suitable manner. In an exemplary embodiment, only some portion of the central portion of the signal may be selected for the convolution result, such as the middle N samples or the portion of the samples corresponding to the combined autocorrelation sequence prior to padding. In the latter example, any edge effects may occur only for the padded portions of the combined autocorrelation sequence based on the pad size being equivalent to one half of the wavelet size. For ease of calculation, only the desired portions of the convolution may be calculated.

Referring again to FIG. 24, the result of the convolution may be summed to generate a sum scalogram corresponding to the particular scale at step 2408. It will be understood that the sum scalogram may be calculated in any suitable manner. The sum scalogram may be utilized to determine respiration information as described herein. At step 2410, processor 314 may determine if there are additional scales to process. If so, another scale may be selected at step 2402 and the process may repeat until all scales are processed. The result may be a combined sum scalogram.

Referring again to FIG. 22B, once the continuous wavelet transform has been performed and the combined sum scalogram generated, processor 314 may estimate respiration information at step 2242. It will be understood that respiration information may be estimated form the combined sum scalogram in any suitable manner. In an exemplary embodiment, processor 314 may sum across all scales of the combined sum scalogram to create a sum scalogram vector. The sum scalogram vector may be normalized, e.g., such that the scale having the highest energy has a value of 1.

Figure 27:
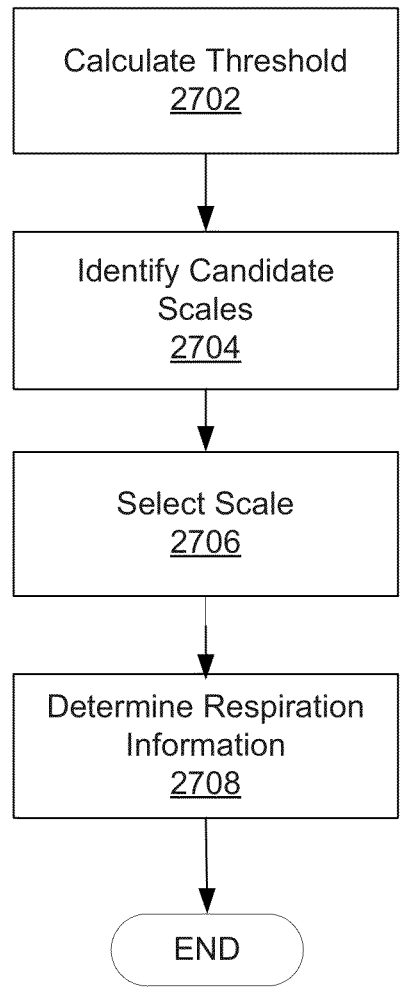
FIG. 27 is a flow diagram showing illustrative steps for deriving respiration information from a sum scalogram vector in accordance with some embodiments of the present disclosure.

FIG. 27 depicts exemplary steps for determining respiration information from the sum scalogram vector. It will be understood that the order of the steps of FIG. 27 may be modified, steps may be omitted, and additional steps may be added. At step 2702, a threshold may be calculated for the sum scalogram vector. The threshold may be calculated in any suitable manner. In an exemplary embodiment, the threshold may be based on the maximum value in the combined sum scalogram, e.g., at 50% of the maximum value. At step 2704, processor 314 may identify candidate scales from the sum scalogram vector based on the threshold. For example, each local maxima of the sum scalogram vector may be compared to threshold. Only the local maxima that exceed the threshold may be candidate scales. Any local maxima that do not exceed the threshold may be disregarded.

At step 2706, processor 314 may select the candidate scale to be used to determine respiration information. It will be understood that the candidate scale may be selected in any suitable manner. In an exemplary embodiment, the selected scale may be the lowest scale value that exceeds the threshold. At step 2708, respiration information such as respiration rate may be calculated from the selected scale. In the exemplary embodiment described above the scales may correspond to the characteristic frequency of the corresponding wavelets, e.g., a characteristic frequency range of 0.05 Hz-1.0 Hz. A scale value of zero may correspond to a minimum pulse period (e.g., corresponding to a characteristic frequency of 1.0 Hz for the corresponding wavelet) while a scale value of 60 may correspond to a maximum pulse period (e.g., corresponding to a characteristic frequency of 0.05 Hz for the corresponding wavelet). The pulse period for the selected scale may be calculated based on the maximum or minimum pulse period, the scale number, and the scale interval. For example, a scale value of 50 may correspond to a pulse period of 4.73 seconds, which may be equivalent to 12.66 breaths per minute.

Figure 28:
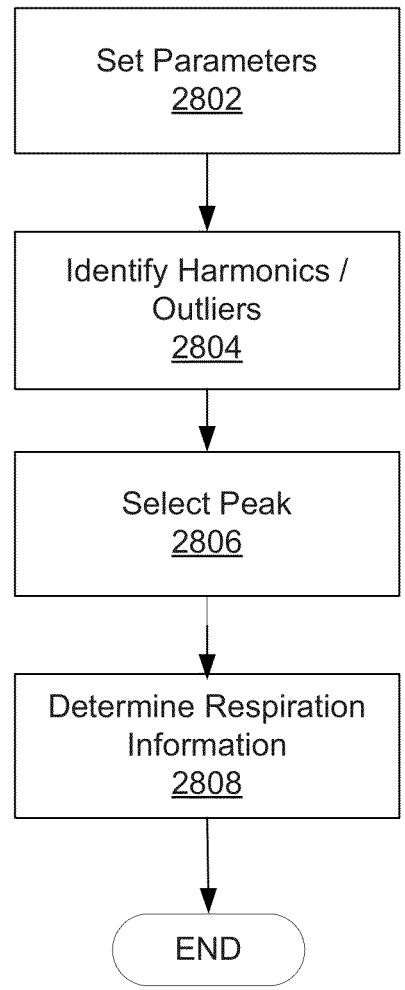
FIG. 28 is a flow diagram showing illustrative steps for deriving respiration information from a combined autocorrelation sequence in accordance with some embodiments of the present disclosure.
Figure 29:
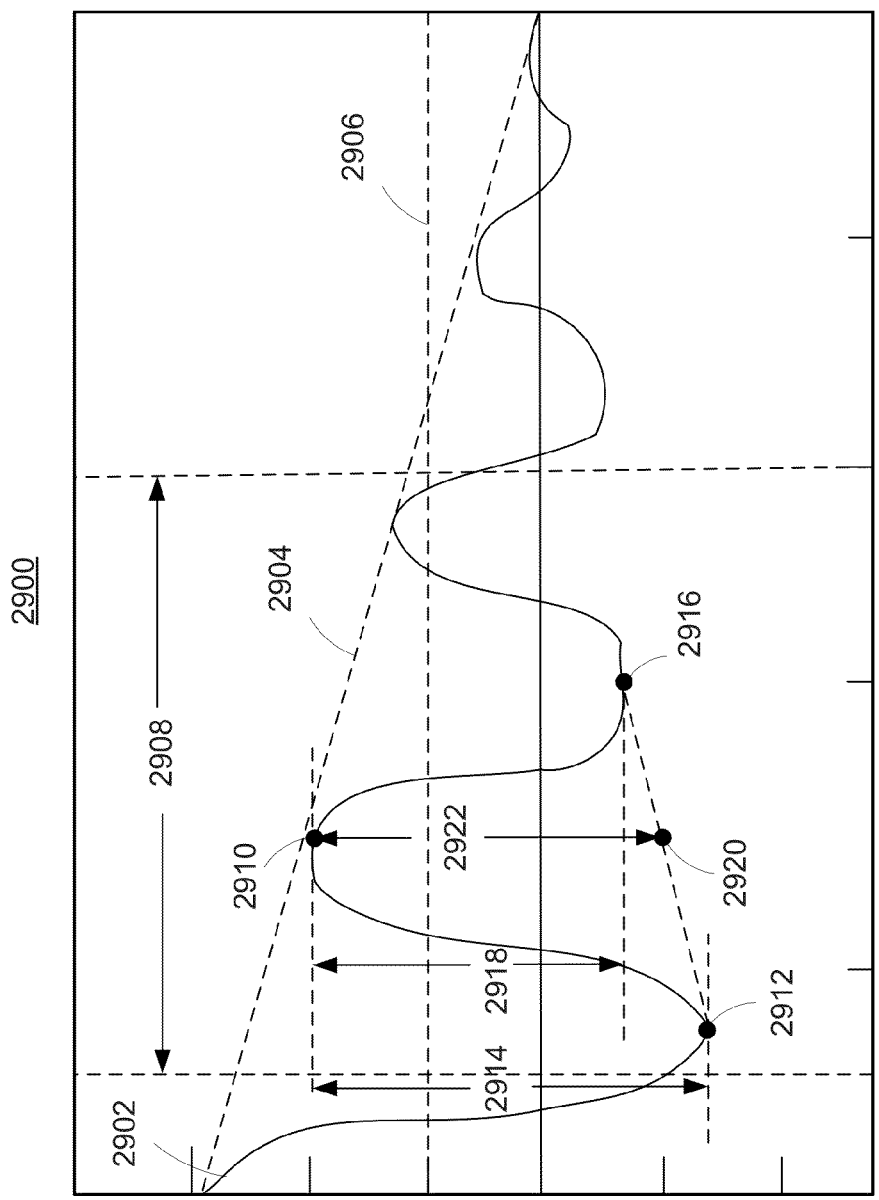
FIG. 29 shows a graph illustrating analysis of a combined autocorrelation sequence in accordance with some embodiments of the present disclosure.
Figure 30:
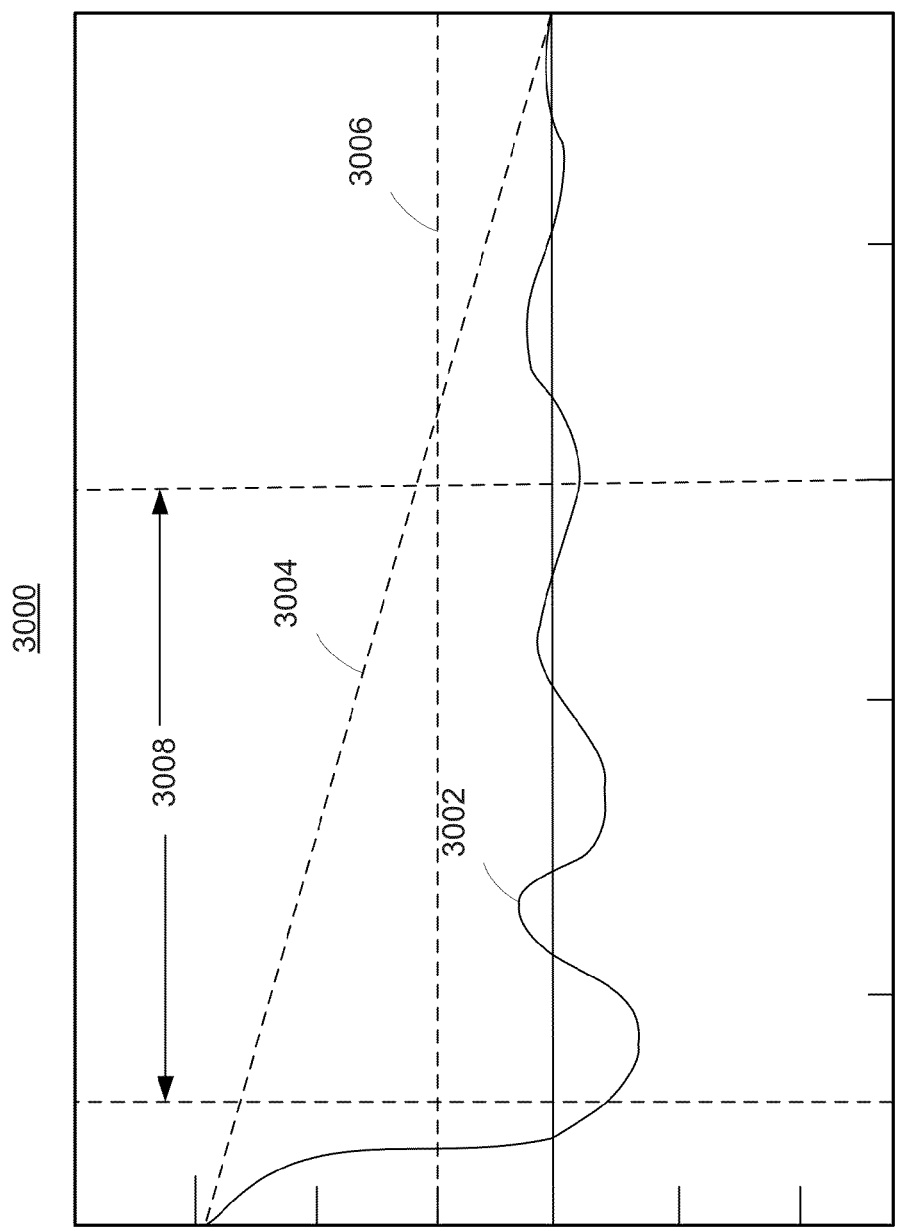
FIG. 30 shows a graph illustrating analysis of a combined autocorrelation sequence having limited respiration information in accordance with some embodiments of the present disclosure.
Figure 31:
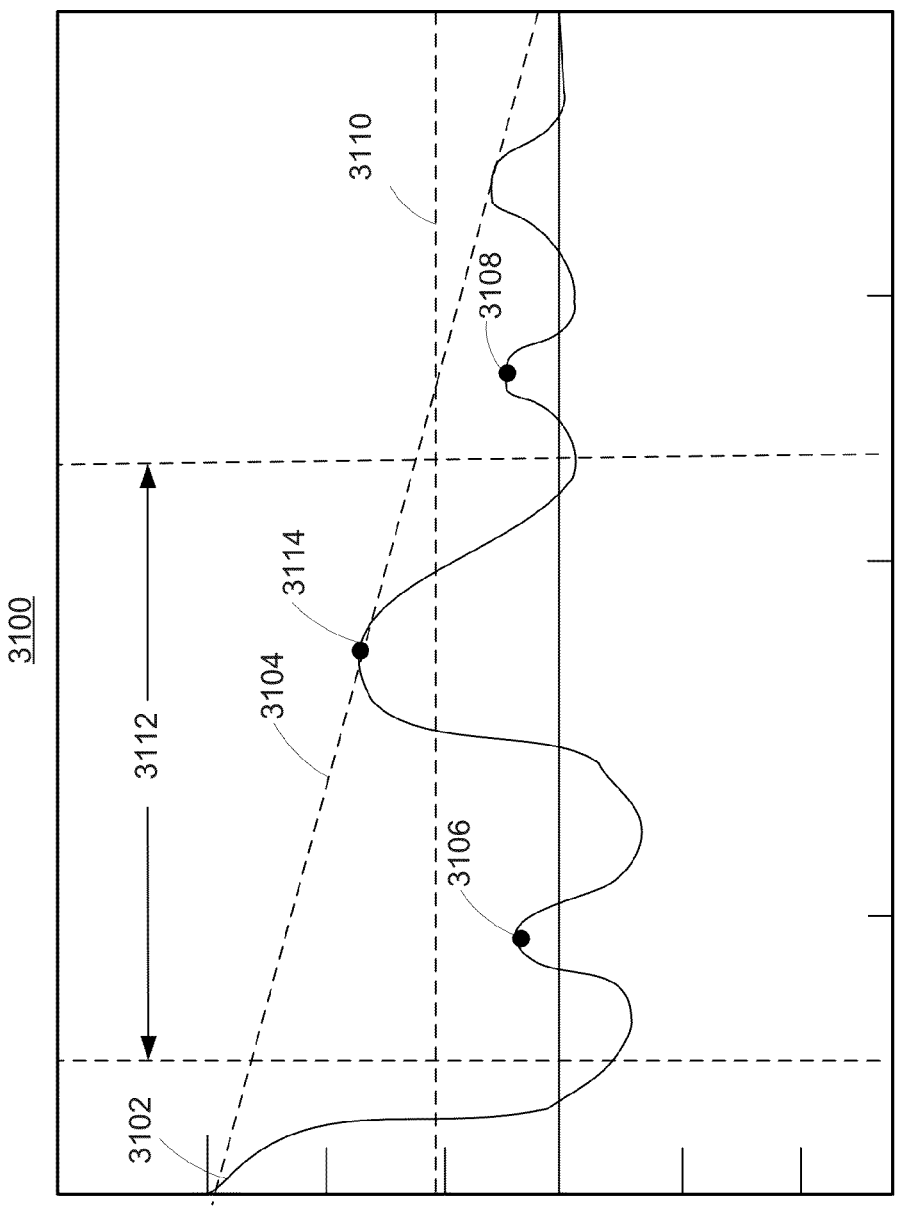
FIG. 31 shows a graph illustrating analysis of a combined autocorrelation sequence having harmonics in accordance with some embodiments of the present disclosure.

In another embodiment, respiration information may be calculated based on identifying suitable portions (e.g., peaks) of the combined autocorrelation signal. At steps 2240 and 2242, processor 314 may determine respiration information directly from the combined autocorrelation sequence. Respiration information may be determined from the combined autocorrelation sequence in any suitable manner. In an exemplary embodiment, respiration information may be determined from the combined autocorrelation sequence based on the steps of FIG. 28. At step 2802, processor 314 may set parameters for determining respiration information from the combined autocorrelation sequence. Exemplary combined autocorrelation sequences are depicted in FIG. 29, FIG. 30, and FIG. 31. The combined autocorrelation sequence may be symmetric about the point where the sequence directly overlaps with itself, i.e., the right side and left side of the combined autocorrelation sequence may be the same. Determination of respiration information may be simplified by looking only at one side of the combined autocorrelation sequence, e.g., the right side as is depicted in FIG. 29, FIG. 30, and FIG. 31. The abscissa of each of FIG. 29, FIG. 30, and FIG. 31 may be in units of time, and the ordinate may be in units of amplitude.

FIG. 29 depicts an exemplary combined autocorrelation sequence 2902 that may be directly analyzed to determine respiration information. The combined autocorrelation sequence 2902 may have a series of peaks that appear at regular intervals and decrease in magnitude over time. Line 2904 may be indicative of a rate of decay of the combined autocorrelation sequence 2902 and may define an expected autocorrelation envelope. The peaks of the combined autocorrelation sequence 2902 may roughly align with the rate of decay, which may be indicative of a signal from which respiration information may be accurately determined.

FIG. 30 depicts an exemplary combined autocorrelation sequence 3002 that may be directly analyzed to determine respiration information. The combined autocorrelation sequence 3002 may have a series of peaks that appear at regular intervals and decrease in magnitude over time. Line 3004 may be indicative of a baseline rate of decay of a combined autocorrelation sequence and may define an expected autocorrelation envelope, which does not correspond to the rate of decay of combined autocorrelation sequence 3002. The lower magnitude peaks are indicative of a signal that does not have significant periodic characteristics over the analysis window, and may not be suitable for determining respiration information. It will be understood that there may be many reasons that the underlying signal does not display significant periodic characteristics, for example the signal may have a significant source of nonstationarity, e.g., as a result of step change, phase irregularity, or a gradual change in respiration rate.

FIG. 31 depicts an exemplary combined autocorrelation sequence 3102 that may be directly analyzed to determine respiration information. The combined autocorrelation sequence 3102 may have a series of peaks that appear at regular intervals and decrease in magnitude over time. Line 3104 may be indicative of a baseline rate of decay of a combined autocorrelation sequence and may define an expected autocorrelation envelope, which may correspond to a number of the peaks of combined autocorrelation sequence 3102. Other peaks, which are indicated by points 3106 and 3108, may be indicative of harmonic components of combined autocorrelation sequence 3102.

Referring again to FIG. 28, at step 2802 processor 314 may set parameters for determining respiration information from the combined autocorrelation sequence. It will be understood that there are numerous parameters that may be set such as thresholds and relevant ranges of interest. It will also be understood that such parameters may be set in any suitable manner to improve the determination of respiration information. In one exemplary embodiment a threshold may be set for the magnitude of the peaks that may be considered to determine respiration information. A threshold may be set such that peaks corresponding to harmonics (e.g., peaks 3106 and 3108 of FIG. 31) and low magnitude peaks of signals that are irregular or non-periodic (e.g., signal 3002 of FIG. 30) are ignored for determining respiration information. Exemplary thresholds are depicted as threshold 2906 in FIG. 29, threshold 3006 in FIG. 30, and threshold 3110 in FIG. 31. The threshold may correspond to a maximum amplitude as depicted by thresholds 2906, 3006, and 3110, may be values that may be compared to amplitude differences (e.g., in a peak to trough embodiment described herein, or may be determined in any other suitable manner. Harmonic peaks may not correspond to respiration information (respiration rate), while irregular or non-periodic signals may not have a signal that accurately captures respiration information. Setting a threshold may avoid choosing such peaks. Other amplitude thresholds may also be set, such as a difference threshold for two consecutive peaks. For example, a difference threshold may require that for a peak to be considered for purposes of determining respiration information, the amplitude of the peak must exceed the amplitude of the subsequent peak by at least a threshold, e.g., 70%. In another exemplary embodiment a difference threshold may be set based on the expected decay characteristics of the combined autocorrelation sequence.

Another exemplary parameter may be a relevant range of interest, e.g. on the time scale of the combined autocorrelation sequence. The peaks of the combined autocorrelation sequence may correspond to instances where the underlying signal (e.g., a morphology metric signal) has been translated in time and is similar to itself, which may demonstrate a periodic or regular signal. Thus the time between peaks that are representative of the respiration information may be equivalent to the period of the respiration, which may be utilized to determine respiration rate (e.g. the frequency of respiration). In an exemplary embodiment a range of interest may be set to correspond to a respiration rate, such as from 4 to 40 breaths per minute. An exemplary range of interest is depicted as range of interest 2908 in FIG. 29, range of interest 3008 in FIG. 30, and range of interest 3112 in FIG. 31. It will be understood that the range of interest may be set in any suitable manner. For example, in another embodiment the range of interest may be based upon a maximum time between any two consecutive peaks.

Referring again to FIG. 28, at step 2804 processor 314 may identify harmonics and outliers. As was discussed above, a threshold may exclude many harmonic or outlying values because the magnitude of the autocorrelation is less likely to exceed the threshold at such points. In another exemplary embodiment harmonics may be identified based on expected harmonic values. A largest peak of the combined autocorrelation sequence may be likely to correspond to respiration information. Other peaks may occur at intervals that would be expected to be harmonics, e.g., at approximately 50% of the time of the largest peak. For example, in FIG. 31 a largest peak may correspond to point 3114. Other peaks at points 3106 and 3108 may approximately correspond to 50% of the period associated with largest peak 3114 and may be classified as likely harmonic peaks. Any harmonic peaks or other outliers that are identified may be excluded from consideration as potential selected peaks.

At step 2806 processor 314 may select a peak associated with a respiration rate. It will be understood that selecting the peak may be performed in any suitable manner, such as selecting the first peak to the right of the vertical axis or a maximum peak value, e.g., peak 2910 in FIG. 29. In another exemplary embodiment, selecting the peak may be based on any parameters that were set in step 2802 such as a threshold and a range of interest. For example, peak 2910 in FIG. 29 may exceed threshold 2906 and be within a range of interest 2908, peak 3114 may exceed threshold 3110 and be within range of interest 3112, and there may be no peak of combined autocorrelation sequence 3002 that exceeds threshold 2906 within range of interest 2908. Selecting the peak within a range of interest may be performed in any suitable manner, such as selecting the first peak within the range of interest or selecting the peak with the largest amplitude.

In another exemplary embodiment, analysis of the peaks may be based on the peak to trough amplitude of the peak. The peak to trough amplitude may be based on any suitable points. In one exemplary embodiment, a peak to trough amplitude may be based on a selected peak and a preceding trough, as is depicted in by amplitude 2914 between peak 2910 and trough 2912 in FIG. 29. In another exemplary embodiment, a peak to trough amplitude may be based on a selected peak and a subsequent trough, as is depicted in by amplitude 2918 between peak 2910 and trough 2916 in FIG. 29. In another exemplary embodiment, a peak to trough amplitude may be based on a selected peak and a midpoint trough associated with the peak, as is depicted in by amplitude 2922 between peak 2910 and midpoint trough 2920 in FIG. 29. Once the peak to trough amplitude is determined for the peak, selecting a peak corresponding to respiration information may be performed in any suitable manner, such as comparing the amplitude of each peak within a range of interest to a threshold, and selecting a peak based on amplitude or relative position.

At step 2808, processor 314 may determine respiration information such as respiration rate based on the selected peak. It will be understood that respiration information may be determined in any suitable manner. In an exemplary embodiment the time value associated with the selected peak may be related to the period for respiration, which may be used to determine respiration information such as respiration rate. In another exemplary embodiment, one or more time differences between a selected peak and one or more other peaks may be related to the period for respiration, which may be used to determine respiration information such as respiration rate. Processor 314 may also calculate a confidence value associated with the determined respiration information. For example, a best fit line may be generated for the peaks of the combined autocorrelation sequence. The confidence value may be determined based on the variability of the best fit line in any suitable manner, such as based on a $R^2$ residual sum. In another exemplary embodiment processor 314 may assess the distribution of the time between adjacent peaks of the combined autocorrelation sequence. A higher variability for the distribution may be indicative of a lower confidence value.

Referring again to FIG. 22, the calculated respiration information (e.g., respiration rate) may be filtered at step 2244. A combined autocorrelation metric may be calculated for the combined autocorrelation sequence in the same manner as the individual autocorrelation sequences, e.g., based on four local minima values as described herein. The filter may utilize the combined autocorrelation metric to determine how much weight to place on the value of the current respiration information versus a previous value of filtered respiration information. The more regular the combined autocorrelation sequence, the more emphasis may be placed on the current respiration information. The filtered respiration information may be calculated as follows:

$$R_{filt} = R_{wt} * R_{new} + (1 - R_{wt}) * R'_{filt}$$

where:
$R_{filt}$=filtered respiration information;
$R_{wt}$=combined autocorrelation metric;
$R_{new}$=calculated respiration information; and
$R'_{filt}$=Previous filtered respiration information.

It will be recognized that filtering the value of the current respiration information with previous values of respiration information may be performed in any suitable manner. For example, a combined autocorrelation value may be calculated utilizing local maxima values or other parameters of the combined autocorrelation signal.

The combined autocorrelation metric may also be utilized to calculate an age for the filtered respiration information in any suitable manner. For example, the age may be calculated based on the combined autocorrelation age (calculated above) and the previous filtered respiration age as follows:

$$R_{age} = R_{wt} * \text{CombinedAge} + (1 - R_{wt}) * R'_{age}$$

where:
$R_{age}$=filtered respiration age;
$R_{wt}$=combined autocorrelation metric;
CombinedAge=age of combined autocorrelation sequence;
$R'_{filt}$=previous filtered respiration age.

Processor 314 may communicate information to post-processor 316, such as the filtered respiration information, filtered respiration age, and the time ratio. In an exemplary embodiment, post-processor 316 may calculate a display value from the value of current filtered respiration information and values for previous filtered respiration information.

In an exemplary embodiment, post-processor 316 may receive the filtered respiration information, filtered respiration age, and time ratio from processor 314. Post-processor 316 may also receive period variability and amplitude variability values from pre-processor 312. Post-processor 316 may generate display respiration information in any suitable manner. For example, display information may be based on the currently received information. In another example, the display information may be based on the received information as well as previously received information. In an exemplary embodiment, post-processor 316 may calculate the display respiration information from the filtered respiration information for the current analysis window and filtered respiration information for one or more previous analysis windows, e.g., the five previous analysis windows. A weight for each analysis window may be calculated from the period variability and amplitude variability for that analysis window as follows:

$$w(k) = \frac{P_{var}(k) - A_{var}(k)}{2}$$
$$w(k) = 1 - \min(w(k), 1)$$
$$w(k) = w(k)^{20}$$

where:
$P_{var}$=period variability;
$A_{var}$=amplitude variability; and
k=analysis window of the N total analysis windows, in ascending order from most recent analysis window to oldest analysis window.

Once a weight is calculated for each respective analysis window, the display value can be calculated by combining the values for the filtered respiration information based on the calculated weights as follows:

$$\text{Display Value} = \frac{\sum_{k=0}^{N-1} w(k) R_{filt}(k)}{\sum_{k=0}^{N-1} w(k)}$$

where:
w(k)=weight for the kth analysis window;
$R_{filt}$=filtered respiration information for the kth analysis window; and
N=total number of analysis windows in display value calculation.

The display value may be displayed, e.g., at display 28 of display monitor 26 as a respiration rate value.

Post-processor 316 may also calculate an age for the display value based on the weight and filtered respiration age associated with each analysis window as follows:

$$\text{Display Age} = \frac{\sum_{k=0}^{N-1} w(k)(R_{age}(k) + 5*k)}{\sum_{k=0}^{N-1} w(k)}$$

where:
m(k)=weight for the kth analysis window;
$R_{age}$=filtered respiration age for the kth analysis window;
N=total number of analysis windows in display value calculation.

The 5*k term takes into account that the filtered respiration age values associated with previous analysis windows have aged since the values were initially determined. It will be recognized that the display value and display age may be calculated in any suitable manner.

The foregoing is merely illustrative of the principles of this disclosure and various modifications may be made by those skilled in the art without departing from the scope of this disclosure. The above described embodiments are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

What is claimed is:

1. A method for determining physiological information, the method comprising:
generating, using processing equipment, a plurality of morphology metric signals based on a photoplethysmograph (PPG) signal;
generating, using the processing equipment, a plurality of autocorrelation sequences, wherein each autocorrelation sequence is derived from a respective one of the morphology metric signals; and
determining, using the processing equipment, the physiological information from the plurality of autocorrelation sequences.

2. The method of claim 1 wherein the plurality of morphology metric signals comprises a down metric signal, a kurtosis metric signal, and a DSD metric signal.

3. The method of claim 1 further comprising generating a plurality of autocorrelation metrics using the processing equipment, wherein each autocorrelation metric corresponds to one of the autocorrelation sequences.

4. The method of claim 3 wherein generating each of the plurality of autocorrelation metrics comprises:
identifying a plurality of local minima points for a corresponding autocorrelation sequence;
normalizing the local minima based on a peak of the corresponding autocorrelation sequence;
averaging the magnitudes of the normalized local minima points; and
generating the autocorrelation metric based on the averaging.

5. The method of claim 3 wherein generating each autocorrelation sequence further comprises:
generating an autocorrelation of the respective morphology metric signal;
calculating a ratio of the usable portion of the PPG signal;
calculating a filter weight based on the ratio and the autocorrelation metric; and
filtering the autocorrelation based on the filter weight to generate the autocorrelation sequence.

6. The method of claim 5 further comprising calculating a sequence age for each of the autocorrelation sequences based on the filter weight, a current age for the autocorrelation sequence, and a previous age for the autocorrelation sequence.

7. The method of claim 1 wherein determining the physiological information comprises:
combining the plurality of autocorrelation sequences to generate a combined autocorrelation sequence; and
determining the physiological information based on the combined autocorrelation sequence.

8. The method of claim 7 wherein combining the plurality of autocorrelation sequences comprises:
calculating a plurality of combination weights; and
generating the combined autocorrelation sequence based on the plurality of autocorrelation sequences and the plurality of combination weights.

9. The method of claim 8 wherein calculating each of the plurality of combination weights comprises:
calculating an autocorrelation metric corresponding to the autocorrelation sequence;
calculating a ratio of the usable portion of the PPG signal;
calculating a correlation coefficient for the autocorrelation sequence; and calculating the combination weight based on the autocorrelation metric, the ratio, and the correlation coefficient.

10. The method of claim 8 further comprising:
calculating a plurality of sequence ages, wherein each sequence age corresponds to one of the plurality of autocorrelation sequences; and
calculating a combined autocorrelation age based on the plurality of combination weights and the plurality of sequence ages.

11. A patient monitoring system comprising:
a processor configured to:
generate a plurality of morphology metric signals based on a photoplethysmograph (PPG) signal;
generate a plurality of autocorrelation sequences, wherein each autocorrelation sequence is derived from a respective one of the morphology metric signals; and
determine physiological information from the plurality of autocorrelation sequences.

12. The patient monitoring system of claim 11, wherein the plurality of morphology metric signals comprise a down metric signal, a kurtosis metric signal, and a DSD metric signal.

13. The patient monitoring system of claim 11, the processor further configured to generate a plurality of autocorrelation metrics, wherein each autocorrelation metric corresponds to one of the autocorrelation sequences.

14. The patient monitoring system of claim 13, the processor further configured to:
identify a plurality of local minima points for each of the autocorrelation sequences;
normalize the local minima based on a peak for each of the autocorrelation sequences;
average the normalized local minimas for each of the autocorrelation sequences; and
generate the plurality of autocorrelation metrics based on the averages.

15. The patient monitoring system of claim 13, the processor further configured to:
generate an autocorrelation for each of the morphology metric signals;
calculate a ratio of the usable portion of each of the PPG signals;
calculate a plurality of filter weights based on the ratios and the autocorrelation metrics; and
filter the autocorrelations based on the filter weights to generate the autocorrelation sequences.

16. The patient monitoring system of claim 15, the processor further configured to calculate a sequence age for each of the autocorrelation sequences based on the filter weight for the autocorrelation sequence, a current age for the autocorrelation sequence, and a previous age for the autocorrelation sequence.

17. The patient monitoring system of claim 11, the processor further configured to combine the plurality of autocorrelation sequences to generate a combined autocorrelation sequence, and determine the physiological information based on the combined autocorrelation sequence.

18. The patient monitoring system of claim 17, the processor further configured to calculate a plurality of combination weights and generate the combined autocorrelation sequence based on the plurality of autocorrelation sequences and the plurality of combination weights.

19. The patient monitoring system of claim 18, the processor further configured to:
calculate an autocorrelation metric for each of the autocorrelation sequences;
calculate a ratio of the usable portion of the PPG signal for each of the autocorrelation sequences;
calculate a correlation coefficient for each of the autocorrelation sequences; and
calculate the combination weights based on the autocorrelation metrics, the ratios, and the correlation coefficients.

20. The patient monitoring system of claim 18, the processor further configured to calculate a plurality of sequence ages corresponding to the plurality of autocorrelation sequences and calculate a combined autocorrelation age based on the plurality of combination weights and the plurality of sequence ages.

* * * * *